United States Patent
Cho et al.

(10) Patent No.: US 7,319,098 B2
(45) Date of Patent: Jan. 15, 2008

(54) 1,3-DIOXOISOINDOLE DERIVATIVES HAVING SELECTIVE ANTAGONISM OF T-TYPE CALCIUM CHANNEL

(75) Inventors: Yong Seo Cho, Seoul (KR); Hyunah Choo, Seoul (KR); Ae Nim Pae, Seoul (KR); Joo Hwan Cha, Seoul (KR); Hun Yeong Koh, Seoul (KR); Hwa-Sil Kim, Seoul (KR); Hyewhon Rhim, Seoul (KR); Seon Hee Seo, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 11/600,391

(22) Filed: Nov. 16, 2006

(65) Prior Publication Data

US 2007/0259867 A1 Nov. 8, 2007

(30) Foreign Application Priority Data

May 4, 2006 (KR) ...................... 10-2006-0040614

(51) Int. Cl.
| | |
|---|---|
| A61K 31/5377 | (2006.01) |
| A61K 31/496 | (2006.01) |
| A61K 31/454 | (2006.01) |
| A61K 31/4025 | (2006.01) |
| C07D 413/12 | (2006.01) |
| C07D 403/12 | (2006.01) |
| C07D 401/12 | (2006.01) |
| C07D 207/06 | (2006.01) |

(52) U.S. Cl. .............................. 514/235.2; 514/254.09; 514/323; 514/414; 544/144; 544/373; 546/208; 548/518

(58) Field of Classification Search ................ 544/144, 544/373; 546/208; 548/518; 514/235.2, 514/254.09, 323, 414

See application file for complete search history.

(56) References Cited

OTHER PUBLICATIONS

NINDS Alzheimer's Disease Information page, retrieved from Internet on Apr. 5, 2007, <http://www.ninds.nih.gov/disorders/alzheimersdisease/alzheimersdisease.htm>.*
Selkoe, Alzheimer's Disease: Genes, Proteins, and Therapy, Apr. 2001, Physiological Reviews, vol. 81(2), 741-766.*
Nelson et al, Role of T-type Clacium Channels in Epilepy and Pain, 2006, Current Pharmaceutical Design, 12, p. 2189-2197.*
Hosravani, Houman et al., "Effects of Ca3.2 channel mutations linked to idiopathic generalized epilepsy", Annals of Neurology (2005), 57(5), 745-749.
Vitko, Iuliia et al., "Functional characterization and neuronal modeling of the effects of childhood absence epilepsy variants of CACNA1H, a T-type calcium channel", Journal of Neuroscience (2005), 25(19), 4844-4855.
Clozel et al., Cardiovas Drugs Ther. (1990), 4, pp. 731-736.
Hefti et al., Arzneimittelforschung (1990), 40, 417-421.
Moosmang, Sven et al., "Antihypertensive Effects of the Putative T-Type Calcium Channel Antagonist Mibefradil are Mediated by the L-Type Calcium Channel $Ca_v1.2$", Circulation Research (2006), 98(1), 105-110.
Flatters, Sarah J.L., "T-type calcium channels: A potential target for the treatment of chronic pain", Drugs of the Future (2005), 30(6), 573-580.
Barton, Matthew E. et al., "The antyhyperalgesic effects of the T-type calcium channel blockers ethosuximide, trimethadione, and mibefradil", European Journal of Pharmacology (2005), 521(1-3), 79-85.
Flatters, Sarah J.L. et al., "Ethosuximide reverses paclitaxel- and vincristine- induced painful peripheral neuropathy", Pain (2004), 109(1-2), 150-161.
Dogrul, Ahmet et al., "Reversal of experimental neuropathic paid by T-type calcium channel blockers", Pain (2003), 105(1-2), 159-168.

* cited by examiner

*Primary Examiner*—Rebecca Anderson
*Assistant Examiner*—Karen Cheng
(74) *Attorney, Agent, or Firm*—Frommer Lawrence & Haug LLP; Ronald R. Santucci

(57) ABSTRACT

The present invention relates to 1,3-dioxoisoindole derivatives of Formula (1) or pharmaceutically acceptable salts thereof, a preparation method thereof and use thereof as a T-type calcium channel antagonist, based on the fact that 1,3-dioxoisoindole derivatives of Formula (1) show selective antagonistic activity against T-type calcium channel, thus being effective in treating brain diseases, cardiac diseases and neurogenic pains:

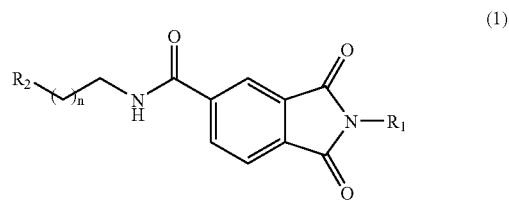

(1)

wherein $R_1$ is a phenyl or a benzyl group, optionally substituted with a moiety selected from the group consisting of a halogen atom, a $C_1$-$C_6$ alkoxy, a $C_1$-$C_6$ alkyl, and a cyano group; $R_2$ is a heterocyclic group selected from the group consisting of piperidinyl, pyrrolidinyl, morpholinyl, and piperazinyl groups, wherein the heterocyclic group is optionally substituted with a $C_1$-$C_6$ alkyl group; and n is 1 or 2.

9 Claims, No Drawings

1,3-DIOXOISOINDOLE DERIVATIVES HAVING SELECTIVE ANTAGONISM OF T-TYPE CALCIUM CHANNEL

This application claims priority benefits from Korean Patent Application No. 10-2006-0040614 filed May 4, 2006.

TECHNICAL FIELD

The present invention relates to 1,3-dioxoisoindole derivatives of Formula (1) or pharmaceutically acceptable salts thereof, a preparation method thereof and a medical use thereof as a T-type calcium channel antagonist, based on the fact that 1,3-dioxoisoindole derivatives of Formula (1) show selective antagonistic activity against T-type calcium channel, thus being effective in treating brain diseases, cardiac diseases and neurogenic pains:

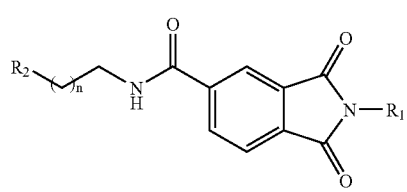

(1)

wherein $R_1$ is a phenyl or a benzyl group, optionally substituted with a moiety selected from the group consisting of a halogen atom, a $C_1$-$C_6$ alkoxy, a $C_1$-$C_6$ alkyl, and a cyano group; $R_2$ is a heterocyclic group selected from the group consisting of piperidinyl, pyrrolidinyl, morpholinyl, and piperazinyl group, wherein the heterocyclic group is optionally substituted with a $C_1$-$C_6$ alkyl group; and n is 1 or 2.

RELATED PRIOR ART

Calcium channel plays an important role in the intracellular signal transduction by increasing intracellular calcium concentration through nerve cell stimulation. Calcium channel is divided into high-voltage activated calcium channel and low-voltage activated calcium channel, and T-type calcium channel is a representative example of the low-voltage activated calcium channel. T-type calcium channel is found in central muscles, endocrine glands in the adrenal, sinoatrial node and heart. T-type calcium channel antagonist is known to have therapeutic effect on brain diseases such as epilepsy, hypertension and stenocardia and cardiac diseases [① Hosravani, Houman et al., "Effects of Cav3.2 channel mutations linked to idiopathic generalized epilepsy", *Annals of Neurology* (2005), 57(5), 745-749; ② Vitko, Iuliia et al., "Functional characterization and neuronal modeling of the effects of childhood absence epilepsy variants of CACNA1H, a T-type calcium channel", *Journal of Neuroscience* (2005), 25(19), 4844-4855; ③ Clozel, *Cardiovas Drugs Ther.* (1990), 4, pp. 731-736; ④ Hefti, *Arzneimittelforschung* (1990), 40, 417-421; ⑤ Moosmang, Sven et al., "Antihypertensive Effects of the Putative T-Type Calcium Channel Antagonist Mibefradil Are Mediated by the L-Type Calcium Channel Cav1. 2", *Circulation Research* (2006), 98(1), 105-110]. A recent study reported that T-type calcium channel antagonist has an activity in treatment of chronic pain [*Drugs of the Future* (2005), 40, 573-580]. For example, Mibefradil and Ethosuximide, as T-type calcium channel antagonists, showed dosage-dependent reversed mechanic and thermal induction in the spinal nerve ligation animal model, thus ascertaining that T-type calcium channel antagonist has a therapeutic effect on neurogenic pains [① Barton, Matthew E. et al., "The antihyperalgesic effects of the T-type calcium channel blockers ethosuximide, trimethadione, and mibefradil", *European Journal of Pharmacology* (2005), 521(1-3), 79-85; ② Flatters, Sarah J. L., "T-type calcium channels: A potential target for the treatment of chronic pain", *Drugs of the Future* (2005), 30(6), 573-580; ③ Flatters, Sarah J. L. et al., "Ethosuximide reverses paclitaxel- and vincristine-induced painful peripheral neuropathy", *Pain* (2004), 109(1-2), 150-161; ④ Dogrul, Ahmet et al., "Reversal of experimental neuropathic pain by T-type calcium channel blockers", *Pain* (2003), 105(1-2), 159-168].

Mibefradil, which had been on sale as T-type calcium channel antagonist for treatment of hypertension and stenocardia, was prohibited for sale due to its interaction with various drugs. Accordingly, there is an urgent need to develop a novel T-type calcium channel antagonist.

The present inventors have performed intensive researches to develop novel compound with activity against T-type calcium channel, and finally completed the present invention based on the findings that 1,3-dioxoisoindole derivatives show superior antagonistic activity against T-type calcium channel with various substituents.

Therefore, the present invention aims to provide novel 1,3-dioxoisoindole derivatives with various substituents and pharmaceutically acceptable salts thereof.

Further, the present invention also aims to provide a process of preparing the novel compound, which comprises a step of performing amidation reaction between azacyclic N-alkyl amine compound and 1,3-dioxoisoindole 5-carboxylic acid derivatives.

Furthermore, the present invention also aims to provide a medical use of the novel 1,3-dioxoisoindole derivatives or pharmaceutically acceptable salts thereof as an antagonist against T-type calcium channel.

DETAILED DESCRIPTION OF INVENTION

The present invention relates to 1,3-dioxoisoindole derivatives of Formula (1) or pharmaceutically acceptable salts thereof, a preparation method thereof and a medical use thereof as a T-type calcium channel antagonist, based on the fact that 1,3-dioxoisoindole derivatives of Formula (1) show selective antagonistic activity against T-type calcium channel, thus being effective in treating brain diseases, cardiac diseases and neurogenic pains:

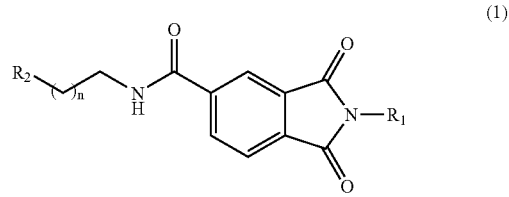

(1)

wherein $R_1$ is a phenyl or a benzyl group, optionally substituted with a moiety selected from the group consisting of a halogen atom, a $C_1$-$C_6$ alkoxy, a $C_1$-$C_6$ alkyl, and a cyano group; $R_2$ is a heterocyclic group selected from the group consisting of piperidinyl, pyrrolidinyl, morpholinyl, and piperazinyl groups, wherein the heterocyclic group is optionally substituted with a $C_1$-$C_6$ alkyl group; and n is 1 or 2.

Pharmaceutically acceptable salts of 1,3-dioxoisoindole derivatives of Formula (1) may be prepared by using the conventional methods. For example, 1,3-dioxoisoindole derivatives of Formula (1) may be reacted with non-toxic inorganic acid such as chloric acid, bromic acid, sulfonic acid, amidosulfonic acid, phosphoric acid and nitric acid or non-toxic organic acid such as acetic acid, propionic acid, succinic acid, glycolic acid, stearic acid, lactic acid, tartaric acid, citric acid, p-toluene sulfonic acid and methane sulfonic acid, to provide pharmaceutically acceptable salts herein.

Hereunder is provided a description of substituents in Formula (1). As used herein, "alkyl" includes straight, branched and cyclic hydrocarbon chains having 1 to 6 carbons. Preferable alkyl group include without limitation methyl, ethyl, propyl, isopropyl, butyl, t-butyl, cyclopentyl and cyclohexyl. As used herein, "alkoxy" refers to alkyl groups attached to a molecule through an oxygen atom, wherein the alkyl group are same as defined above. As used herein, "aryl" refers to monocyclic (at least 6 atoms) or bicyclic group (at least 10 atoms) or a stable moiety covalently bound to an adjacent carbon atom through a double bond, which are completely conjugated and stabilized. Examples of the aryl group include without limitation phenyl and naphthyl groups, and the aryl group herein may be substituted with at least one moiety selected from the group consisting of a halogen atom, alkyl, alkoxy and phenoxy groups. As used herein, "benzyl" refers to an aryl group substituted with a methylene, a carbon atom of which may form a valence bond with another atom. As used herein, "heterocyclic" refers to a saturated or unsaturated stable heterocyclic group with 5-7 atoms, which consists of carbon atoms and 1-3 hetero atoms such as N, O and S. Examples of the heterocyclic group include without limitation pyridine, pyrazine, pyrimidine, pyridazine, triazine, imidazole, triazole, quinoline, isoquinoline, quinazoline, quinoxaline, phthalazine, oxazole, isooxazole, thiazole, isothiazole, thiadiazole, oxadiazole, pyrrole, furan, thiophene, hydrogenated derivatives thereof such as piperidine, pyrrolidine, azetidine, tetrahydrofuran and N-oxide derivatives of basic nitrogen. The heterocyclic group herein may be substituted with at least one moiety selected from the group consisting of a halogen atom, alkyl, amine and alkylamino groups.

In Formula (1) above, $R_1$ is preferably phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 4-cyanophenyl, benzyl, 2-fluorobenzyl, 3-fluorobenzyl, 4-fluorobenzyl, 2-chlorobenzyl, 3-chlorobenzyl, 4-chlorobenzyl, 2-methylbenzyl, 3-methylbenzyl, 4-methylbenzyl, 2-methoxybenzyl, 3-methoxybenzyl, 4-methoxybenzyl or 4-cyanobenzyl group; $R_2$ is preferably 1-piperadinyl, 2-methylpiperidin-1-yl, 2-ethylpiperidin-1-yl, 1-pyrrolidinyl, 1-morpholinyl or 4-methylpiperazin-1-yl; n is 1 or 2.

Examples of the 1,3-dioxoisoindole derivatives of Formula (1) include but are not limited to the following compounds:

1-{2-[(1,3-dioxo-2-phenyl-2,3-dihydro-1H-isoindol-5-carbonyl)-amino]-ethyl}-piperidinium chloride;
1-{3-[(1,3-dioxo-2-phenyl-2,3-dihydro-1H-isoindol-5-carbonyl)-amino]-propyl}-2-methyl-piperidinium chloride;
1-{2-[(1,3-dioxo-2-phenyl-2,3-dihydro-1H-isoindol-5-carbonyl)-amino]-ethyl}-pyrrolidinium chloride;
1-{3-[(1,3-dioxo-2-phenyl-2,3-dihydro-1H-isoindol-5-carbonyl)-amino]-propyl}-pyrrolidinium chloride;
4-{2-[(1,3-dioxo-2-phenyl-2,3-dihydro-1H-isoindol-5-carbonyl)-amino]-ethyl}-4-morpholinium chloride;
4-{3-[(1,3-dioxo-2-phenyl-2,3-dihydro-1H-isoindol-5-carbonyl)-amino]-propyl}-4-morpholinium chloride;
1-(2-{[2-(2-fluoro-phenyl)-1,3-dioxo-2,3-dihydro-1H-isoindol-5-carbonyl]-amino}-ethyl)-piperidinium chloride;
1-(3-{[2-(2-fluoro-phenyl)-1,3-dioxo-2,3-dihydro-1H-isoindol-5-carbonyl]-amino}-propyl)-2-methyl-piperidinium chloride;
1-(2-{[2-(2-fluoro-phenyl)-1,3-dioxo-2,3-dihydro-1H-isoindol-5-carbonyl]-amino}-ethyl)-pyrrolidinium chloride;
1-(3-{[2-(2-fluoro-phenyl)-1,3-dioxo-2,3-dihydro-1H-isoindol-5-carbonyl]-amino}-propyl)-pyrrolidinium chloride;
4-(2-{[2-(2-fluoro-phenyl)-1,3-dioxo-2,3-dihydro-1H-isoindol-5-carbonyl]-amino}-ethyl)-4-morpholinium chloride;
4-(3-{[2-(2-fluoro-phenyl)-1,3-dioxo-2,3-dihydro-1H-isoindol-5-carbonyl]-amino}-propyl)-4-morpholinium chloride;
1-(2-{[2-(3-fluoro-phenyl)-1,3-dioxo-2,3-dihydro-1H-isoindol-5-carbonyl]-amino}-ethyl)-piperidinium chloride;
1-(3-{[2-(3-fluoro-phenyl)-1,3-dioxo-2,3-dihydro-1H-isoindol-5-carbonyl]-amino}-propyl)-2-methyl-piperidinium chloride;
1-(2-{[2-(3-fluoro-phenyl)-1,3-dioxo-2,3-dihydro-1H-isoindol-5-carbonyl]-amino}-ethyl)-pyrrolidinium chloride;
1-(3-{[2-(3-fluoro-phenyl)-1,3-dioxo-2,3-dihydro-1H-isoindol-5-carbonyl]-amino}-propyl)-pyrrolidinium chloride;
4-(2-{[2-(3-fluoro-phenyl)-1,3-dioxo-2,3-dihydro-1H-isoindol-5-carbonyl]-amino}-ethyl)-4-morpholinium chloride;
4-(3-{[2-(3-fluoro-phenyl)-1,3-dioxo-2,3-dihydro-1H-isoindol-5-carbonyl]-amino}-propyl)-4-morpholinium chloride;
1-(2-{[2-(4-fluoro-phenyl)-1,3-dioxo-2,3-dihydro-1H-isoindol-5-carbonyl]-amino}-ethyl)-piperidinium chloride;
1-(3-{[2-(4-fluoro-phenyl)-1,3-dioxo-2,3-dihydro-1H-isoindol-5-carbonyl]-amino}-propyl)-2-methyl-piperidinium chloride;
1-(2-{[2-(4-fluoro-phenyl)-1,3-dioxo-2,3-dihydro-1H-isoindol-5-carbonyl]-amino}-ethyl)-pyrrolidinium chloride;
1-(3-{[2-(4-fluoro-phenyl)-1,3-dioxo-2,3-dihydro-1H-isoindol-5-carbonyl]-amino}-propyl)-pyrrolidinium chloride;
4-(2-{[2-(4-fluoro-phenyl)-1,3-dioxo-2,3-dihydro-1H-isoindol-5-carbonyl]-amino}-ethyl)-4-morpholinium chloride;
4-(3-{[2-(4-fluoro-phenyl)-1,3-dioxo-2,3-dihydro-1H-isoindol-5-carbonyl]-amino}-propyl)-4-morpholinium chloride;
1-(2-{[2-(2-chloro-phenyl)-1,3-dioxo-2,3-dihydro-1H-isoindol-5-carbonyl]-amino}-ethyl)-piperidinium chloride;
1-(2-{[2-(3-chloro-phenyl)-1,3-dioxo-2,3-dihydro-1H-isoindol-5-carbonyl]-amino}-ethyl)-piperidinium chloride;

1-(2-{[2-(4-chloro-phenyl)-1,3-dioxo-2,3-dihydro-1H-isoindol-5-carbonyl]-amino}-ethyl)-piperidinium chloride;
1-{2-[(1,3-dioxo-2-o-tolyl-2,3-dihydro-1H-isoindol-5-carbonyl)-amino]-ethyl}-piperidinium chloride;
1-{3-[(1,3-dioxo-2-o-tolyl-2,3-dihydro-1H-isoindol-5-carbonyl)-amino]-propyl}-2-methyl-piperidinium chloride;
1-{2-[(1,3-dioxo-2-o-tolyl-2,3-dihydro-1H-isoindol-5-carbonyl)-amino-ethyl}-pyrrolidinium chloride;
1-{3-[(1,3-dioxo-2-o-tolyl-2,3-dihydro-1H-isoindol-5-carbonyl)-amino]-propyl}-pyrrolidinium chloride;
4-{2-[(1,3-dioxo-2-o-tolyl-2,3-dihydro-1H-isoindol-5-carbonyl)-amino]-ethyl}-4-morpholinium chloride;
1-{2-[(1,3-dioxo-2-m-tolyl-2,3-dihydro-1H-isoindol-5-carbonyl)-amino]-ethyl}-piperidinium chloride;
1-{3-[(1,3-dioxo-2-m-tolyl-2,3-dihydro-1H-isoindol-5-carbonyl)-amino]-propyl}-2-methyl-piperidinium chloride;
1-{2-[(1,3-dioxo-2-m-tolyl-2,3-dihydro-1H-isoindol-5-carbonyl)-amino]-ethyl}-pyrrolidinium chloride;
1-{3-[(1,3-dioxo-2-m-tolyl-2,3-dihydro-1H-isoindol-5-carbonyl)-amino]-propyl}-pyrrolidinium chloride;
4-{2-[(1,3-dioxo-2-m-tolyl-2,3-dihydro-1H-isoindol-5-carbonyl)-amino]-ethyl}-4-morpholinium chloride;
4-{3-[(1,3-dioxo-2-m-tolyl-2,3-dihydro-1H-isoindol-5-carbonyl)-amino]-propyl}-4-morpholinium chloride;
1-{2-[(1,3-dioxo-2-p-tolyl-2,3-dihydro-1H-isoindol-5-carbonyl)-amino]-ethyl}-piperidinium chloride;
1-{3-[(1,3-dioxo-2-p-tolyl-2,3-dihydro-1H-isoindol-5-carbonyl)-amino]-propyl}-2-methyl-piperidinium chloride;
1-{2-[(1,3-dioxo-2-p-tolyl-2,3-dihydro-1H-isoindol-5-carbonyl)-amino]-ethyl}-pyrrolidinium chloride;
1-(3-{[2-(2-methoxy-phenyl)-1,3-dioxo-2,3-dihydro-1H-isoindol-5-carbonyl]-amino}-propyl)-2-methyl-piperidinium chloride;
1-(2-{[2-(2-methoxy-phenyl)-1,3-dioxo-2,3-dihydro-1H-isoindol-5-carbonyl]-amino}-ethyl)-pyrrolidinium chloride;
1-(3-{[2-(2-methoxy-phenyl)-1,3-dioxo-2,3-dihydro-1H-isoindol-5-carbonyl]-amino}-propyl)-pyrrolidinium chloride;
4-(3-{[2-(2-methoxy-phenyl)-1,3-dioxo-2,3-dihydro-1H-isoindol-5-carbonyl]-amino}-propyl)-4-morpholinium chloride;
1-(2-{[2-(3-methoxy-phenyl)-1,3-dioxo-2,3-dihydro-1H-isoindol-5-carbonyl]-amino}-ethyl)-piperidinium chloride;
1-(2-{[2-(4-methoxy-phenyl)-1,3-dioxo-2,3-dihydro-1H-isoindol-5-carbonyl]-amino}-ethyl)-piperidinium chloride;
1-{2-[(2-benzyl-1,3-dioxo-2,3-dihydro-1H-isoindol-5-carbonyl)-amino]-ethyl}-piperidinium chloride;
1-{3-[(2-benzyl-1,3-dioxo-2,3-dihydro-1H-isoindol-5-carbonyl)-amino]-propyl}-2-methyl-piperidinium chloride;
1-{2-[(2-benzyl-1,3-dioxo-2,3-dihydro-1H-isoindol-5-carbonyl)-amino]-ethyl}-pyrrolidinium chloride;
1-{3-[(2-benzyl-1,3-dioxo-2,3-dihydro-1H-isoindol-5-carbonyl)-amino]-propyl}-pyrrolidinium chloride;
4-{2-[(2-benzyl-1,3-dioxo-2,3-dihydro-1H-isoindol-5-carbonyl)-amino]-ethyl}-4-morpholinium chloride;
4-{3-[(2-benzyl-1,3-dioxo-2,3-dihydro-1H-isoindol-5-carbonyl)-amino]-propyl}-4-morpholinium chloride;
1-(2-{[2-(2-fluoro-benzyl)-1,3-dioxo-2,3-dihydro-1H-isoindol-5-carbonyl]-amino}-ethyl)-piperidinium chloride;
1-(3-{[2-(2-fluoro-benzyl)-1,3-dioxo-2,3-dihydro-1H-isoindol-5-carbonyl]-amino}-propyl)-2-methyl-piperidinium chloride;
1-(2-{[2-(2-fluoro-benzyl)-1,3-dioxo-2,3-dihydro-1H-isoindol-5-carbonyl]-amino}-ethyl)-pyrrolidinium chloride;
1-(3-{[2-(2-fluoro-benzyl)-1,3-dioxo-2,3-dihydro-1H-isoindol-5-carbonyl]-amino}-propyl)-pyrrolidinium chloride;
4-(2-{[2-(2-fluoro-benzyl)-1,3-dioxo-2,3-dihydro-1H-isoindol-5-carbonyl]-amino}-ethyl)-4-morpholinium chloride;
4-(3-{[2-(2-fluoro-benzyl)-1,3-dioxo-2,3-dihydro-1H-isoindol-5-carbonyl]-amino}-propyl)-4-morpholinium chloride;
1-(2-{[2-(3-fluoro-benzyl)-1,3-dioxo-2,3-dihydro-1H-isoindol-5-carbonyl]-amino}-ethyl)-piperidinium chloride;
1-(3-{[2-(3-fluoro-benzyl)-1,3-dioxo-2,3-dihydro-1H-isoindol-5-carbonyl]-amino}-propyl)-2-methyl-piperidinium chloride;
1-(2-{[2-(3-fluoro-benzyl)-1,3-dioxo-2,3-dihydro-1H-isoindol-5-carbonyl]-amino}-ethyl)-pyrrolidinium chloride;
1-(3-{[2-(3-fluoro-benzyl)-1,3-dioxo-2,3-dihydro-1H-isoindol-5-carbonyl]-amino}-propyl)-pyrrolidinium chloride;
4-(2-{[2-(3-fluoro-benzyl)-1,3-dioxo-2,3-dihydro-1H-isoindol-5-carbonyl]-amino}-ethyl)-4-morpholinium chloride;
4-(3-{[2-(3-fluoro-benzyl)-1,3-dioxo-2,3-dihydro-1H-isoindol-5-carbonyl]-amino}-propyl)-4-morpholinium chloride;
1-(3-{[2-(3-fluoro-benzyl)-1,3-dioxo-2,3-dihydro-1H-isoindol-5-carbonyl]-amino}-propyl)-4-methyl-1-piperazinium chloride;
1-(2-{[2-(4-fluoro-benzyl)-1,3-dioxo-2,3-dihydro-1H-isoindol-5-carbonyl]-amino}-ethyl)-piperidinium chloride;
1-(3-{[2-(4-fluoro-benzyl)-1,3-dioxo-2,3-dihydro-1H-isoindol-5-carbonyl]-amino}-propyl)-2-methyl-piperidinium chloride;
1-(2-{[2-(4-fluoro-benzyl)-1,3-dioxo-2,3-dihydro-1H-isoindol-5-carbonyl]-amino}-ethyl)-pyrrolidinium chloride;
1-(3-{[2-(4-fluoro-benzyl)-1,3-dioxo-2,3-dihydro-1H-isoindol-5-carbonyl]-amino}-propyl)-pyrrolidinium chloride;
4-(2-{[2-(4-fluoro-benzyl)-1,3-dioxo-2,3-dihydro-1H-isoindol-5-carbonyl]-amino}-ethyl)-4-morpholinium chloride;
4-(3-{[2-(4-fluoro-benzyl)-1,3-dioxo-2,3-dihydro-1H-isoindol-5-carbonyl]-amino}-propyl)-4-morpholinium chloride;
1-(3-{[2-(4-fluoro-benzyl)-1,3-dioxo-2,3-dihydro-1H-isoindol-5-carbonyl]-amino}-propyl)-4-methyl-1-piperazinium chloride;
1-(2-{[2-(2-chloro-benzyl)-1,3-dioxo-2,3-dihydro-1H-isoindol-5-carbonyl]-amino}-ethyl)-piperidinium chloride;
1-(3-{[2-(2-chloro-benzyl)-1,3-dioxo-2,3-dihydro-1H-isoindol-5-carbonyl]-amino}-propyl)-2-methyl-piperidinium chloride;
1-(2-{[2-(2-chloro-benzyl)-1,3-dioxo-2,3-dihydro-1H-isoindol-5-carbonyl]-amino}-ethyl)-pyrrolidinium chloride;
1-(3-{[2-(2-chloro-benzyl)-1,3-dioxo-2,3-dihydro-1H-isoindol-5-carbonyl]-amino}-propyl)-pyrrolidinium chloride;
4-(2-{[2-(2-chloro-benzyl)-1,3-dioxo-2,3-dihydro-1H-isoindol-5-carbonyl]-amino}-ethyl)-4-morpholinium chloride;
4-(3-{[2-(2-chloro-benzyl)-1,3-dioxo-2,3-dihydro-1H-isoindol-5-carbonyl]-amino}-propyl)-4-morpholinium chloride;
1-(2-{[2-(3-chloro-benzyl)-1,3-dioxo-2,3-dihydro-1H-isoindol-5-carbonyl]-amino}-ethyl)-piperidinium chloride;
1-(3-{[2-(3-chloro-benzyl)-1,3-dioxo-2,3-dihydro-1H-isoindol-5-carbonyl]-amino}-propyl)-2-methyl-piperidinium chloride;

1-(2-{[2-(3-chloro-benzyl)-1,3-dioxo-2,3-dihydro-1H-isoindol-5-carbonyl]-amino}-ethyl)-pyrrolidinium chloride;
1-(3-{[2-(3-chloro-benzyl)-1,3-dioxo-2,3-dihydro-1H-isoindol-5-carbonyl]-amino}-propyl)-pyrrolidinium chloride;
4-(2-{[2-(3-chloro-benzyl)-1,3-dioxo-2,3-dihydro-1H-isoindol-5-carbonyl]-amino}-ethyl)-4-morpholinium chloride;
4-(3-{[2-(3-chloro-benzyl)-1,3-dioxo-2,3-dihydro-1H-isoindol-5-carbonyl]-amino}-propyl)-4-morpholinium chloride;
1-(2-{[2-(4-chloro-benzyl)-1,3-dioxo-2,3-dihydro-1H-isoindol-5-carbonyl]-amino}-ethyl)-piperidinium chloride;
1-(3-{[2-(4-chloro-benzyl)-1,3-dioxo-2,3-dihydro-1H-isoindol-5-carbonyl]-amino}-propyl)-2-methyl-piperidinium chloride;
1-(2-{[2-(4-chloro-benzyl)-1,3-dioxo-2,3-dihydro-1H-isoindol-5-carbonyl]-amino}-ethyl)-pyrrolidinium chloride;
1-(3-{[2-(4-fluoro-benzyl)-1,3-dioxo-2,3-dihydro-1H-isoindol-5-carbonyl]-amino}-propyl)-pyrrolidinium chloride;
4-(2-{[2-(4-chloro-benzyl)-1,3-dioxo-2,3-dihydro-1H-isoindol-5-carbonyl]-amino}-ethyl)-4-morpholinium chloride;
4-(3-[2-(4-chloro-benzyl)-1,3-dioxo-2,3-dihydro-1H-isoindol-5-carbonyl]-amino)-propyl)-4-morpholinium chloride;
1-(2-{[2-(2-methyl-benzyl)-1,3-dioxo-2,3-dihydro-1H-isoindol-5-carbonyl]-amino}-ethyl)-piperidinium chloride;
2-methyl-1-(3-{[2-(2-methyl-benzyl)-1,3-dioxo-2,3-dihydro-1H-isoindol-5-carbonyl]-amino}-propyl)-piperidinium chloride;
1-(2-{[2-(2-methyl-benzyl)-1,3-dioxo-2,3-dihydro-1H-isoindol-5-carbonyl]-amino}-ethyl)-pyrrolidinium chloride;
1-(3-{[2-(2-methyl-benzyl)-1,3-dioxo-2,3-dihydro-1H-isoindol-5-carbonyl]-amino}-propyl)-pyrrolidinium chloride;
4-(2-{[2-(2-methyl-benzyl)-1,3-dioxo-2,3-dihydro-1H-isoindol-5-carbonyl]-amino}-ethyl)-4-morpholinium chloride;
4-(3-{[2-(2-methyl-benzyl)-1,3-dioxo-2,3-dihydro-1H-isoindol-5-carbonyl]-amino}-propyl)-4-morpholinium chloride;
1-(2-{[2-(3-methyl-benzyl)-1,3-dioxo-2,3-dihydro-1H-isoindol-5-carbonyl]-amino}-ethyl)-piperidinium chloride;
2-methyl-1-(3-{[2-(3-methyl-benzyl)-1,3-dioxo-2,3-dihydro-1H-isoindol-5-carbonyl]-amino}-propyl)-piperidinium chloride;
1-(2-{[2-(3-methyl-benzyl)-1,3-dioxo-2,3-dihydro-1H-isoindol-5-carbonyl]-amino}-ethyl)-pyrrolidinium chloride;
1-(3-{[2-(3-methyl-benzyl)-1,3-dioxo-2,3-dihydro-1H-isoindol-5-carbonyl]-amino}-propyl)-pyrrolidinium chloride;
4-(2-{[2-(3-methyl-benzyl)-1,3-dioxo-2,3-dihydro-1H-isoindol-5-carbonyl]-amino}-ethyl)-4-morpholinium chloride;
4-(3-{[2-(3-methyl-benzyl)-1,3-dioxo-2,3-dihydro-1H-isoindol-5-carbonyl]-amino}-propyl)-4-morpholinium chloride;
1-(2-{[2-(4-methyl-benzyl)-1,3-dioxo-2,3-dihydro-1H-isoindol-5-carbonyl]-amino}-ethyl)-piperidinium chloride;
1-(3-{[2-(4-methyl-benzyl)-1,3-dioxo-2,3-dihydro-1H-isoindol-5-carbonyl]-amino}-propyl)-piperidinium chloride;
1-(2-{[2-(4-methyl-benzyl)-1,3-dioxo-2,3-dihydro-1H-isoindol-5-carbonyl]-amino}-ethyl)-pyrrolidinium chloride;
1-(3-{[2-(4-methyl-benzyl)-1,3-dioxo-2,3-dihydro-1H-isoindol-5-carbonyl]-amino}-propyl)-pyrrolidinium chloride;
4-(2-{[2-(4-methyl-benzyl)-1,3-dioxo-2,3-dihydro-1H-isoindol-5-carbonyl]-amino}-ethyl)-4-morpholinium chloride;
4-(3-{[2-(4-methyl-benzyl)-1,3-dioxo-2,3-dihydro-1H-isoindol-5-carbonyl]-amino}-propyl)-4-morpholinium chloride;
1-(2-{[2-(2-methoxy-benzyl)-1,3-dioxo-2,3-dihydro-1H-isoindol-5-carbonyl]-amino}-ethyl)-piperidinium chloride;
1-(3-{[2-(2-methoxy-benzyl)-1,3-dioxo-2,3-dihydro-1H-isoindol-5-carbonyl]-amino}-propyl)-2-methyl-piperidinium chloride;
1-(2-{[2-(2-methoxy-benzyl)-1,3-dioxo-2,3-dihydro-1H-isoindol-5-carbonyl]-amino}-ethyl)-pyrrolidinium chloride;
1-(3-{[2-(2-methoxy-benzyl)-1,3-dioxo-2,3-dihydro-1H-isoindol-5-carbonyl]-amino}-propyl)-pyrrolidinium chloride;
4-(2-{[2-(2-methoxy-benzyl)-1,3-dioxo-2,3-dihydro-1H-isoindol-5-carbonyl]-amino}-ethyl)-4-morpholinium chloride;
4-(3-{[2-(2-methoxy-benzyl)-1,3-dioxo-2,3-dihydro-1H-isoindol-5-carbonyl]-amino}-propyl)-4-morpholinium chloride;
1-(2-{[2-(3-methoxy-benzyl)-1,3-dioxo-2,3-dihydro-1H-isoindol-5-carbonyl]-amino}-ethyl)-piperidinium chloride;
1-(3-{[2-(3-methoxy-benzyl)-1,3-dioxo-2,3-dihydro-1H-isoindol-5-carbonyl]-amino}-propyl)-2-methyl-piperidinium chloride;
1-(2-{[2-(3-methoxy-benzyl)-1,3-dioxo-2,3-dihydro-1H-isoindol-5-carbonyl]-amino}-ethyl)-pyrrolidinium chloride;
1-(3-{[2-(3-methoxy-benzyl)-1,3-dioxo-2,3-dihydro-1H-isoindol-5-carbonyl]-amino}-propyl)-pyrrolidinium chloride;
4-(2-{[2-(3-methoxy-benzyl)-1,3-dioxo-2,3-dihydro-1H-isoindol-5-carbonyl]-amino}-ethyl)-4-morpholinium chloride;
4-(3-{[2-(3-methoxy-benzyl)-1,3-dioxo-2,3-dihydro-1H-isoindol-5-carbonyl]-amino}-propyl)-4-morpholinium chloride;
1-(2-{[2-(4-methoxy-benzyl)-1,3-dioxo-2,3-dihydro-1H-isoindol-5-carbonyl]-amino}-ethyl)-piperidinium chloride;
1-(3-{[2-(4-methoxy-benzyl)-1,3-dioxo-2,3-dihydro-1H-isoindol-5-carbonyl]-amino}-propyl)-2-methyl-piperidinium chloride;
1-(2-{[2-(4-methoxy-benzyl)-1,3-dioxo-2,3-dihydro-1H-isoindol-5-carbonyl]-amino}-ethyl)-pyrrolidinium chloride;
1-(3-{[2-(4-methoxy-benzyl)-1,3-dioxo-2,3-dihydro-1H-isoindol-5-carbonyl]-amino}-propyl)-pyrrolidinium chloride;

4-(2-{[2-(4-methoxy-benzyl)-1,3-dioxo-2,3-dihydro-1H-isoindol-5-carbonyl]-amino}-ethyl)-4-morpholinium chloride;

4-(3-{[2-(4-methoxy-benzyl)-1,3-dioxo-2,3-dihydro-1H-isoindol-5-carbonyl]-amino}-propyl)-4-morpholinium chloride;

1-(2-{[2-(4-cyano-benzyl)-1,3-dioxo-2,3-dihydro-1H-isoindol-5-carbonyl]-amino}-ethyl)-piperidinium chloride;

1-(3-{[2-(4-cyano-benzyl)-1,3-dioxo-2,3-dihydro-1H-isoindol-5-carbonyl]-amino}-propyl)-2-methyl-piperidinium chloride;

1-(2-{[2-(4-cyano-benzyl)-1,3-dioxo-2,3-dihydro-1H-isoindol-5-carbonyl]-amino}-ethyl)-pyrrolidinium chloride;

1-(3-{[2-(4-cyano-benzyl)-1,3-dioxo-2,3-dihydro-1H-isoindol-5-carbonyl]-amino}-propyl)-pyrrolidinium chloride;

4-(2-{[2-(4-cyano-benzyl)-1,3-dioxo-2,3-dihydro-1H-isoindol-5-carbonyl]-amino}-ethyl)-4-morpholinium chloride;

4-(3-{[2-(4-cyano-benzyl)-1,3-dioxo-2,3-dihydro-1H-isoindol-5-carbonyl]-amino}-propyl)-4-morpholinium chloride.

Meanwhile, the present invention also relates to a process of preparing 1,3-dioxoisoindole derivatives of Formula (1) as described in Scheme 1.

Scheme 1

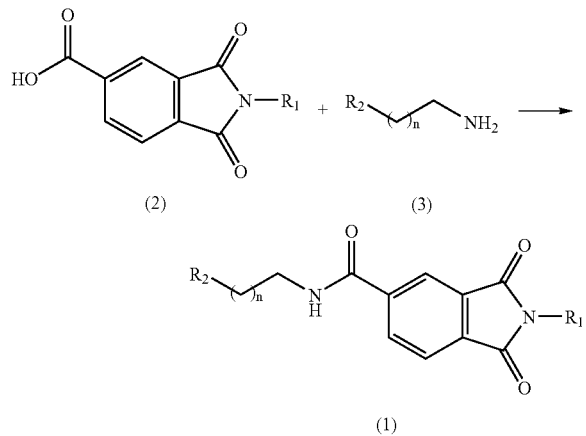

wherein $R_1$, $R_2$, and n are same as defined in Formula (1).

As shown in Scheme 1 above, 1,3-dioxoisoindole 5-carboxylic acid derivatives of Formula (2) are reacted with azacyclic N-alkyl amine compound of Formula (3) via amide condensation reaction, thereby providing a compound of Formula (1).

The amide condensation reaction was performed via two steps in a reactor. That is, carboxylic acid derivatives of Formula (2) were formed into an acyl chloride compound as an intermediate product under nitrogen condition, followed by addition of amine compound of Formula (3), thereby providing a compound of Formula (1).

In the acyl chlorination reaction, oxalyl chloride or thionyl chloride may be used as an acylating reagent, the amount of which depends on the reactivity. About 10-20 equivalents are sufficient, and 10-12 equivalents are preferable. 0.1-0.3 equivalents of dimethylformaldehyde may be used as an acylating catalyst. Examples of solvents include without limitation methylene chloride, chloroform and 1,2-dichloroethane. Methylene chloride was used in Examples herein. The acylation reaction is performed for 1-3 hours, preferably 1-1.5 hours at room temperature. After the acylation reaction is terminated, solvent is vacuum distilled and the produced acyl chloride intermediate product is dried at reduced vacuum.

The dried acyl chloride intermediate product is dissolved in methylene chloride with nitrogen purged, followed by addition of amine compound of Formula (3). The reaction time and temperature are preferred to be 1-5 hours and 0° C. to room temperature, respectively. After the reaction is terminated, solvent is vacuum distilled and pure 1,3-dioxoisoindole derivatives are obtained by column chromatography.

Further, pharmaceutically acceptable salts of 1,3-dioxoisoindole derivatives herein may be easily produced according to a conventional method in the pure form without additional purification process. Hereunder is provided description of production of the pharmaceutical salts with focusing on chlorate salt. That is, the obtained 1,3-dioxoisoindole derivatives is dissolved in methylene chloride, and 1-10 equivalents of hydrogen chloride solution is added, thereby providing solid-state chlorinate salt of a Target compound in the amount of. Examples of solvents used to prepare the hydrogen chloride solution include without limitation chloroform, methylene chloride, diethyl ether, methanol, ethyl acetate or a mixture thereof, preferably diethyl ether. The solid-state products may be separated by using a centrifuge or solvent remover with cotton. The solid is washed 2-3 times with 1-2 mL of diethyl ether and dried to provide pure chlorate salt in solid state.

Further, 1,3-dioxoisoindole 5-carboxylic acid derivatives of Formula (2), which is used as a starting material herein, may be easily prepared according to conventional method. Azacyclic N-alkyl amine compound of Formula (3), the other starting material, may also be prepared according to a conventional method or purchased.

Meanwhile, based on the findings that 1,3-dioxoisoindole derivatives of Formula (1) or pharmaceutically acceptable salts thereof is superior as T-type calcium channel antagonist, the present invention also relates to a pharmaceutical composition comprising novel compound of Formula (1) as an active ingredient. Further, the present invention also relates to a drug comprising 1,3-dioxoisoindole derivatives of Formula (1) or pharmaceutically acceptable salts thereof as an active ingredient for treating brain diseases such as epilepsy or cardiac disorders such as hypertension and stenocardia or neurogenic pain. The pharmaceutical composition herein may further comprise conventional non-toxic pharmaceutically acceptable carriers, enhancers and excipients, and may be prepared into various formulations for oral administration such as tablets, capsules, troches, liquids and suspensions or other parenteral formulations. An appropriate dosage level of the compound of Formula (1) may be determined after considering various information such as formulation method, administration type, age, body weight, sex, physical conditions food, administration time and route, excretion and reaction sensitivity of a subject. Physicians with average skill may easily determine and diagnose the dosage level of medicine effective for treating or preventing target disorders or diseases. In a preferred embodiment, the dosage level for an adult weighing 70 kg is 0.01-2000 mg/day, and may be administered once a day or in divided doses daily according to prescription instructions.

EXAMPLES

The present invention is described more specifically by the following Examples. Examples herein are meant only to illustrate the present invention, but they should not be construed as limiting the scope of the claimed invention.

Example 1

Synthesis of 1-{2-[(1,3-dioxo-2-phenyl-2,3-dihydro-1H-isoindol-5-carbonyl)-amino]-ethyl}-piperidinium chloride (Compound 1)

A mixture of 1,3-dioxo-2-phenyl-2,3-dihydro-1H-isoindol-5-carboxylic acid (100 mg, 0.374 mmol) and methylene chloride (4 mL) was treated with oxalylchloride (0.5 mL) and DMF (50 μL) which were added dropwise, and the resulting reaction mixture was stirred for 1.5 h. After concentration to dryness under the reduced pressure, 105 mg of acylchloride was obtained as an intermediate product.

2-(2-chloro-benzyl)-1,3-dioxo-2,3-dihydro-1H-isoindol-5-carbonyl chloride: $^1$H NMR (400 MHz, CDCl$_3$) δ 8.62-8.58 (m, 1H), 8.50 (dd, 1H, J=7.8, 1.6 Hz), 8.03 (d, 1H, J=7.8 Hz), 7.42-7.37 (m, 1H), 7.25-7.17 (m, 3H), 4.87 (s, 2H).

Thus obtained acylchloride was dissolved in methylene chloride (4 mL) under nitrogen atmosphere, and 2-piperidin-2-yl-ethylamine (100 μL, 0.704 mmol) was added dropwise with sufficient stirring. After 2 h, the reaction mixture was concentrated and purified by column chromatography to give the pure product. Thus-obtained compound was dissolved in 0.5 mL of methylene chloride, and 1M HCl solution in diethyl ether (0.56 mL) was added to the solution of the product. The precipitate was filtered and dried under reduced pressure to afford the target compound as HCl salt form in 70% yield.

$^1$H NMR (400 MHz, DMSO-d$_6$) δ 10.42 (br s, 1H), 9.53 (t, 1H, J=5.3 Hz), 8.43 (s, 1H), 8.42 (d, 1H, J=8.4 Hz), 8.06 (d, 1H, J=7.6 Hz), 7.60-7.35 (m, 5H), 3.81-3.65 (m, 2H), 3.58-3.41 (m, 2H), 3.29-3.16 (m, 2H), 3.00-2.80 (m, 2H), 1.92-1.61 (m, 5H), 1.48-1.30 (m, 1H).

Example 2

Synthesis of 1-{3-[(1,3-dioxo-2-phenyl-2,3-dihydro-1H-isoindol-5-carbonyl)-amino]-propyl}-2-methyl-piperidinium chloride (Compound 2)

1,3-dioxo-2-phenyl-2,3-dihydro-1H-isoindol-5-carboxylic acid (100 mg, 0.374 mmol) and 3-(2-methylpiperidin-1-yl)propan-1-amine (100 μL, 0.576 mmol) were reacted with each other. Target compound in the amount of 152 mg (92%) was obtained by following the procedure described in Example 1.

$^1$H NMR (400 MHz, DMSO-d$_6$) δ 10.40 (br s, 1H), 9.20-9.08 (m, 1H), 8.39 (s, 1H), 8.36 (d, 1H, J=7.7 Hz), 8.05 (d, 1H, J=7.6 Hz), 7.60-7.34 (m, 5H), 1.28 (d, 2.1H, J=6.1 Hz), 1.21 (d, 0.9H, J=6.8 Hz).

Example 3

Synthesis of 1-{2-[(1,3-dioxo-2-phenyl-2,3-dihydro-1H-isoindol-5-carbonyl)-amino]-ethyl}-pyrrolidinium chloride (Compound 3)

1,3-dioxo-2-phenyl-2,3-dihydro-1H-isoindol-5-carboxylic acid (100 mg, 0.374 mmol) and 2-pyrrolidin-1-yl-ethylamine (100 μL, 0.789 mmol) were reacted with each other. Target compound in the amount of 100 mg (67%) was obtained by following the procedure described in Example 1.

$^1$H NMR (400 MHz, DMSO-d$_6$) δ 10.68 (s, 1H), 9.34-9.22 (m, 1H), 8.43 (s, 1H), 8.42 (d, 1H, J=7.9 Hz), 8.06 (d, 1H, J=7.7 Hz), 7.60-7.36 (m, 5H), 3.79-3.54 (m, 4H), 3.52-3.39 (m, 2H), 3.11-2.93 (m, 2H), 2.10-1.78 (m, 4H).

Example 4

Synthesis of 1-{3-[(1,3-dioxo-2-phenyl-2,3-dihydro-1H-isoindol-5-carbonyl)-amino]-propyl}-pyrrolidinium chloride (Compound 4)

1,3-dioxo-2-phenyl-2,3-dihydro-1H-isoindol-5-carboxylic acid (100 mg, 0.374 mmol) and 3-pyrrolidin-1-yl-propylamine (100 μL, 0.772 mmol) were reacted with each other. Target compound in the amount of 130 mg (84%) was obtained by following the procedure described in Example 1.

$^1$H NMR (400 MHz, DMSO-d$_6$) δ 10.73 (br s, 1H), 9.11 (br s, 1H), 8.39 (s, 1H), 8.36 (d, 1H, J=7.7 Hz), 8.05 (d, 1H, J=7.5 Hz), 3.61-3.43 (m, 2H), 3.43-3.36 (m, 2H), 3.25-3.09 (m, 2H), 3.09-2.82 (m, 2H), 2.10-1.73 (m, 6H).

Example 5

Synthesis of 4-{2-[(1,3-dioxo-2-phenyl-2,3-dihydro-1H-isoindol-5-carbonyl)-amino]-ethyl}-4-morpholinium chloride (Compound 5)

1,3-dioxo-2-phenyl-2,3-dihydro-1H-isoindol-5-carboxylic acid (100 mg, 0.374 mmol) and 2-morpholinoethane amine (100 μL, 0.730 mmol) were reacted with each other. Target compound in the amount of 130 mg (84%) was obtained by following the procedure described in Example 1.

$^1$H NMR (400 MHz, DMSO-d$_6$) δ 11.11 (br s, 1H), 9.31 (br s, 1H), 8.43 (s, 1H), 8.42 (d, 1H, J=12.5 Hz), 8.06 (d, 1H, J=7.6 Hz), 8.60-8.32 (m, 5H), 4.07-3.91 (m, 2H), 3.90-3.81 (m, 2H), 3.79-3.68 (m, 2H), 3.37-3.27 (m, 2H), 3.21-3.06 (m, 2H).

Example 6

Synthesis of 4-{3-[(1,3-dioxo-2-phenyl-2,3-dihydro-1H-isoindol-5-carbonyl)-amino]-propyl}-4-morpholinium chloride (Compound 6)

1,3-dioxo-2-phenyl-2,3-dihydro-1H-isoindol-5-carboxylic acid (100 mg, 0.374 mmol) and 3-morpholin-1-yl-propylamine (100 μL, 0.686 mmol) were reacted with each other. Target compound in the amount of 104 mg (65%) was obtained by following the procedure described in Example 1.

$^1$H NMR (400 MHz, DMSO-d$_6$) δ 11.68 (br s, 1H), 9.13 (br s, 1H), 8.40 (s, 1H), 8.37 (d, 1H, J=7.1 Hz), 8.06 (d, 1H, J=7.1 Hz), 7.60-7.38 (m, 5H), 4.02-3.88 (m, 2H), 3.88-3.73 (m, 2H), 3.53-3.39 (m, 2H), 3.21-2.98 (m, 4H), 2.09-1.92 (m, 2H).

Example 7

Synthesis of 1-(2-{[2-(2-fluoro-phenyl)-1,3-dioxo-2,3-dihydro-1H-isoindol-5-carbonyl]-amino}-ethyl)-piperidinium chloride (Compound 7)

2-(2-fluoro-phenyl)-1,3-dioxo-2,3-dihydro-1H-isoindol-5-carboxylic acid (100 mg, 0.351 mmol) and 2-piperidin-2-yl-ethylamine (100 μL, 0.704 mmol) were reacted with each other. Target compound in the amount of 123 mg (81%) was obtained by following the procedure described in Example 1.

$^1$H NMR (400 MHz, DMSO-d$_6$) δ 10.37 (br s, 1H), 9.36 (br s, 1H), 8.46 (s, 1H), 8.43 (d, 1H, J=7.4 Hz), 8.19 (d, 1H, J=7.4 Hz), 7.68-7.50 (m, 2H), 7.45 (t, 1H, J=9.0 Hz), 7.37 (t, 1H, J=7.0 Hz), 3.79-3.62 (m, 2H), 3.58-3.41 (m, 2H), 3.30-3.12 (m, 2H), 2.99-2.78 (m, 2H), 1.88-1.60 (m, 5H), 1.47-1.27 (m, 1H).

Example 8

Synthesis of 1-(3-{[2-(2-fluoro-phenyl)-1,3-dioxo-2,3-dihydro-1H-isoindol-5-carbonyl]-amino}-propyl)-2-methyl-piperidinium chloride (Compound 8)

2-(2-fluoro-phenyl)-1,3-dioxo-2,3-dihydro-1H-isoindol-5-carboxylic acid (100 mg, 0.351 mmol) and 3-(2-methylpiperidin-1-yl)propan-1-amine (100 μL, 0.576 mmol) were reacted with each other. Target compound in the amount of 130 mg (81%) was obtained by following the procedure described in Example 1.

$^1$H NMR (400 MHz, DMSO-d$_6$) δ 10.08 (br s, 0.3H), 10.01 (br s, 0.7H), 9.13 (br s, 1H), 8.44 (s, 1H), 8.40 (d, 1H, J=7.8 Hz), 8.12 (d, 1H, J=7.8 Hz), 7.67-7.51 (m, 2H), 7.48 (t, 1H, J=9.2 Hz), 7.40 (t, 1H, J=7.5 Hz), 3.67-3.53 (m, 0.3H), 3.48-2.99 (m, 6H), 2.99-2.83 (m, 0.7H), 2.04-1.87 (m, 2H), 1.87-1.53 (m, 5H), 1.53-1.38 (m, 1H), 1.29 (d, 2.1H, J=6.3 Hz), 1.23 (d, 0.9H, J=6.8 Hz).

Example 9

Synthesis of 1-(2-{[2-(2-fluoro-phenyl)-1,3-dioxo-2,3-dihydro-1H-isoindol-5-carbonyl]-amino}-ethyl)-pyrrolidinium chloride (Compound 9)

2-(2-fluoro-phenyl)-1,3-dioxo-2,3-dihydro-1H-isoindol-5-carboxylic acid (100 mg, 0.351 mmol) and 2-pyrrolidin-1-yl-ethylamine (100 μL, 0.789 mmol) were reacted with each other. Target compound in the amount of 122 mg (83%) was obtained by following the procedure described in Example 1.

$^1$H NMR (400 MHz, DMSO-d$_6$) δ 10.36 (br s, 1H), 9.26 (br s, 1H), 8.48 (s, 1H), 8.44 (d, 1H, J=7.7 Hz), 8.13 (d, 1H, J=7.7 Hz), 7.68-7.53 (m, 2H), 7.48 (t, 1H, J=9.3 Hz), 7.40 (t, 1H, J=7.6 Hz), 3.78-3.57 (m, 4H), 3.88-3.27 (m, 2H), 3.14-2.96 (m, 2H), 2.10-1.80 (m, 4H).

Example 10

Synthesis of 1-(3-{[2-(2-fluoro-phenyl)-1,3-dioxo-2,3-dihydro-1H-isoindol-5-carbonyl]-amino}-propyl)-pyrrolidinium chloride (Compound 10)

2-(2-fluoro-phenyl)-1,3-dioxo-2,3-dihydro-1H-isoindol-5-carboxylic acid (100 mg, 0.351 mmol) and 3-pyrrolidin-1-yl-propylamine (100 μL, 0.772 mmol) were reacted with each other. Target compound in the amount of 93 mg (61%) was obtained by following the procedure described in Example 1.

$^1$H NMR (400 MHz, DMSO-d$_6$) δ 10.49 (br s, 1H), 9.11 (t, 1H, J=5.3 Hz), 8.45 (s, 1H), 8.40 (d, 1H, J=7.7 Hz), 8.12 (d, 1H, J=7.7 Hz), 7.64-7.51 (m, 2H), 7.48 (t, 1H, J=9.2 Hz), 7.40 (t, 1H, J=7.5 Hz), 3.60-3.46 (m, 2H), 3.46-3.33 (m, 2H), 3.22-3.09 (m, 2H), 3.04-2.84 (m, 2H), 2.06-1.78 (m, 6H).

Example 11

Synthesis of 4-(2-{[2-(2-fluoro-phenyl)-1,3-dioxo-2,3-dihydro-1H-isoindol-5-carbonyl]-amino}-ethyl)-4-morpholinium chloride (Compound 11)

2-(2-fluoro-phenyl)-1,3-dioxo-2,3-dihydro-1H-isoindol-5-carboxylic acid (100 mg, 0.351 mmol) and 2-morpholinoethane amine (100 μL, 0.730 mmol) were reacted with each other. Target compound in the amount of 136 mg (89%) was obtained by following the procedure described in Example 1.

$^1$H NMR (400 MHz, DMSO-d$_6$) δ 10.69 (br s, 1H), 9.27 (br s, 1H), 8.48 (s, 1H), 8.44 (d, 1H, J=7.8 Hz), 8.14 (d, 1H, J=7.8 Hz), 7.65-7.51 (m, 2H), 7.48 (t, 1H, J=9.1 Hz), 7.40 (t, 1H, J=7.5 Hz), 4.07-3.93 (m, 2H), 3.89-2.68 (m, 4H), 3.61-3.50 (m, 2H), 3.42-3.31 (m, 2H), 3.22-3.07 (m, 2H).

Example 12

Synthesis of 4-(3-{[2-(2-fluoro-phenyl)-1,3-dioxo-2,3-dihydro-1H-isoindol-5-carbonyl]-amino}-propyl)-4-morpholinium chloride (Compound 12)

2-(2-fluoro-phenyl)-1,3-dioxo-2,3-dihydro-1H-isoindol-5-carboxylic acid (100 mg, 0.351 mmol) and 3-morpholin-1-yl-propylamine (100 μL, 0.686 mmol) were reacted with each other. Target compound in the amount of 117 mg (74%) was obtained by following the procedure described in Example 1.

$^1$H NMR (400 MHz, DMSO-d$_6$) δ 10.87 (br s, 1H), 9.13 (br s, 1H), 8.44 (s, 1H), 8.40 (d, 1H, J=7.7 Hz), 8.12 (d, 1H, J=7.7 Hz), 7.64-7.50 (m, 2H), 7.48 (t, 1H, J=9.3 Hz), 7.40 (t, 1H, J=7.5 Hz), 4.00-3.88 (m, 2H), 3.86-3.70 (m, 2H), 3.50-3.32 (m, 4H), 3.22-2.98 (m, 4H), 2.10-1.91 (m, 2H).

Example 13

Synthesis of 1-(2-{[2-(3-fluoro-phenyl)-1,3-dioxo-2,3-dihydro-1H-isoindol-5-carbonyl]-amino}-ethyl)-piperidinium chloride (Compound 13)

2-(3-fluoro-phenyl)-1,3-dioxo-2,3-dihydro-1H-isoindol-5-carboxylic acid (100 mg, 0.351 mmol) and 2-piperidin-2-yl-ethylamine (100 μL, 0.704 mmol) were reacted with each other. Target compound in the amount of 75 mg (50%) was obtained by following the procedure described in Example 1.

$^1$H NMR (400 MHz, DMSO-d$_6$) δ 10.34 (br s, 1H), 9.34 (br s, 1H), 8.44 (s, 1H), 8.42 (d, 1H, J=8.2 Hz), 8.07 (d, 1H, J=7.6 Hz), 7.58 (q, 1H, J=11.2 Hz), 7.41-7.21 (m, 3H), 3.78-3.67 (m, 2H), 3.58-3.42 (m, 2H), 3.29-3.16 (m, 2H), 2.99-2.80 (m, 2H), 1.90-1.61 (m, 5H), 1.48-1.29 (m, 1H).

Example 14

Synthesis of 1-(3-{[2-(3-fluoro-phenyl)-1,3-dioxo-2,3-dihydro-1H-isoindol-5-carbonyl]-amino}-propyl)-2-methyl-piperidinium chloride (Compound 14)

2-(3-fluoro-phenyl)-1,3-dioxo-2,3-dihydro-1H-isoindol-5-carboxylic acid (100 mg, 0.351 mmol) and 3-(2-methylpiperidin-1-yl)propan-1-amine (100 μL, 0.576 mmol) were reacted with each other. Target compound in the amount of 23 mg (14%) was obtained by following the procedure described in Example 1.

$^1$H NMR (400 MHz, DMSO-d$_6$) δ 10.00 (br s, 0.3H), 9.91 (br s, 0.7H), 9.13 (br s, 1H), 8.42 (s, 1H), 8.38 (d, 1H, J=7.6 Hz), 8.10 (d, 1H, J=7.7 Hz), 7.60 (q, 1H, J=7.0 Hz), 7.44-7.26 (m, 3H), 3.69-3.57 (m, 0.3H), 3.44-3.00 (m, 6H), 3.00-2.85 (m, 0.7H), 2.04-1.88 (m, 2H), 1.88-1.50 (m, 5H), 1.50-1.33 (m, 1H), 1.29 (d, 2.1H, J=6.1 Hz), 1.24 (d, 0.9H, 6.5 Hz).

Example 15

Synthesis of 1-(2-{[2-(3-fluoro-phenyl)-1,3-dioxo-2,3-dihydro-1H-isoindol-5-carbonyl]-amino}-ethyl)-pyrrolidinium chloride (Compound 15)

2-(3-fluoro-phenyl)-1,3-dioxo-2,3-dihydro-1H-isoindol-5-carboxylic acid (100 mg, 0.351 mmol) and 2-pyrrolidin-1-yl-ethylamine (100 µL, 0.789 mmol) were reacted with each other. Target compound in the amount of 99 mg (68%) was obtained by following the procedure described in Example 1.

$^1$H NMR (400 MHz, DMSO-$d_6$) δ 10.43 (br s, 1H), 9.27 (t, 1H, J=5.1 Hz), 8.46 (s, 1H), 8.43 (d, 1H, J=7.8 Hz), 8.11 (d, 1H, J=7.7 Hz), 7.61 (q, 1H, J=7.6 Hz), 7.46-7.26 (m, 3H), 3.79-3.59 (m, 4H), 3.47-3.32 (m, 2H), 3.16-3.00 (m, 2H), 2.12-1.79 (m, 4H).

Example 16

Synthesis of 1-(3-{[2-(3-fluoro-phenyl)-1,3-dioxo-2,3-dihydro-1H-isoindol-5-carbonyl]-amino}-propyl)-pyrrolidinium chloride (Compound 16)

2-(3-fluoro-phenyl)-1,3-dioxo-2,3-dihydro-1H-isoindol-5-carboxylic acid (100 mg, 0.351 mmol) and 3-pyrrolidin-1-yl-propylamine (100 µL, 0.772 mmol) were reacted with each other. Target compound in the amount of 63 mg (42%) was obtained by following the procedure described in Example 1.

$^1$H NMR (400 MHz, DMSO-$d_6$) δ 10.54 (br s, 1H), 9.11 (br s, 1H), 8.42 (s, 1H), 8.39 (d, 1H, J=7.7 Hz), 8.10 (d, 1H, J=7.6 Hz), 7.60 (q, 1H, J=7.0 Hz), 7.49-7.26 (m, 3H), 3.65-3.50 (m, 2H), 3.50-3.32 (m, 2H), 3.24-3.13 (m, 2H), 3.08-2.90 (m, 2H), 2.12-1.79 (m, 6H).

Example 17

Synthesis of 4-(2-{[2-(3-fluoro-phenyl)-1,3-dioxo-2,3-dihydro-1H-isoindol-5-carbonyl]-amino}-ethyl)-4-morpholinium chloride (Compound 17)

2-(3-fluoro-phenyl)-1,3-dioxo-2,3-dihydro-1H-isoindol-5-carboxylic acid (100 mg, 0.351 mmol) and 2-morpholinoethane amine (100 µL, 0.730 mmol) were reacted with each other. Target compound in the amount of 69 mg (45%) was obtained by following the procedure described in Example 1.

$^1$H NMR (400 MHz, DMSO-$d_6$) δ 10.26 (br s, 1H), 9.21 (br s, 1H), 8.43 (s, 1H), 8.39 (d, 1H, J=7.8 Hz), 8.11 (d, 1H, J=7.8 Hz), 7.60 (q, 1H, J=7.6 Hz), 7.42-7.24 (m, 3H), 4.08-3.92 (m, 2H), 3.80-3.66 (m, 4H), 3.61-3.50 (m, 2H), 3.41-3.29 (m, 2H), 3.22-3.06 (m, 2H).

Example 18

Synthesis of 4-(3-{[2-(3-fluoro-phenyl)-1,3-dioxo-2,3-dihydro-1H-isoindol-5-carbonyl]-amino}-propyl)-4-morpholinium chloride (Compound 18)

2-(3-fluoro-phenyl)-1,3-dioxo-2,3-dihydro-1H-isoindol-5-carboxylic acid (100 mg, 0.351 mmol) and 3-morpholin-1-yl-propylamine (100 µL, 0.686 mmol) were reacted with each other. Target compound in the amount of 90 mg (57%) was obtained by following the procedure described in Example 1.

$^1$H NMR (400 MHz, DMSO-$d_6$) δ 10.47 (br s, 1H), 9.11 (br s, 1H), 8.42 (s, 1H), 8.38 (d, 1H, J=7.7 Hz), 8.11 (d, 1H, J=7.7 Hz), 7.61 (q, 1H, J=6.6 Hz), 7.43-7.28 (m, 3H), 4.04-3.89 (m, 2H), 3.82-3.66 (m, 2H), 3.47-3.32 (m, 4H), 3.21-3.14 (m, 2H), 3.14-2.96 (m, 2H), 2.05-1.62 (m, 2H).

Example 19

Synthesis of 1-(2-{[2-(4-fluoro-phenyl)-1,3-dioxo-2,3-dihydro-1H-isoindol-5-carbonyl]-amino}-ethyl)-piperidinium chloride (Compound 19)

2-(4-fluoro-phenyl)-1,3-dioxo-2,3-dihydro-1H-isoindol-5-carboxylic acid (100 mg, 0.351 mmol) and 2-piperidin-2-yl-ethylamine (100 µL, 0.704 mmol) were reacted with each other. Target compound in the amount of 131 mg (86%) was obtained by following the procedure described in Example 1.

$^1$H NMR (400 MHz, DMSO-$d_6$) δ 10.40 (br s, 1H), 9.34 (br s, 1H), 8.42 (s, 1H), 8.40 (d, 1H, J=9.6 Hz), 8.05 (d, 1H, J=7.3 Hz), 7.57-7.42 (m, 2H), 7.37 (t, 2H, J=8.2 Hz), 3.81-3.66 (m, 2H), 3.60-3.43 (m, 2H), 3.30-3.15 (m, 2H), 2.99-2.80 (m, 2H), 1.90-1.60 (m, 5H), 1.48-1.29 (m, 2H).

Example 20

Synthesis of 1-(3-{[2-(4-fluoro-phenyl)-1,3-dioxo-2,3-dihydro-1H-isoindol-5-carbonyl]-amino}-propyl)-2-methyl-piperidinium chloride (Compound 20)

2-(4-fluoro-phenyl)-1,3-dioxo-2,3-dihydro-1H-isoindol-5-carboxylic acid (100 mg, 0.351 mmol) and 3-(2-methylpiperidin-1-yl)propan-1-amine (100 µL, 0.576 mmol) were reacted with each other. Target compound in the amount of 50 mg (31%) was obtained by following the procedure described in Example 1.

$^1$H NMR (300 MHz, DMSO-$d_6$) δ 9.90 (br s, 1H), 9.11 (br s, 1H), 8.40 (s, 1H), 8.36 (d, 1H, J=7.6 Hz), 8.08 (d, 1H, J=7.7 Hz), 7.55-7.42 (m, 2H), 7.39 (t, 1H, J=8.7 Hz), 3.66-3.52 (m, 0.3H), 3.47-2.81 (m, 6.7H), 2.04-1.87 (m, 2H), 1.87-1.35 (m, 6H), 1.28 (d, 2.1H, J=5.9 Hz), 1.23 (d, 0.9H, J=7.0 Hz).

Example 21

Synthesis of 1-(2-{[2-(4-fluoro-phenyl)-1,3-dioxo-2,3-dihydro-1H-isoindol-5-carbonyl]-amino}-ethyl)-pyrrolidinium chloride (Compound 21)

2-(4-fluoro-phenyl)-1,3-dioxo-2,3-dihydro-1H-isoindol-5-carboxylic acid (100 mg, 0.351 mmol) and 2-pyrrolidin-1-yl-ethylamine (100 µL, 0.789 mmol) were reacted with each other. Target compound in the amount of 90 mg (61%) was obtained by following the procedure described in Example 1.

$^1$H NMR (300 MHz, DMSO-$d_6$) δ 10.35 (br s, 1H), 9.23 (br s, 1H), 8.44 (s, 1H), 8.41 (d, 1H, J=7.8 Hz), 8.09 (d, 1H, J=7.7 Hz), 7.52 (dd, 2H, J=8.8, 5.2 Hz), 7.39 (t, 1H, J=8.8 Hz), 3.57-3.54 (m, 4H), 3.41-3.23 (m, 2H), 3.13-3.91 (m, 2H), 2.10-1.77 (m, 4H).

Example 22

Synthesis of 1-(3-{[2-(4-fluoro-phenyl)-1,3-dioxo-2,3-dihydro-1H-isoindol-5-carbonyl]-amino}-propyl)-pyrrolidinium chloride (Compound 22)

2-(4-fluoro-phenyl)-1,3-dioxo-2,3-dihydro-1H-isoindol-5-carboxylic acid (100 mg, 0.351 mmol) and 3-pyrrolidin-1-yl-propylamine (100 µL, 0.772 mmol) were reacted with each other. Target compound in the amount of 110 mg (73%) was obtained by following the procedure described in Example 1.

$^1$H NMR (300 MHz, DMSO-$d_6$) δ 10.32 (br s, 1H), 9.07 (br s, 1H), 8.40 (s, 1H), 8.37 (d, 1H, J=8.4 Hz), 8.08 (d, 1H, J=7.8 Hz), 7.52 (dd, 2H, J=8.7, 5.1 Hz), 7.39 (t, 1H, J=8.8 Hz), 3.59-3.26 (m, 4H), 3.19-3.06 (m, 2H), 3.06-2.84 (m, 2H), 2.06-1.80 (m, 6H).

Example 23

Synthesis of 4-(2-{[2-(4-fluoro-phenyl)-1,3-dioxo-2,3-dihydro-1H-isoindol-5-carbonyl]-amino}-ethyl)-4-morpholinium chloride (Compound 23)

2-(4-fluoro-phenyl)-1,3-dioxo-2,3-dihydro-1H-isoindol-5-carboxylic acid (100 mg, 0.351 mmol) and 2-morpholinoethane amine (100 µL, 0.730 mmol) were reacted with each other. Target compound in the amount of 105 mg (67%) was obtained by following the procedure described in Example 1.

$^1$H NMR (400 MHz, DMSO-$d_6$) δ 10.65 (br s, 1H), 9.27 (br s, 1H), 8.44 (s, 1H), 8.41 (d, 1H, J=7.8 Hz), 8.10 (d, 1H, J=7.7 Hz), 7.53 (dd, 2H, J=8.9, 5.1 Hz), 7.40 (t, 1H, J=8.8 Hz), 4.07-3.94 (m, 2H), 3.87-3.68 (m, 4H), 3.63-3.50 (m, 2H), 3.42-3.26 (m, 2H), 3.21-3.05 (m, 2H).

Example 24

Synthesis of 4-(3-{[2-(4-fluoro-phenyl)-1,3-dioxo-2,3-dihydro-1H-isoindol-5-carbonyl]-amino}-propyl)-4-morpholinium chloride (Compound 24)

2-(4-fluoro-phenyl)-1,3-dioxo-2,3-dihydro-1H-isoindol-5-carboxylic acid (100 mg, 0.351 mmol) and 3-morpholin-1-yl-propylamine (100 µL, 0.686 mmol) were reacted with each other. Target compound in the amount of 120 mg (76%) was obtained by following the procedure described in Example 1.

$^1$H NMR (400 MHz, DMSO-$d_6$) δ 10.60 (br s, 1H), 9.10 (t, 1H, J=5.2 Hz), 8.40 (s, 1H), 8.37 (d, 1H, J=7.7 Hz), 8.08 (d, 1H, J=7.8 Hz), 7.52 (dd, 2H, J=8.8, 5.1 Hz), 7.39 (t, 1H, J=8.8 Hz), 4.02-3.88 (m, 2H), 3.82-3.67 (m, 2H), 3.48-3.30 (m, 4H), 3.21-2.97 (m, 4H), 2.08-1.92 (m, 2H).

Example 25

Synthesis of 1-(2-{[2-(2-chloro-phenyl)-1,3-dioxo-2,3-dihydro-1H-isoindol-5-carbonyl]-amino}-ethyl)-piperidinium chloride (Compound 25)

2-(2-chloro-phenyl)-1,3-dioxo-2,3-dihydro-1H-isoindol-5-carboxylic acid (100 mg, 0.331 mmol) and 2-piperidin-2-yl-ethylamine (52 µL, 0.364 mmol) were reacted with each other. Target compound in the amount of 31 mg (21%) was obtained by following the procedure described in Example 1.

$^1$H NMR (400 MHz, CDCl$_3$) δ 11.61 (br s, 1H), 9.48 (br s, 1H), 8.66 (s, 2H), 8.05 (s, 1H), 7.58 (s, 1H), 7.56-7.33 (m, 4H), 3.99 (br s, 2H), 3.69 (br s, 2H), 2.77 (br s, 2H), 2.34 (br s, 2H), 2.08-1.46 (m, 6H).

Example 26

Synthesis of 1-(2-{[2-(3-chloro-phenyl)-1,3-dioxo-2,3-dihydro-1H isoindol-5-carbonyl]-amino}-ethyl)-piperidinium chloride (Compound 26)

2-(3-chloro-phenyl)-1,3-dioxo-2,3-dihydro-1H-isoindol-5-carboxylic acid (100 mg, 0.331 mmol) and 2-piperidin-2-yl-ethylamine (52 µL, 0.364 mmol) were reacted with each other. Target compound in the amount of 49 mg (33%) was obtained by following the procedure described in Example 1.

$^1$H NMR (400 MHz, CDCl$_3$) δ 11.75 (br s, 1H), 9.51 (s, 1H), 8.67 (s, 2H), 8.06 (d, 1H, J=7.5 Hz), 7.61-7.36 (m, 4H), 3.99 (br s, 2H), 3.68 (br s, 2H), 3.29 (br s, 2H), 2.75 (br s, 2H), 2.35 (br s, 2H), 2.05-1.68 (m, 4H).

Example 27

Synthesis of 1-(2-{[2-(4-chloro-phenyl)-1,3-dioxo-2,3-dihydro-1H-isoindol-5-carbonyl]-amino}-ethyl)-piperidinium chloride (Compound 27)

2-(4-chloro-phenyl)-1,3-dioxo-2,3-dihydro-1H-isoindol-5-carboxylic acid (100 mg, 0.331 mmol) and 2-piperidin-2-yl-ethylamine (52 µL, 0.364 mmol) were reacted with each other. Target compound in the amount of 55 mg (37%) was obtained by following the procedure described in Example 1.

$^1$H NMR (400 MHz, DMSO-$d_6$) δ 10.37 (br s, 1H), 9.34 (t, 1H, J=5.2 Hz), 8.44-8.40 (m, 2H), 8.06 (d, 1H, J=7.7 Hz), 7.61 (d, 2H, J=8.7 Hz), 7.50 (d, 2H, J=8.7 Hz), 3.80-3.69 (m, 2H), 3.58-3.44 (m, 2H), 3.32-3.21 (m, 2H), 2.98-2.80 (m, 2H), 1.90-1.61 (m, 5H), 1.56-1.23 (m, 1H).

Example 28

Synthesis of 1-{2-[(1,3-dioxo-2-o-tolyl-2,3-dihydro-1H-isoindol-5-carbonyl)-amino]-ethyl}-piperidinium chloride (Compound 28)

(1,3-dioxo-2-o-tolyl-2,3-dihydro-1H-isoindol-5-carboxylic acid (100 mg, 0.355 mmol) and 2-piperidin-2-yl-ethylamine (56 µL/0.391 mmol) were reacted with each other. Target compound in the amount of 44 mg (29%) was obtained by following the procedure described in Example 1.

$^1$H NMR (400 MHz, CDCl$_3$) δ 11.69 (br s, 1H), 9.47 (br s, 1H), 8.64 (br s, 2H), 8.04 (br s, 1H), 7.47-7.31 (m, 4H), 7.23-7.11 (m, 1H), 4.00 (br s, 2H), 3.69 (br s, 2H), 3.32 (br s, 2H), 2.78 (br s, 2H), 2.36 (br s, 2H), 1.95 (br s, 6H).

Example 29

Synthesis of 1-{3-[(1,3-dioxo-2-o-tolyl-2,3-dihydro-1H-isoindol-5-carbonyl)-amino]-propyl}-2-methyl-piperidinium chloride (Compound 29)

(1,3-dioxo-2-o-tolyl-2,3-dihydro-1H-isoindol-5-carboxylic acid (100 mg, 0.355 mmol) and 3-(2-methylpiperidin-1-yl)propan-1-amine (124 mL, 0.711 mmol) were reacted with each other. Target compound in the amount of 63 mg (40%) was obtained by following the procedure described in Example 1.

$^1$H NMR (400 MHz, DMSO-$d_6$) δ 9.69 (br s, 0.3H), 9.57 (br s, 0.7H), 9.08 (t, 1H, J=5.2 Hz), 8.40 (s, 1H), 8.36 (d, 1H, J=7.8 Hz), 8.09 (d, 1H, J=7.8 Hz), 7.49-7.29 (m, 4H), 3.66-3.54 (m, 0.3H), 3.43-2.99 (m, 6H), 2.99-2.87 (m, 0.7H), 2.12 (s, 3H), 2.02-1.89 (m, 2H), 1.89-1.40 (m, 6H), 1.27 (d, 2.1H, 6.3 Hz), 1.22 (d, 0.9H, J=6.9 Hz).

Example 30

Synthesis of 1-{2-[(1,3-dioxo-2-o-tolyl-2,3-dihydro-1H-isoindol-5-carbonyl)-amino]-ethyl}-pyrrolidinium chloride (Compound 30)

(1,3-dioxo-2-o-tolyl-2,3-dihydro-1H-isoindol-5-carboxylic acid (100 mg, 0.355 mmol) and 2-pyrrolidin-1-yl-ethylamine (90 μL, 0.711 mmol) were reacted with each other. Target compound in the amount of 75 mg (51%) was obtained by following the procedure described in Example 1.

$^1$H NMR (400 MHz, DMSO-$d_6$) δ 10.00 (br s, 1H), 9.19 (t, 1H, J=5.2 Hz), 8.46 (s, 1H), 8.41 (d, 1H, J=7.8 Hz), 8.12 (d, 1H, J=7.8 Hz), 7.48-7.28 (m, 4H), 3.72-3.54 (m, 4H), 3.43-3.28 (m, 2H), 3.13-2.91 (m, 2H), 2.14 (s, 3H), 2.02-1.74 (m, 2H).

Example 31

Synthesis of 1-{3-[(1,3-dioxo-2-o-tolyl-2,3-dihydro-1H-isoindol-5-carbonyl)-amino]-propyl}-pyrrolidinium chloride (Compound 31)

(1,3-dioxo-2-o-tolyl-2,3-dihydro-1H-isoindol-5-carboxylic acid (100 mg, 0.355 mmol) and 3-pyrrolidin-1-yl-propylamine (90 μL, 0.711 mmol) were reacted with each other. Target compound in the amount of 24 mg (15%) was obtained by following the procedure described in Example 1.

$^1$H NMR (400 MHz, DMSO-$d_6$) δ 10.75 (br s, 1H), 9.12-9.02 (m, 1H), 8.42-8.31 (m, 2H), 8.07 (d, 1H, J=7.7 Hz), 7.39-7.11 (m, 4H), 3.50 (d, 2H, J=5.1 Hz), 3.39 (d, 2H, J=6.5 Hz), 3.18-3.05 (m, 2H), 3.00-2.81 (m, 2H), 2.11 (s, 3H), 1.97-1.68 (m, 6H).

Example 32

Synthesis of 4-{2-[(1,3-dioxo-2-o-tolyl-2,3-dihydro-1H-isoindol-5-carbonyl)-amino]-ethyl}-4-morpholinium chloride (Compound 32)

(1,3-dioxo-2-o-tolyl-2,3-dihydro-1H-isoindol-5-carboxylic acid (100 mg, 0.355 mmol) and 2-morpholinoethaneamine (93 μL, 0.711 mmol) were reacted with each other. Target compound in the amount of 151 mg (99%) was obtained by following the procedure described in Example 1.

$^1$H NMR (400 MHz, DMSO-$d_6$) δ 10.01 (br s, 1H), 9.18 (br s, 1H), 8.43 (s, 1H), 8.39 (d, 1H, J=7.6 Hz), 8.12 (d, 1H, J=7.6 Hz), 7.47-7.30 (m, 4H), 4.06-3.96 (m, 2H), 3.78-3.65 (m, 4H), 3.60-3.51 (m, 2H), 3.41-3.30 (m, 2H), 3.21-3.09 (m, 2H), 2.13 (s, 3H).

Example 33

Synthesis of 1-{2-[(1,3-dioxo-2-m-tolyl-2,3-dihydro-1H-isoindol-5-carbonyl)-amino]-ethyl}-piperidinium chloride (Compound 33)

(1,3-dioxo-2-m-tolyl-2,3-dihydro-1H-isoindol-5-carboxylic acid (100 mg, 0.355 mmol) and 2-piperidin-2-yl-ethylamine (101 μL, 0.711 mmol) were reacted with each other. Target compound in the amount of 66 mg (44%) was obtained by following the procedure described in Example 1.

$^1$H NMR (400 MHz, DMSO-$d_6$) δ 9.65 (br s, 1H), 9.23 (br s, 1H), 8.42 (s, 1H), 8.39 (d, 1H, J=7.8 Hz), 8.09 (d, 1H, J=7.7 Hz), 7.43 (t, 1H, J=8.0 Hz), 7.32-7.28 (m, 3H), 3.78-3.67 (m, 2H), 3.61-3.50 (m, 2H), 3.32-3.21 (m, 2H), 3.01-2.88 (m, 2H), 2.38 (s, 3H), 1.89-1.64 (m, 5H), 1.48-1.32 (m, 1H).

Example 34

Synthesis of 1-{3-[(1,3-dioxo-2-m-tolyl-2,3-dihydro-1H-isoindol-5-carbonyl)-amino]-propyl}-2-methyl-piperidinium chloride (Compound 34)

(1,3-dioxo-2-m-tolyl-2,3-dihydro-1H-isoindol-5-carboxylic acid (100 mg, 0.355 mmol) and 3-(2-methylpiperidin-1-yl)propan-1-amine (124 μL, 0.711 mmol) were reacted with each other. Target compound in the amount of 79 mg (50%) was obtained by following the procedure described in Example 1.

$^1$H NMR (400 MHz, DMSO-$d_6$) δ 10.38 (br s, 1H), 9.19-9.11 (m, 1H), 8.41-8.31 (m, 2H), 8.05 (d, 1H, J=7.6 Hz), 7.43-7.35 (m, 1H), 7.30-7.19 (m, 4H), 3.63-3.51 (m, 0.3H), 3.48-3.23 (m, 3H), 3.28-2.98 (m, 4H), 2.98-2.81 (m, 0.7H), 2.35 (s, 3H), 2.05-1.35 (m, 7H), 1.52-1.38 (m, 1H), 1.28 (d, 2.1H, J=6.2 Hz), 1.22 (d, 0.9H, J=6.6 Hz).

Example 35

Synthesis of 1-{2-[(1,3-dioxo-2-m-tolyl-2,3-dihydro-1H-isoindol-5-carbonyl)-amino]-ethyl}-pyrrolidinium chloride (Compound 35)

(1,3-dioxo-2-m-tolyl-2,3-dihydro-1H-isoindol-5-carboxylic acid (100 mg, 0.355 mmol) and 2-pyrrolidin-1-yl-ethylamine (90 μL, 0.711 mmol) were reacted with each other. Target compound in the amount of 93 mg (63%) was obtained by following the procedure described in Example 1.

$^1$H NMR (400 MHz, DMSO-$d_6$) δ 10.66 (br s, 1H), 9.26 (s, 1H), 8.50-8.33 (m, 2H), 8.03 (d, 1H, J=7.1 Hz), 7.48-7.12 (m, 4H), 3.78-3.41 (m, 6H), 3.13-2.91 (m, 2H), 2.34 (s, 3H), 2.08-1.76 (m, 4H).

Example 36

Synthesis of 1-{3-[(1,3-dioxo-2-m-tolyl-2,3-dihydro-1H-isoindol-5-carbonyl)-amino]-propyl}-pyrrolidinium chloride (Compound 36)

(1,3-dioxo-2-m-tolyl-2,3-dihydro-1H-isoindol-5-carboxylic acid (100 mg, 0.355 mmol) and 3-pyrrolidin-1-yl-propylamine (90 μL, 0.711 mmol) were reacted with each other. Target compound in the amount of 96 mg (63%) was obtained by following the procedure described in Example 1.

¹H NMR (400 MHz, DMSO-d₆) δ 10.75 (br s, 1H), 9.12-9.02 (m, 1H), 8.42-8.31 (m, 2H), 8.05 (d, 1H, J=7.7 Hz), 7.43-7.32 (m, 2H), 7.28-7.13 (m, 2H), 3.52-3.41 (m, 2H), 3.39-2.29 (m, 2H), 3.20-3.03 (m, 2H), 3.00-2.81 (m, 2H), 2.36 (s, 3H), 2.04-1.71 (m, 6H)

Example 37

Synthesis of 4-{2-[(1,3-dioxo-2-m-tolyl-2,3-dihydro-1H-isoindol-5-carbonyl)-amino]-ethyl}-4-morpholinium chloride (Compound 37)

(1,3-dioxo-2-m-tolyl-2,3-dihydro-1H-isoindol-5-carboxylic acid (100 mg, 0.355 mmol) and 2-morpholinoethane amine (93 μL, 0.711 mmol) were reacted with each other. Target compound in the amount of 17 mg (11%) was obtained by following the procedure described in Example 1.

¹H NMR (400 MHz, DMSO-d₆) δ 10.44 (br s, 1H), 9.22 (br s, 1H), 8.41 (s, 1H), 8.39 (d, 1H, J=7.8 Hz), 8.08 (d, 1H, J=7.8 Hz), 7.41 (t, 1H, J=7.9 Hz), 7.33-7.20 (m, 3H), 4.08-3.92 (m, 2H), 3.84-3.64 (m, 4H), 3.64-3.50 (m, 2H), 3.42-3.29 (m, 2H), 3.22-3.07 (m, 2H), 2.31 (s, 3H).

Example 38

Synthesis of 4-{3-[(1,3-dioxo-2-m-tolyl-2,3-dihydro-1H-isoindol-5-carbonyl)-amino]-propyl}-4-morpholinium chloride (Compound 38)

(1,3-dioxo-2-m-tolyl-2,3-dihydro-1H-isoindol-5-carboxylic acid (100 mg, 0.355 mmol) and 3-morpholin-1-yl-propylamine (104 μL, 0.711 mmol) were reacted with each other. Target compound in the amount of 143 mg (90%) was obtained by following the procedure described in Example 1.

¹H NMR (400 MHz, DMSO-d₆) δ 10.13 (br s, 1H), 9.19 (t, 1H, J=5.3 Hz), 8.44-8.31 (m, 2H), 8.07 (d, 1H, J=7.8 Hz), 7.41 (t, 1H, J=8.0 Hz), 7.33 (s, 4H), 3.76-3.53 (m, 4H), 3.45-3.28 (m, 2H), 3.16-2.93 (m, 2H), 2.37 (s, 3H), 2.10-1.80 (m, 4H).

Example 39

Synthesis of 1-{2-[(1,3-dioxo-2-p-tolyl-2,3-dihydro-1H-isoindol-5-carbonyl)-amino]-ethyl}-piperidinium chloride (Compound 39)

2-(4-methyl-phenyl)-1,3-dioxo-2,3-dihydro-1H-isoindol-5-carboxylic acid (100 mg, 0.355 mmol) and 2-piperidin-1-yl-ethylamine (56 μL, 0.391 mmol) were reacted with each other. Target compound in the amount of 38 mg (25%) was obtained by following the procedure described in Example 1.

¹H NMR (400 MHz, DMSO-d₆) δ 9.58 (br s, 1H), 9.20 (br s, 1H), 8.40 (s, 1H), 8.37 (d, 1H, J=8.9 Hz), 8.07 (d, 1H, J=7.8 Hz), 7.33 (s, 4H), 3.77-3.63 (m, 2H), 3.60-3.49 (m, 2H), 3.39-3.18 (m, 2H), 3.01-2.82 (m, 2H), 2.37 (s, 3H), 1.90-1.62 (m, 5H), 1.49-1.31 (m, 1H).

Example 40

Synthesis of 1-{3-[(1,3-dioxo-2-p-tolyl-2,3-dihydro-1H-isoindol-5-carbonyl)-amino]-propyl}-2-methyl-piperidinium chloride (Compound 40)

(1,3-dioxo-2-p-tolyl-2,3-dihydro-1H-isoindol-5-carboxylic acid (100 mg, 0.355 mmol) and 3-(2-methylpiperidin-1-yl)propan-1-amine (124 μL, 0.711 mmol) were reacted with each other. Target compound in the amount of 98 mg (62%) was obtained by following the procedure described in Example 1.

¹H NMR (400 MHz, DMSO-d₆) δ 9.82-9.60 (m, 1H), 9.12-9.00 (m, 1H), 8.39-8.25 (m, 2H), 8.07 (q, 1H, J=7.1 Hz), 7.32 (s, 4H), 3.68-3.59 (m, 0.3H), 3.52-3.39 (m, 3H), 3.31-2.98 (m, 4H), 2.98-2.81 (m, 0.7H), 2.36 (s, 3H), 2.08-1.32 (m, 8H), 1.27 (d, 2.1H, J=6.3 Hz), 1.22 (d, 0.9H, J=6.8 Hz).

Example 41

Synthesis of 1-{2-[(1,3-dioxo-2-p-tolyl-2,3-dihydro-1H-isoindol-5-carbonyl)-amino]-ethyl}-pyrrolidinium chloride (Compound 41)

(1,3-dioxo-2-p-tolyl-2,3-dihydro-1H-isoindol-5-carboxylic acid (100 mg, 0.355 mmol) and 2-pyrrolidin-1-yl-ethylamine (90 μL, 0.711 mmol) were reacted with each other. Target compound in the amount of 71 mg (48%) was obtained by following the procedure described in Example 1.

¹H NMR (400 MHz, DMSO-d₆) δ 10.51 (br s, 1H), 9.09 (t, 1H, J=5.4 Hz), 8.44-8.31 (m, 2H), 8.06 (d, 1H, J=7.7 Hz), 7.41 (t, 1H, J=8.0 Hz), 7.32-7.28 (m, 3H), 4.03-3.90 (m, 2H), 3.80-3.69 (m, 2H), 3.50-3.31 (m, 4H), 3.21-3.00 (m, 4H), 2.37 (s, 3H), 2.07-1.90 (m, 2H).

Example 42

Synthesis of 1-(3-{[2-(2-methoxy-phenyl)-1,3-dioxo-2,3-dihydro-1H-isoindol-5-carbonyl]-amino}-propyl)-2-methyl-piperidinium chloride (Compound 42)

2-(2-methoxy-phenyl)-1,3-dioxo-2,3-dihydro-1H-isoindol-5-carboxylic acid (100 mg, 0.336 mmol) and 3-(2-methylpiperidin-1-yl)propan-1-amine (147 μL, 0.841 mmol) were reacted with each other. Target compound in the amount of 129 mg (81%) was obtained by following the procedure described in Example 1.

¹H NMR (400 MHz, DMSO-d₆) δ 9.82 (br s, 0.3H), 9.73 (br s, 0.7H), 9.09 (t, 1H, J=5.1 Hz), 8.39 (s, 1H), 8.35 (d, 1H, J=7.8 Hz), 8.07 (d, 1H, J=7.8 Hz), 7.42 (t, 1H, J=7.5 Hz), 7.10-6.99 (m, 3H), 3.78 (s, 3H), 3.65-3.55 (m, 0.3H), 3.44-2.99 (m, 6H), 2.99-2.86 (m, 0.7H), 2.02-1.89 (m, 2H), 1.89-1.51 (m, 5H), 1.51-1.38 (m, 1H), 1.27 (d, 2.1H, 6.3 Hz), 1.22 (d, 0.9H, J=6.9 Hz).

Example 43

Synthesis of 1-(2-{[2-(2-methoxy-phenyl)-1,3-dioxo-2,3-dihydro-1H-isoindol-5-carbonyl]-amino}-ethyl)-pyrrolidinium chloride (Compound 43)

2-(2-methoxy-phenyl)-1,3-dioxo-2,3-dihydro-1H-isoindol-5-carboxylic acid (100 mg, 0.336 mmol) and 2-pyrrolidin-1-yl-ethylamine (107 μL, 0.841 mmol) were reacted with each other. Target compound in the amount of 48 mg (33%) was obtained by following the procedure described in Example 1.

¹H NMR (400 MHz, DMSO-d₆) δ 10.32 (br s, 1H), 9.22 (t, 1H, J=5.3 Hz), 8.43 (s, 1H), 8.39 (d, 1H, J=7.8 Hz), 8.07 (d, 1H, J=7.6 Hz), 7.44 (t, 1H, J=8.0 Hz), 7.11-6.98 (m, 3H), 3.78 (s, 3H), 3.72-3.57 (m, 4H), 3.41-3.30 (m, 2H), 3.31-2.97 (m, 2H), 2.08-1.94 (m, 2H), 1.94-1.81 (m, 2H).

Example 44

Synthesis of 1-(3-{[2-(2-methoxy-phenyl)-1,3-dioxo-2,3-dihydro-1H-isoindol-5-carbonyl]-amino}-propyl)-pyrrolidinium chloride (Compound 44)

2-(2-methoxy-phenyl)-1,3-dioxo-2,3-dihydro-1H-isoindol-5-carboxylic acid (100 mg, 0.336 mmol) and 3-pyrrolidin-1-yl-propylamine (106 µL, 0.841 mmol) were reacted with each other. Target compound in the amount of 129 mg (86%) was obtained by following the procedure described in Example 1.

$^1$H NMR (400 MHz, DMSO-d$_6$) δ 10.18 (br s, 1H), 9.06 (t, 1H, J=5.5 Hz), 8.39 (s, 1H), 8.36 (d, 1H, J=7.8 Hz), 8.06 (d, 1H, J=7.8 Hz), 7.44 (t, 1H, J=7.9 Hz), 7.10-6.99 (m, 3H), 3.78 (s, 3H), 3.59-3.48 (m, 2H), 3.43-3.35 (m, 2H), 3.22-3.13 (m, 2H), 3.03-2.92 (m, 2H), 2.06-1.79 (m, 6H).

Example 45

Synthesis of 4-(3-{[2-(2-methoxy-phenyl)-1,3-dioxo-2,3-dihydro-1H-isoindol-5-carbonyl]-amino}-propyl)-4-morpholinium chloride (Compound 45)

2-(2-methoxy-phenyl)-1,3-dioxo-2,3-dihydro-1H-isoindol-5-carboxylic acid (100 mg, 0.336 mmol) and 3-morpholin-1-yl-propylamine (98 µL, 0.672 mmol) were reacted with each other. Target compound in the amount of 156 mg (100%) was obtained by following the procedure described in Example 1.

$^1$H NMR (400 MHz, DMSO-d$_6$) δ 10.45 (br s, 1H), 9.08 (br s, 1H), 8.39 (s, 1H), 8.36 (d, 1H, J=7.8 Hz), 8.07 (d, 1H, J=7.7 Hz), 7.44 (t, 1H, J=7.9 Hz), 7.09-6.92 (m, 3H), 4.02-3.97 (m, 2H), 3.80-3.65 (m, 2H), 3.78 (s, 3H), 3.50-3.33 (m, 4H), 3.22-3.11 (m, 2H), 3.11-2.95 (m, 2H), 2.06-1.88 (m, 2H).

Example 46

Synthesis of 1-(2-{[2-(3-methoxy-phenyl)-1,3-dioxo-2,3-dihydro-1H-isoindol-5-carbonyl]-amino}-ethyl)-piperidinium chloride (Compound 46)

2-(3-methyl-phenyl)-1,3-dioxo-2,3-dihydro-1H-isoindol-5-carboxylic acid (100 mg, 0.336 mmol) and 2-piperidin-1-yl-ethylamine (58 µL, 0.404 mmol) were reacted with each other. Target compound in the amount of 96 mg (66%) was obtained by following the procedure described in Example 1.

$^1$H NMR (400 MHz, CDCl$_3$) δ 11.75 (br s, 1H), 9.43 (br s, 1H), 8.62 (s, 2H), 8.04 (s, 1H), 7.46 (s, 1H), 7.42-7.23 (m, 1H), 7.07 (t, 2H, J=6.9 Hz), 3.99 (s, 2H), 3.81 (s, 4H), 3.68 (br s, 2H), 3.28 (br s, 2H), 2.76 (br s, 2H), 2.37 (br s, 2H), 1.94 (br s, 3H).

Example 47

Synthesis of 1-(2-{[2-(3-methoxy-phenyl)-1,3-dioxo-2,3-dihydro-1H-isoindol-5-carbonyl]-amino}-propyl)-piperidinium chloride (Compound 47)

2-(3-methoxy-phenyl)-1,3-dioxo-2,3-dihydro-1H-isoindol-5-carboxylic acid (100 mg, 0.336 mmol) and 3-(2-methylpiperidin-1-yl)propan-1-amine (147 µL, 0.841 mmol) were reacted with each other. Target compound in the amount of 158 mg (99%) was obtained by following the procedure described in Example 1.

$^1$H NMR (400 MHz, DMSO-d$_6$) δ 9.77 (br s, 0.3H), 9.67 (br s, 0.7H), 9.07 (t, 1H, J=5.4 Hz), 8.39-8.25 (m, 2H), 8.07 (d, 1H, J=7.7 Hz), 7.50-7.40 (m, 1H), 7.38-7.29 (m, 1H), 7.19-7.10 (m, 1H), 7.08-6.98 (m, 1H), 3.73 (s, 3H), 3.62-3.50 (m, 0.3H), 3.44-2.99 (m, 6H), 2.98-2.78 (m, 0.7H), 2.00-1.89 (m, 2H), 1.89-1.52 (m, 5H), 1.52-1.38 (m, 1H), 1.27 (d, 2.1H, 6.3 Hz), 1.22 (d, 0.9H, J=6.9 Hz).

Example 48

Synthesis of 1-(2-{[2-(4-methoxy-phenyl)-1,3-dioxo-2,3-dihydro-1H-isoindol-5-carbonyl]-amino}-ethyl)-piperidinium chloride (Compound 48)

2-(4-methoxy-phenyl)-1,3-dioxo-2,3-dihydro-1H-isoindol-5-carboxylic acid (100 mg, 0.336 mmol) and 2-piperidin-1-yl-ethylamine (96 µL, 0.672 mmol) were reacted with each other. Target compound in the amount of 71 mg (48%) was obtained by following the procedure described in Example 1.

$^1$H NMR (400 MHz, DMSO-d$_6$) δ 9.80 (br s, 1H), 9.27 (s, 1H), 8.40 (s, 2H), 8.06 (d, 1H, J=6.8 Hz), 7.36 (s, 2H), 7.08 (d, 2H, J=7.5 Hz), 3.81 (s, 3H), 3.70 (s, 2H), 3.60-3.30 (m, 2H), 2.92 (br s, 2H), 1.82-1.36 (m, 6H).

Example 49

Synthesis of 1-{2-[(2-benzyl-1,3-dioxo-2,3-dihydro-1H-isoindol-5-carbonyl)-amino]-ethyl}-piperidinium chloride (Compound 49)

2-benzyl-1,3-dioxo-2,3-dihydro-1H-isoindol-5-carboxylic acid (100 mg, 0.356 mmol) and 2-piperidin-1-yl-ethylamine (100 µL, 0.704 mmol) were reacted with each other. Target compound in the amount of 70 mg (46%) was obtained by following the procedure described in Example 1.

$^1$H NMR (300 MHz, DMSO-d$_6$) δ 9.88 (br s, 1H), 9.22 (br s, 1H), 8.36 (s, 1H), 8.35 (d, 1H, J=8.8 Hz), 8.02 (d, 1H, J=8.3 Hz), 7.40-7.18 (m, 4H), 4.79 (s, 2H), 3.77-3.63 (m, 2H), 3.63-3.41 (m, 2H), 3.31-3.12 (m, 2H), 3.01-2.78 (m, 2H), 1.89-1.58 (m, 5H), 1.51-1.26 (m, 1H).

Example 50

Synthesis of 1-{3-[(2-benzyl-1,3-dioxo-2,3-dihydro-1H-isoindol-5-carbonyl)-amino]-propyl}-2-methyl-piperidinium chloride (Compound 50)

2-benzyl-1,3-dioxo-2,3-dihydro-1H-isoindol-5-carboxylic acid (100 mg, 0.356 mmol) and 3-(2-methylpiperidin-1-yl)propan-1-amine (100 µL, 0.576 mmol) were reacted with each other. Target compound in the amount of 103 mg (63%) was obtained by following the procedure described in Example 1.

$^1$H NMR (400 MHz, DMSO-d$_6$) δ 10.21 (br s, 1H), 9.09 (s, 1H), 8.36 (s, 1H), 8.31 (d, 1H, J=8.0 Hz), 7.99 (d, 1H, J=7.5 Hz), 7.35-7.18 (m, 5H), 4.77 (s, 2H), 3.55 (br s, 0.3H), 3.48-3.34 (m, 2.7H), 3.30-2.95 (m, 3.3H), 2.95-2.80 (m, 0.7H), 2.05-1.50 (m, 7H), 1.50-1.32 (m, 1H), 1.27 (d, 2.1H, J=5.9 Hz), 1.20 (d, 0.9H, J=6.5 Hz).

Example 51

Synthesis of 1-{2-[(2-benzyl-1,3-dioxo-2,3-dihydro-1H-isoindol-5-carbonyl)-amino]-ethyl}-pyrrolidinium chloride (Compound 51)

2-benzyl-1,3-dioxo-2,3-dihydro-1H-isoindol-5-carboxylic acid (100 mg, 0.356 mmol) and 2-pyrrolidin-1-yl-ethylamine (100 μL, 0.789 mmol) were reacted with each other. Target compound in the amount of 85 mg (58%) was obtained by following the procedure described in Example 1.

$^1$H NMR (400 MHz, DMSO-d$_6$) δ 10.36 (br s, 1H), 9.22 (br s, 1H), 8.42-8.29 (m, 2H), 8.02 (d, 1H, J=7.7 Hz), 7.50-7.18 (m, 5H), 4.80 (s, 2H), 3.70-3.55 (m, 4H), 3.40-3.24 (m, 2H), 3.20-2.94 (m, 2H), 2.10-1.80 (m, 4H).

Example 52

Synthesis of 1-{3-[(2-benzyl-1,3-dioxo-2,3-dihydro-1H-isoindol-5-carbonyl)-amino]-propyl}-pyrrolidinium chloride (Compound 52)

2-benzyl-1,3-dioxo-2,3-dihydro-1H-isoindol-5-carboxylic acid (100 mg, 0.356 mmol) and 3-pyrrolidin-1-yl-propylamine (100 μL, 0.772 mmol) were reacted with each other. Target compound in the amount of 75 mg (49%) was obtained by following the procedure described in Example 1.

$^1$H NMR (400 MHz, DMSO-d$_6$) δ 10.71 (br s, 1H), 9.07 (br s, 1H), 8.32 (s, 1H), 8.31 (d, 1H, J=8.6 Hz), 7.98 (d, 1H, J=7.5 Hz), 7.40-7.17 (m, 5H), 4.77 (s, 2H), 3.60-3.41 (m, 2H), 3.41-3.32 (m, 2H), 3.20-3.07 (m, 2H), 3.01-2.81 (m, 2H), 2.05-2.77 (m, 6H).

Example 53

Synthesis of 4-{2-[(2-benzyl-1,3-dioxo-2,3-dihydro-1H-isoindol-5-carbonyl)-amino]-ethyl}-4-morpholinium chloride (Compound 53)

2-benzyl-1,3-dioxo-2,3-dihydro-1H-isoindol-5-carboxylic acid (100 mg, 0.356 mmol) and 2-morpholinoethane amine (100 μL, 0.730 mmol) were reacted with each other. Target compound in the amount of 152 mg (99%) was obtained by following the procedure described in Example 1.

$^1$H NMR (400 MHz, DMSO-d$_6$) δ 10.51 (br s, 1H), 9.22 (br s, 1H), 8.37 (s, 1H), 8.31 (d, 1H, J=9.6 Hz), 8.03 (d, 1H, J=7.7 Hz), 7.42-7.21 (m, 5H), 4.81 (s, 2H), 4.04-3.92 (m, 2H), 3.82-3.65 (m, 4H), 3.60-3.48 (m, 2H), 3.41-3.25 (m, 2H), 3.18-3.04 (m, 2H).

Example 54

Synthesis of 4-{3-[(2-benzyl-1,3-dioxo-2,3-dihydro-1H-isoindol-5-carbonyl)-amino]-propyl}-4-morpholinium chloride (Compound 54)

2-benzyl-1,3-dioxo-2,3-dihydro-1H-isoindol-5-carboxylic acid (100 mg, 0.356 mmol) and 3-morpholin-1-yl-propylamine (100 μL, 0.696 mmol) were reacted with each other. Target compound in the amount of 109 mg (69%) was obtained by following the procedure described in Example 1.

$^1$H NMR (400 MHz, DMSO-d$_6$) δ 11.05 (br s, 1H), 9.09 (br s, 1H), 8.33 (s, 1H), 8.32 (d, 1H, J=8.2 Hz), 7.99 (d, 1H, J=7.6 Hz), 7.40-7.18 (m, 5H), 4.79 (s, 2H), 4.00-3.88 (m, 2H), 3.88-3.70 (m, 2H), 3.48-3.31 (m, 4H), 3.20-2.94 (m, 4H), 2.07-1.94 (m, 2H).

Example 55

Synthesis of 1-(2-{[2-(2-fluoro-benzyl)-1,3-dioxo-2,3-dihydro-1H-isoindol-5-carbonyl]-amino}-ethyl)-piperidinium chloride (Compound 55)

2-(2-fluoro-benzyl)-1,3-dioxo-2,3-dihydro-1H-isoindol-5-carboxylic acid (100 mg, 0.334 mmol) and 2-piperidin-1-yl-ethylamine (95 μL, 0.668 mmol) were reacted with each other. Target compound in the amount of 122 mg (82%) was obtained by following the procedure described in Example 1.

$^1$H NMR (400 MHz, DMSO-d$_6$) δ 10.12 (br s, 1H), 9.26 (s, 1H), 8.36 (s, 2H), 8.01 (d, 1H, J=6.8 Hz), 7.36-7.12 (m, 4H), 4.83 (s, 2H), 3.70 (br s, 2H), 3.50 (br s, 2H), 3.40-3.24 (m, 2H), 2.90 (br s, 2H), 1.81-1.35 (m, 6H).

Example 56

Synthesis of 1-(3-{[2-(2-fluoro-benzyl)-1,3-dioxo-2,3-dihydro-1H-isoindol-5-carbonyl]-amino}-propyl)-2-methyl-piperidinium chloride (Compound 56)

2-(2-fluoro-benzyl)-1,3-dioxo-2,3-dihydro-1H-isoindol-5-carboxylic acid (100 mg, 0.334 mmol) and 3-(2-methylpiperidin-1-yl)propan-1-amine (117 μL, 0.668 mmol) were reacted with each other. Target compound in the amount of 121 mg (76%) was obtained by following the procedure described in Example 1.

$^1$H NMR (400 MHz, DMSO-d$_6$) δ 10.38 (br s, 1H), 9.12 (s, 1H), 8.33 (d, 2H, J=5.9 Hz), 8.00 (d, 1H, J=7.9 Hz), 7.38-7.12 (m, 4H), 4.84 (s, 2H), 3.62 (br s, 0.3H), 3.60-3.40 (m, 2.7H), 3.24-3.02 (m, 3.3H), 2.98-2.78 (m, 0.7H), 2.05-1.55 (m, 7H), 1.55-1.35 (m, 1H), 1.29 (d, 2.1H, J=6.1 Hz), 1.23 (d, 0.9H, J=6.6 Hz).

Example 57

Synthesis of 1-(2-{[2-(2-fluoro-benzyl)-1,3-dioxo-2,3-dihydro-1H isoindol-5-carbonyl]-amino}-ethyl)-pyrrolidinium chloride (Compound 57)

2-(2-fluoro-benzyl)-1,3-dioxo-2,3-dihydro-1H-isoindol-5-carboxylic acid (100 mg, 0.334 mmol) and 2-pyrrolidin-1-yl-ethylamine (85 μL, 0.668 mmol) were reacted with each other. Target compound in the amount of 131 mg (91%) was obtained by following the procedure described in Example 1.

$^1$H NMR (400 MHz, DMSO-d$_6$) δ 10.38 (br s, 1H), 9.21 (s, 1H), 8.37 (s, 2H), 8.01 (d, 1H, J=7.4 Hz), 7.42-7.12 (m, 4H), 4.84 (s, 2H), 3.65 (br s, 4H), 3.52-3.22 (m, 2H), 3.03 (br s, 2H), 2.00 (br s, 2H), 1.88 (br s, 2H).

Example 58

Synthesis of 1-(3-{[2-(2-fluoro-benzyl)-1,3-dioxo-2,3-dihydro-1H-isoindol-5-carbonyl]-amino}-propyl)-pyrrolidinium chloride (Compound 58)

2-(2-fluoro-benzyl)-1,3-dioxo-2,3-dihydro-1H-isoindol-5-carboxylic acid (100 mg, 0.334 mmol) and 3-pyrrolidin-1-yl-propylamine (85 μL, 0.668 mmol) were reacted with each other. Target compound in the amount of 105 mg (71%) was obtained by following the procedure described in Example 1.

$^1$H NMR (400 MHz, DMSO-d$_6$) δ 10.35 (br s, 1H), 9.06 (s, 1H), 8.32 (d, 2H, J=9.4 Hz), 8.00 (d, 1H, J=7.7 Hz), 7.37-7.33 (m, 2H), 7.24-7.11 (m, 2H), 4.84 (s, 2H), 3.51 (br s, 2H), 3.41-3.36 (m, 2H), 3.16 (br s, 2H), 2.97 (br s, 2H), 2.00-1.86 (m, 6H).

Example 59

Synthesis of 4-(2-{[2-(2-fluoro-benzyl)-1,3-dioxo-2,3-dihydro-1H-isoindol-5-carbonyl]-amino}-ethyl)-4-morpholinium chloride (Compound 59)

2-(2-fluoro-benzyl)-1,3-dioxo-2,3-dihydro-1H-isoindol-5-carboxylic acid (100 mg, 0.334 mmol) and 2-morpholinoethane amine (87 μL, 0.668 mmol) were reacted with each other. Target compound in the amount of 67 mg (44%) was obtained by following the procedure described in Example 1.
$^1$H NMR (400 MHz, DMSO-$d_6$) δ 10.48 (br s, 1H), 9.21 (s, 1H), 8.48-8.32 (m, 2H), 8.03 (d, 1H, J=7.9 Hz), 7.50-7.10 (m, 4H), 4.85 (s, 2H), 4.00 (d, 2H, J=11.3 Hz), 3.90-3.70 (m, 4H), 3.55 (d, 2H, J=11.7 Hz), 3.39-3.32 (m, 2H), 3.25-3.05 (m, 2H).

Example 60

Synthesis of 4-(3-{[2-(2-fluoro-benzyl)-1,3-dioxo-2,3-dihydro-1H-isoindol-5-carbonyl]-amino}-propyl)-4-morpholinium chloride (Compound 60)

2-(2-fluoro-benzyl)-1,3-dioxo-2,3-dihydro-1H-isoindol-5-carboxylic acid (100 mg, 0.334 mmol) and 3-morpholin-1-yl-propylamine (98 μL, 0.668 mmol) were reacted with each other. Target compound in the amount of 135 mg (88%) was obtained by following the procedure described in Example 1.
$^1$H NMR (400 MHz, DMSO-$d_6$:$D_2O$=1:1) δ 8.18 (br s, 2H), 7.94-7.86 (m, 1H), 7.35-7.02 (m, 4H), 4.81 (s, 2H), 4.24 (s, 2H), 3.98-3.36 (m, 6H), 3.08 (br s, 4H), 1.90 (br s, 2H).

Example 61

Synthesis of 1-(2-{[2-(3-fluoro-benzyl)-1,3-dioxo-2,3-dihydro-1H-isoindol-5-carbonyl]-amino}-ethyl)-piperidinium chloride (Compound 61)

2-(3-fluoro-benzyl)-1,3-dioxo-2,3-dihydro-1H-isoindol-5-carboxylic acid (100 mg, 0.334 mmol) and 2-piperidin-1-yl-ethylamine (72 μL, 0.501 mmol) were reacted with each other. Target compound in the amount of 26 mg (17%) was obtained by following the procedure described in Example 1.
$^1$H NMR (400 MHz, DMSO-$d_6$) δ 9.89 (br s, 1H), 9.22 (s, 1H), 8.39-8.31 (m, 2H), 8.00 (d, 1H, J=7.7 Hz), 7.38-7.30 (m, 1H), 7.20-7.02 (m, 3H), 4.80 (s, 2H), 3.75-3.60 (m, 2H), 3.54-3.42 (m, 2H), 3.28-3.12 (m, 2H), 2.97-2.78 (m, 2H), 1.81-1.54 (m, 5H), 1.43-1.25 (m, 1H).

Example 62

Synthesis of 1-(3-{[2-(3-fluoro-benzyl)-1,3-dioxo-2,3-dihydro-1H-isoindol-5-carbonyl]-amino}-propyl)-2-methyl-piperidinium chloride (Compound 62)

2-(3-fluoro-benzyl)-1,3-dioxo-2,3-dihydro-1H-isoindol-5-carboxylic acid (100 mg, 0.334 mmol) and 3-(2-methylpiperidin-1-yl)propan-1-amine (117 μL, 0.668 mmol) were reacted with each other. Target compound in the amount of 76 mg (48%) was obtained by following the procedure described in $^1$H NMR (400 MHz, DMSO-$d_6$) δ 9.90 (br s, 1H), 9.07 (s, 1H), 8.32 (d, 2H, J=9.1 Hz), 8.01 (d, 1H, J=7.6 Hz), 7.41-7.35 (m, 1H), 7.19-7.08 (m, 3H), 4.81 (s, 2H), 3.59 (br s, 0.3H), 3.39-3.36 (m, 2.7H), 3.32-2.98 (m, 3.3H), 2.96-2.78 (m, 0.7H), 2.05-1.55 (m, 7H), 1.55-1.35 (m, 1H), 1.28 (d, 2.1H, J=5.3 Hz), 1.22 (d, 0.9H, J=6.4 Hz).

Example 63

Synthesis of 1-(2-{[2-(3-fluoro-benzyl)-1,3-dioxo-2,3-dihydro-1H-isoindol-5-carbonyl]-amino}-ethyl)-pyrrolidinium chloride (Compound 63)

2-(3-fluoro-benzyl)-1,3-dioxo-2,3-dihydro-1H-isoindol-5-carboxylic acid (100 mg, 0.334 mmol) and 2-pyrrolidin-1-yl-ethylamine (85 μL, 0.668 mmol) were reacted with each other. Target compound in the amount of 26 mg (18%) was obtained by following the procedure described in Example 1.
$^1$H NMR (400 MHz, DMSO-$d_6$:$D_2O$=1:1) δ 8.19 (d, 2H, J=8.1 Hz), 7.95 (d, 1H, J=7.9 Hz), 7.33 (t, 1H, J=7.4 Hz), 7.12-7.03 (m, 3H), 4.78 (s, 2H), 4.24-4.00 (m, 4H), 3.71-3.52 (m, 2H), 3.52-3.38 (m, 2H), 1.91 (s, 4H).

Example 64

Synthesis of 1-(3-{[2-(3-fluoro-benzyl)-1,3-dioxo-2,3-dihydro-1H-isoindol-5-carbonyl]-amino}-propyl)-pyrrolidinium chloride (Compound 64)

2-(3-fluoro-benzyl)-1,3-dioxo-2,3-dihydro-1H-isoindol-5-carboxylic acid (100 mg, 0.334 mmol) and 3-pyrrolidin-1-yl-propylamine (85 μL, 0.668 mmol) were reacted with each other. Target compound in the amount of 101 mg (67%) was obtained by following the procedure described in Example 1.
$^1$H NMR (400 MHz, DMSO-$d_6$) δ 10.25 (br s, 1H), 9.04 (t, 1H, J=5.4 Hz), 8.34-8.29 (m, 2H), 8.01 (d, 1H, J=7.6 Hz), 7.41-7.34 (m, 1H), 7.18-7.08 (m, 3H), 4.81 (s, 2H), 3.52 (br s, 2H), 3.39-3.36 (m, 2H), 3.16 (br s, 2H), 2.97 (br s, 2H), 2.00-1.86 (m, 6H).

Example 65

Synthesis of 4-(2-{[2-(3-fluoro-benzyl)-1,3-dioxo-2,3-dihydro-1H-isoindol-5-carbonyl]-amino}-ethyl)-4-morpholinium chloride (Compound 65)

2-(3-fluoro-benzyl)-1,3-dioxo-2,3-dihydro-1H-isoindol-5-carboxylic acid (100 mg, 0.334 mmol) and 2-morpholinoethane amine (87 μL, 0.668 mmol) were reacted with each other. Target compound in the amount of 132 mg (88%) was obtained by following the procedure described in Example 1.
$^1$H NMR (400 MHz, DMSO-$d_6$) δ 10.70 (br s, 1H), 9.24 (s, 1H), 8.37 (s, 1H), 8.36 (s, 1H), 8.02 (d, 1H, J=7.3 Hz), 7.37 (t, 1H, J=8.0 Hz), 7.36-7.03 (m, 3H), 4.81 (s, 2H), 3.98 (d, 2H, J=12.5 Hz), 3.88-3.62 (m, 4H), 3.54 (d, 2H, J=11.8 Hz), 3.50-3.22 (m, 2H), 3.13 (d, 2H, J=9.8 Hz).

Example 66

Synthesis of 4-(3-{[2-(3-fluoro-benzyl)-1,3-dioxo-2,3-dihydro-1H-isoindol-5-carbonyl]-amino}-propyl)-4-morpholinium chloride (Compound 66)

2-(3-fluoro-benzyl)-1,3-dioxo-2,3-dihydro-1H-isoindol-5-carboxylic acid (100 mg, 0.334 mmol) and 3-morpholin-1-yl-propylamine (73 μL, 0.501 mmol) were reacted with

Example 67

Synthesis of 1-(3-{[2-(3-fluoro-benzyl)-1,3-dioxo-2,
3-dihydro-1H-isoindol-5-carbonyl]-amino}-propyl)-
4-methyl-1-piperazinium chloride (Compound 67)

2-(3-fluoro-benzyl)-1,3-dioxo-2,3-dihydro-1H-isoindol-5-carboxylic acid (100 mg, 0.334 mmol) and 3-(4-methylpiperazin-1-yl)propan-1-amine (114 µL, 0.668 mmol) were reacted with each other. Target compound in the amount of 148 mg (94%) was obtained by following the procedure described in Example 1.

$^1$H NMR (400 MHz, DMSO-d$_6$:D$_2$O=1:1) δ 8.06 (d, 2H, J=6.4 Hz), 7.86-7.83 (m, 1H), 7.27-7.21 (m, 1H), 7.04-6.91 (m, 3H), 4.71 (s, 2H), 4.58-4.40 (m, 4H), 4.08-3.82 (m, 2H), 3.73-3.54 (m, 2H), 3.09 (t, 2H, J=6.9 Hz), 3.06-2.86 (m, 2H), 2.01-1.82 (m, 2H).

Example 67

Synthesis of 1-(3-{[2-(3-fluoro-benzyl)-1,3-dioxo-2,
3-dihydro-1H-isoindol-5-carbonyl]-amino}-propyl)-
4-methyl-1-piperazinium chloride (Compound 67)

2-(3-fluoro-benzyl)-1,3-dioxo-2,3-dihydro-1H-isoindol-5-carboxylic acid (100 mg, 0.334 mmol) and 3-(4-methylpiperazin-1-yl)propan-1-amine (114 µL, 0.668 mmol) were reacted with each other. Target compound in the amount of 148 mg (94%) was obtained by following the procedure described in Example 1.

$^1$H NMR (400 MHz, DMSO-d$_6$:D$_2$O=1:1) δ 8.16-8.13 (m, 2H), 7.93 (d, 1H, J=8.1 Hz), 7.28 (q, 1H, J=8.2 Hz), 7.08 (d, 1H, J=7.8 Hz), 7.04 (d, 2H, J=9.2 Hz), 4.77 (s, 2H), 4.47 (br s, 4H), 4.42-4.31 (m, 2H), 4.31-4.12 (m, 2H), 3.52-3.32 (m, 2H), 3.10 (t, 2H, J=7.8 Hz), 2.81 (s, 3H), 1.91 (br s, 2H).

Example 68

Synthesis of 1-(2-{[2-(4-fluoro-benzyl)-1,3-dioxo-2,
3-dihydro-1H-isoindol-5-carbonyl]-amino}-ethyl)-
piperidinium chloride (Compound 68)

2-(4-fluoro-benzyl)-1,3-dioxo-2,3-dihydro-1H-isoindol-5-carboxylic acid (100 mg, 0.334 mmol) and 2-piperidin-1-yl-ethylamine (72 µL, 0.501 mmol) were reacted with each other. Target compound in the amount of 117 mg (79%) was obtained by following the procedure described in Example 1.

$^1$H NMR (400 MHz, DMSO-d$_6$) δ 10.36 (br s, 1H), 9.32 (t, 1H, J=5.1 Hz), 8.36 (br s, 2H), 7.99 (d, 1H, J=8.0 Hz), 7.37 (dd, 2H, J=8.1, 5.9 Hz), 7.15 (t, 1H, J=8.7 Hz), 4.77 (s, 2H), 3.79-3.65 (m, 2H), 3.57-3.45 (m, 2H), 3.30-3.17 (m, 2H), 2.98-2.81 (m, 2H), 1.90-1.51 (m, 5H), 1.46-1.29 (m, 2H).

Example 69

Synthesis of 1-(3-{[2-(4-fluoro-benzyl)-1,3-dioxo-2,
3-dihydro-1H-isoindol-5-carbonyl]-amino}-propyl)-
2-methyl-piperidinium chloride (Compound 69)

2-(4-fluoro-benzyl)-1,3-dioxo-2,3-dihydro-1H-isoindol-5-carboxylic acid (100 mg, 0.334 mmol) and 3-(2-methylpiperidin-1-yl)propan-1-amine (117 µL, 0.668 mmol) were reacted with each other. Target compound in the amount of 131 mg (83%) was obtained by following the procedure described in Example 1.

$^1$H NMR (400 MHz, DMSO-d$_6$) δ 10.25 (br s, 1H), 9.09 (d, 1H, J=4.2 Hz), 8.31 (d, 2H, J=6.8 Hz), 7.99 (d, 1H, J=8.0 Hz), 7.39-7.34 (m, 2H), 7.18-7.11 (m, 2H), 4.77 (s, 2H), 3.61 (br s, 0.3H), 3.52-3.36 (m, 2.7H), 3.30-2.98 (m, 3.3H), 2.96-2.78 (m, 0.7H), 2.05-1.55 (m, 7H), 1.55-1.35 (m, 1H), 1.28 (d, 2.1H, J=6.1 Hz), 1.21 (d, 0.9H, J=6.6 Hz).

Example 70

Synthesis of 1-(2-{[2-(4-fluoro-benzyl)-1,3-dioxo-2,
3-dihydro-1H-isoindol-5-carbonyl]-amino}-ethyl)-
pyrrolidinium chloride (Compound 70)

2-(4-fluoro-benzyl)-1,3-dioxo-2,3-dihydro-1H-isoindol-5-carboxylic acid (100 mg, 0.334 mmol) and 2-pyrrolidin-1-yl-ethylamine (85 µL, 0.668 mmol) were reacted with each other. Target compound in the amount of 102 mg (69%) was obtained by following the procedure described in Example 1.

$^1$H NMR (400 MHz, DMSO-d$_6$:D$_2$O=1:1) δ 8.09 (d, 2H, J=6.4 Hz), 7.85 (d, 1H, J=7.4 Hz), 7.23 (t, 2H, J=7.3 Hz), 6.98 (t, 2H, J=8.4 Hz), 4.67 (s, 2H), 3.78-3.52 (m, 4H), 3.30-3.28 (m, 2H), 2.98 (br s, 2H), 2.03-1.79 (m, 4H).

Example 71

Synthesis of 1-(3-{[2-(4-fluoro-benzyl)-1,3-dioxo-2,
3-dihydro-1H-isoindol-5-carbonyl]-amino}-propyl)-
pyrrolidinium chloride (Compound 71)

2-(4-fluoro-benzyl)-1,3-dioxo-2,3-dihydro-1H-isoindol-5-carboxylic acid (100 mg, 0.334 mmol) and 3-pyrrolidin-1-yl-propylamine (85 µL, 0.668 mmol) were reacted with each other. Target compound in the amount of 92 mg (62%) was obtained by following the procedure described in Example 1.

$^1$H NMR (400 MHz, DMSO-d$_6$) δ 10.62 (br s, 1H), 9.07 (t, 1H, J=5.0 Hz), 8.34-8.30 (m, 2H), 8.00 (d, 1H, J=7.6 Hz), 7.37 (t, 2H, J=7.7 Hz), 7.15 (t, 2H, J=8.6 Hz), 4.78 (s, 2H), 3.50 (br s, 2H), 3.40-3.30 (m, 2H), 3.17-3.14 (m, 2H), 3.02-2.96 (m, 2H), 1.98-1.84 (m, 6H).

Example 72

Synthesis of 4-(2-{[2-(4-fluoro-benzyl)-1,3-dioxo-2,
3-dihydro-1H-isoindol-5-carbonyl]-amino}-ethyl)-4-
morpholinium chloride (Compound 72)

2-(4-fluoro-benzyl)-1,3-dioxo-2,3-dihydro-1H-isoindol-5-carboxylic acid (100 mg, 0.334 mmol) and 2-morpholinoethane amine (87 µL, 0.668 mmol) were reacted with each other. Target compound in the amount of 116 mg (78%) was obtained by following the procedure described in Example 1.

$^1$H NMR (400 MHz, DMSO-d$_6$:D$_2$O=1:1) δ 6.26 (d, 2H, J=4.5 Hz), 6.12-5.95 (m, 1H), 5.45-5.36 (m, 2H), 5.30-5.11 (m, 2H), 2.84 (s, 2H), 2.21-1.68 (m, 4H), 1.49-1.26 (m, 4H), 0.70-0.48 (m, 4H).

Example 73

Synthesis of 4-(3-{[2-(4-fluoro-benzyl)-1,3-dioxo-2,
3-dihydro-1H-isoindol-5-carbonyl]-amino}-propyl)-
4-morpholinium chloride (Compound 73)

2-(4-fluoro-benzyl)-1,3-dioxo-2,3-dihydro-1H-isoindol-5-carboxylic acid (100 mg, 0.334 mmol) and 3-morpholin-1-yl-propylamine (73 µL, 0.501 mmol) were reacted with each other. Target compound in the amount of 64 mg (42%) was obtained by following the procedure described in Example 1.

$^1$H NMR (400 MHz, DMSO-d$_6$) δ 10.39 (br s, 1H), 9.05 (t, 1H, J=5.3 Hz), 8.33-8.30 (m, 2H), 8.01 (d, 1H, J=7.7 Hz), 7.40-7.35 (m, 2H), 7.17 (t, 2H, J=8.9 Hz), 4.78 (s, 2H), 3.96 (d, 2H, J=13.2 Hz), 3.73 (t, 2H, J=12.2 Hz), 3.48-3.37 (m, 4H), 3.21-3.12 (m, 2H), 3.12-2.99 (m, 2H), 2.04-1.90 (m, 2H).

Example 74

Synthesis of 1-(3-{[2-(4-fluoro-benzyl)-1,3-dioxo-2,3-dihydro-1H-isoindol-5-carbonyl]-amino}-propyl)-4-methyl-1-piperazinium chloride (Compound 74)

2-(4-fluoro-benzyl)-1,3-dioxo-2,3-dihydro-1H-isoindol-5-carboxylic acid (100 mg, 0.334 mmol) and 3-(4-methylpiperazin-1-yl)propan-1-amine (114 μL, 0.668 mmol) were reacted with each other. Target compound in the amount of 134 mg (84%) was obtained by following the procedure described in Example 1.

$^1$H NMR (400 MHz, DMSO-d$_6$:D$_2$O=1:1) δ 8.09 (t, 2H, J=4.2 Hz), 7.89 (d, 1H, J=8.2 Hz), 7.28 (q, 2H, J=5.4 Hz), 7.04 (t, 2H, J=8.8 Hz), 4.72 (s, 2H), 4.65 (bt s, 2H), 4.60 (s, 4H), 4.55-4.45 (m, 2H), 4.43-4.14 (m, 2H), 3.44-3.34 (m, 2H), 3.12 (t, 2H, J=8.1 Hz), 2.82 (s, 3H), 1.92 (br s, 2H).

Example 75

Synthesis of 1-(2-{[2-(2-chloro-benzyl)-1,3-dioxo-2,3-dihydro-1H-isoindol-5-carbonyl]-amino}-ethyl)-piperidinium chloride (Compound 75)

2-(2-chloro-benzyl)-1,3-dioxo-2,3-dihydro-1H-isoindol-5-carboxylic acid (100 mg, 0.316 mmol) and 2-piperidin-1-yl-ethylamine (113 μL, 0.792 mmol) were reacted with each other. Target compound in the amount of 131 mg (90%) was obtained by following the procedure described in Example 1.

$^1$H NMR (400 MHz, DMSO-d$_6$) δ 10.33 (br s, 1H), 9.32 (t, 1H, J=5.2 Hz), 8.41-8.32 (m, 2H), 8.02 (d, 1H, J=8.2 Hz), 7.48 (d, 1H, J=7.5 Hz), 7.49-7.20 (m, 3H), 4.84 (s, 2H), 3.78-3.62 (m, 2H), 3.57-3.43 (m, 2H), 3.29-3.14 (m, 2H), 2.98-2.81 (m, 2H), 1.90-1.60 (m, 5H), 1.49-1.30 (m, 2H).

Example 76

Synthesis of 1-(3-{[2-(2-chloro-benzyl)-1,3-dioxo-2,3-dihydro-1H-isoindol-5-carbonyl]-amino}-propyl)-2-methyl-piperidinium chloride (Compound 76)

2-(2-chloro-benzyl)-1,3-dioxo-2,3-dihydro-1H-isoindol-5-carboxylic acid (100 mg, 0.316 mmol) and 3-(2-methylpiperidin-1-yl)propan-1-amine (138 μL, 0.792 mmol) were reacted with each other. Target compound in the amount of 92 mg (60%) was obtained by following the procedure described in Example 1.

$^1$H NMR (400 MHz, DMSO-d$_6$) δ 10.42 (br s, 1H), 9.13 (d, 1H, J=4.8 Hz), 8.35 (s, 1H), 8.33 (d, 1H, J=4.4 Hz), 8.02 (d, 1H, J=8.4 Hz), 7.5 (d, 1H, J=7.5 Hz), 7.34-7.28 (m, 3H), 4.85 (s, 1H), 3.55 (br s, 0.3H), 3.41-3.36 (m, 2.7H), 3.28-2.92 (m, 3.3H), 2.90-2.78 (m, 0.7H), 2.05-1.55 (m, 7H), 1.55-1.35 (m, 1H), 1.29 (d, 2.1H, J=6.2 Hz), 1.22 (d, 0.9H, J=6.8 Hz).

Example 77

Synthesis of 1-(2-{[2-(2-chloro-benzyl)-1,3-dioxo-2,3-dihydro-1H-isoindol-5-carbonyl]-amino}-ethyl)-pyrrolidinium chloride (Compound 77)

2-(2-chloro-benzyl)-1,3-dioxo-2,3-dihydro-1H-isoindol-5-carboxylic acid (100 mg, 0.316 mmol) and 2-pyrrolidin-1-yl-ethylamine (100 μL, 0.792 mmol) were reacted with each other. Target compound in the amount of 121 mg (85%) was obtained by following the procedure described in Example 1.

$^1$H NMR (400 MHz, DMSO-d$_6$) δ 10.75 (br s, 1H), 9.29 (t, 1H, J=5.3 Hz), 8.40 (s, 1H), 8.39 (d, 1H, J=6.8 Hz), 8.02 (d, 1H, J=8.3 Hz), 7.48 (d, 1H, J=7.5 Hz), 7.38-7.21 (m, 3H), 4.85 (s, 2H), 3.75-3.54 (m, 4H), 3.40-3.29 (m, 2H), 3.11-2.94 (m, 2H), 2.10-1.82 (m, 4H).

Example 78

Synthesis of 1-(3-{[2-(2-chloro-benzyl)-1,3-dioxo-2,3-dihydro-1H-isoindol-5-carbonyl]-amino}-propyl)-pyrrolidinium chloride (Compound 78)

2-(2-chloro-benzyl)-1,3-dioxo-2,3-dihydro-1H-isoindol-5-carboxylic acid (100 mg, 0.316 mmol) and 3-pyrrolidin-1-yl-propylamine (100 μL, 0.792 mmol) were reacted with each other. Target compound in the amount of 85 mg (58%) was obtained by following the procedure described in Example 1.

$^1$H NMR (400 MHz, DMSO-d$_6$) δ 10.76 (br s, 1H), 9.09 (t, 1H, J=5.5 Hz), 8.35 (s, 1H), 8.33 (d, 1H, J=8.1 Hz), 8.01 (d, 1H, J=7.6 Hz), 7.48 (d, 1H, J=7.6 Hz), 7.38-7.22 (m, 3H), 4.85 (s, 2H), 3.58-3.44 (m, 2H), 3.44-3.32 (m, 2H), 3.21-3.10 (m, 2H), 3.01-2.87 (m, 2H), 2.06-1.80 (m, 6H).

Example 79

Synthesis of 4-(2-{[2-(2-chloro-benzyl)-1,3-dioxo-2,3-dihydro-1H-isoindol-5-carbonyl]-amino}-ethyl)-4-morpholinium chloride (Compound 79)

2-(2-chloro-benzyl)-1,3-dioxo-2,3-dihydro-1H-isoindol-5-carboxylic acid (100 mg, 0.316 mmol) and 2-morpholinoethane amine (103 μL, 0.792 mmol) were reacted with each other. Target compound in the amount of 93 mg (63%) was obtained by following the procedure described in Example 1.

$^1$H NMR (400 MHz, DMSO-d$_6$) δ 11.10 (br s, 1H), 9.30 (t, 1H, J=5.1 Hz), 8.40 (s, 1H), 8.39 (d, 1H, J=6.8 Hz), 8.02 (d, 1H, J=8.2 Hz), 7.48 (d, 1H, J=7.5 Hz), 7.40-7.21 (m, 3H), 4.85 (s, 2H), 4.07-3.92 (m, 2H), 3.92-3.80 (m, 2H), 3.80-3.68 (m, 2H), 3.60-3.49 (m, 2H), 3.40-3.29 (m, 2H), 3.19-3.04 (m, 2H).

Example 80

Synthesis of 4-(3-{[2-(2-chloro-benzyl)-1,3-dioxo-2,3-dihydro-1H-isoindol-5-carbonyl]-amino}-propyl)-4-morpholinium chloride (Compound 80)

2-(2-chloro-benzyl)-1,3-dioxo-2,3-dihydro-1H-isoindol-5-carboxylic acid (100 mg, 0.316 mmol) and 3-morpholin-1-yl-propylamine (116 μL, 0.792 mmol) were reacted with each other. Target compound in the amount of 89 mg (59%) was obtained by following the procedure described in Example 1.

$^1$H NMR (400 MHz, DMSO-d$_6$) δ 11.06 (br s, 1H), 9.10 (t, 1H, J=5.1 Hz), 8.35 (s, 1H), 8.34 (d, 1H, J=8.3 Hz), 8.02 (d, 1H, J=7.7 Hz), 7.48 (d, 1H, J=7.5 Hz), 7.40-7.21 (m, 3H), 4.85 (s, 2H), 4.01-3.88 (m, 2H), 3.88-3.71 (m, 2H), 3.50-3.36 (m, 4H), 3.21-2.98 (m, 4H), 2.10-1.92 (m, 2H).

Example 81

Synthesis of 1-(2-{[2-(3-chloro-benzyl)-1,3-dioxo-2,3-dihydro-1H-isoindol-5-carbonyl]-amino}-ethyl)-piperidinium chloride (Compound 81)

2-(3-chloro-benzyl)-1,3-dioxo-2,3-dihydro-1H-isoindol-5-carboxylic acid (100 mg, 0.316 mmol) and 2-piperidin-1- yl-ethylamine (113 μL, 0.792 mmol) were reacted with each other. Target compound in the amount of 135 mg (92%) was obtained by following the procedure described in Example 1.

$^1$H NMR (400 MHz, DMSO-d$_6$) δ 10.31 (br s, 1H), 9.31 (br s, 1H), 8.37 (br s, 2H), 8.00 (d, 1H, J=8.0 Hz), 7.45-7.21 (m, 4H), 4.79 (s, 2H), 3.78-3.64 (m, 2H), 3.58-3.43 (m, 2H), 3.30-3.15 (m, 2H), 2.99-2.81 (m, 2H), 1.90-1.60 (m, 5H), 1.48-1.30 (m, 1H).

Example 82

Synthesis of 1-(3-{[2-(3-chloro-benzyl)-1,3-dioxo-2, 3-dihydro-1H-isoindol-5-carbonyl]-amino}-propyl)-2-methyl-piperidinium chloride (Compound 82)

2-(3-chloro-benzyl)-1,3-dioxo-2,3-dihydro-1H-isoindol-5-carboxylic acid (100 mg, 0.316 mmol) and 3-(2-methylpiperidin-1-yl)propan-1-amine (138 μL, 0.792 mmol) were reacted with each other. Target compound in the amount of 106 mg (68%) was obtained by following the procedure described in Example 1.

$^1$H NMR (400 MHz, DMSO-d$_6$) δ 9.70 (br s, 0.3H), 9.58 (br s, 0.7H), 9.04 (br s, 1H), 8.32 (s, 1H), 8.30 (d, 1H, J=8.4 Hz), 8.01 (d, 1H, J=7.8 Hz), 7.46-7.23 (m, 4H), 4.80 (s, 2H), 3.68-3.54 (m, 0.3H), 3.46-2.98 (m, 6H), 2.98-2.89 (m, 0.7H), 2.02-1.39 (m, 8H), 1.32-1.18 (m, 3H).

Example 83

Synthesis of 1-(2-{[2-(3-chloro-benzyl)-1,3-dioxo-2, 3-dihydro-1H-isoindol-5-carbonyl]-amino}-ethyl)-pyrrolidinium chloride (Compound 83)

2-(3-chloro-benzyl)-1,3-dioxo-2,3-dihydro-1H-isoindol-5-carboxylic acid (100 mg, 0.316 mmol) and 2-pyrrolidin-1-yl-ethylamine (100 μL, 0.792 mmol) were reacted with each other. Target compound in the amount of 108 mg (76%) was obtained by following the procedure described in Example 1.

$^1$H NMR (400 MHz, DMSO-d$_6$) δ 9.98 (br s, 1H), 9.15 (t, 1H, J=5.5 Hz), 8.36 (s, 1H), 8.32 (d, 1H, J=6.6 Hz), 8.03 (d, 1H, J=7.7 Hz), 7.46-7.24 (m, 4H), 4.81 (s, 2H), 3.70-3.58 (m, 4H), 3.41-3.25 (m, 2H), 3.11-2.99 (m, 2H), 2.09-1.94 (m, 2H), 1.94-1.80 (m, 2H).

Example 84

Synthesis of 1-(3-{[2-(3-chloro-benzyl)-1,3-dioxo-2, 3-dihydro-1H-isoindol-5-carbonyl]-amino}-propyl)-pyrrolidinium chloride (Compound 84)

2-(3-chloro-benzyl)-1,3-dioxo-2,3-dihydro-1H-isoindol-5-carboxylic acid (100 mg, 0.316 mmol) and 3-pyrrolidin-1-yl-propylamine (100 μL, 0.792 mmol) were reacted with each other. Target compound in the amount of 46 mg (31%) was obtained by following the procedure described in Example 1.

$^1$H NMR (400 MHz, DMSO-d$_6$) δ 10.20 (br s, 1H), 9.03 (t, 1H, J=5.7 Hz), 8.32 (s, 1H), 8.30 (d, 1H, J=7.8 Hz), 8.00 (d, 1H, J=7.7 Hz), 7.42-7.23 (m, 4H), 4.80 (s, 2H), 3.58-3.47 (m, 2H), 3.43-3.34 (m, 2H), 3.21-3.12 (m, 2H), 3.02-2.90 (m, 2H), 2.07-1.78 (m, 6H)

Example 85

Synthesis of 4-(2-{[2-(3-chloro-benzyl)-1,3-dioxo-2, 3-dihydro-1H-isoindol-5-carbonyl]-amino}-ethyl)-4-morpholinium chloride (Compound 85)

2-(3-chloro-benzyl)-1,3-dioxo-2,3-dihydro-1H-isoindol-5-carboxylic acid (100 mg, 0.316 mmol) and 2-morpholinoethane amine (103 μL, 0.792 mmol) were reacted with each other. Target compound in the amount of 59 mg (40%) was obtained by following the procedure described in Example 1.

$^1$H NMR (400 MHz, DMSO-d$_6$) δ 10.50 (br s, 1H), 9.20 (br s, 1H), 8.35 (s, 1H), 8.34 (d, 1H, J=7.8 Hz), 8.01 (d, 1H, J=8.0 Hz), 7.47-7.21 (m, 4H), 4.80 (s, 2H), 4.06-3.93 (m, 2H), 3.82-3.68 (m, 4H), 3.60-3.50 (m, 2H), 3.41-3.30 (m, 2H), 3.21-3.07 (m, 2H).

Example 86

Synthesis of 4-(3-{[2-(3-chloro-benzyl)-1,3-dioxo-2, 3-dihydro-1H-isoindol-5-carbonyl]-amino}-propyl)-4-morpholinium chloride (Compound 86)

2-(3-chloro-benzyl)-1,3-dioxo-2,3-dihydro-1H-isoindol-5-carboxylic acid (100 mg, 0.316 mmol) and 3-morpholin-1-yl-propylamine (116 μL, 0.792 mmol) were reacted with each other. Target compound in the amount of 111 mg (73%) was obtained by following the procedure described in Example 1.

$^1$H NMR (400 MHz, DMSO-d$_6$) δ 11.08 (br s, 1H), 9.11-9.00 (m, 1H), 8.32-8.20 (m, 2H), 7.99 (d, 1H, J=8.2 Hz), 7.40-7.18 (m, 4H), 4.79 (s, 2H), 3.93 (d, 2H, J=10.3 Hz), 3.88-3.75 (m, 2H), 3.48-3.35 (m, 2H), 3.20-2.92 (m, 4H), 2.10-1.92 (m, 2H).

Example 87

Synthesis of 1-(2-{[2-(4-chloro-benzyl)-1,3-dioxo-2, 3-dihydro-1H-isoindol-5-carbonyl]-amino}-ethyl)-piperidinium chloride (Compound 87)

2-(4-chloro-benzyl)-1,3-dioxo-2,3-dihydro-1H-isoindol-5-carboxylic acid (100 mg, 0.316 mmol) and 2-piperidin-1-yl-ethylamine (113 μL, 0.792 mmol) were reacted with each other. Target compound in the amount of 77 mg (53%) was obtained by following the procedure described in Example 1.

$^1$H NMR (400 MHz, DMSO-d$_6$) δ 10.26 (br s, 1H), 9.29 (t, 1H, J=5.0 Hz), 8.39-8.28 (m, 2H), 7.99 (d, 1H, J=8.1 Hz), 7.42-7.26 (m, 4H), 4.77 (s, 2H), 3.78-3.64 (m, 2H), 3.58-3.41 (m, 2H), 3.29-3.13 (m, 2H), 2.98-2.82 (m, 2H), 1.89-1.61 (m, 5H), 1.43-1.29 (m, 1H).

Example 88

Synthesis of 1-(3-{[2-(4-chloro-benzyl)-1,3-dioxo-2, 3-dihydro-1H-isoindol-5-carbonyl]-amino}-propyl)-2-methyl-piperidinium chloride (Compound 88)

2-(4-chloro-benzyl)-1,3-dioxo-2,3-dihydro-1H-isoindol-5-carboxylic acid (100 mg, 0.316 mmol) and 3-(2-methylpiperidin-1-yl)propan-1-amine (138 μL, 0.792 mmol) were reacted with each other. Target compound in the amount of 136 mg (87%) was obtained by following the procedure described in Example 1.

¹H NMR (400 MHz, DMSO-d₆) δ 10.36 (br s, 1H), 9.15-9.02 (m, 1H), 8.39-8.22 (m, 2H), 7.99 (d, 1H, J=7.8 Hz), 7.43-7.22 (m, 4H), 4.77 (s, 2H), 3.63-3.50 (m, 0.3H), 3.49-3.30 (m, 2H), 3.30-2.96 (m, 4H), 2.96-2.80 (m, 0.7H), 2.07-1.88 (m, 2H), 1.88-1.55 (m, 5H), 1.55-1.38 (m, 1H), 1.28 (d, 2.1H, J=6.0 Hz), 1.21 (d, 0.9H, J=6.5 Hz).

Example 89

Synthesis of 1-(2-{[2-(4-chloro-benzyl)-1,3-dioxo-2,3-dihydro-1H-isoindol-5-carbonyl]-amino}-ethyl)-pyrrolidinium chloride (Compound 89)

2-(4-chloro-benzyl)-1,3-dioxo-2,3-dihydro-1H-isoindol-5-carboxylic acid (100 mg, 0.316 mmol) and 2-pyrrolidin-1-yl-ethylamine (100 μL, 0.792 mmol) were reacted with each other. Target compound in the amount of 106 mg (75%) was obtained by following the procedure described in Example 1.
¹H NMR (400 MHz, DMSO-d₆) δ 10.19 (br s, 1H), 9.18 (t, 1H, J=5.3 Hz), 8.40-8.29 (m, 2H), 8.01 (d, 1H, J=7.6 Hz), 7.43-7.24 (m, 4H), 4.78 (s, 2H), 3.70-3.56 (m, 4H), 3.41-3.39 (m, 2H), 3.10-2.96 (m, 2H), 2.08-1.92 (m, 2H), 1.92-1.79 (m, 2H).

Example 90

Synthesis of 1-(3-{[2-(4-chloro-benzyl)-1,3-dioxo-2,3-dihydro-1H-isoindol-5-carbonyl]-amino}-propyl)-pyrrolidinium chloride (Compound 90)

2-(4-chloro-benzyl)-1,3-dioxo-2,3-dihydro-1H-isoindol-5-carboxylic acid (100 mg, 0.316 mmol) and 3-pyrrolidin-1-yl-propylamine (100 μL, 0.792 mmol) were reacted with each other. Target compound in the amount of 57 mg (39%) was obtained by following the procedure described in Example 1.
¹H NMR (400 MHz, DMSO-d₆) δ 10.75 (br s, 1H), 9.07 (t, 1H, J=5.0 Hz), 8.33 (s, 1H), 8.31 (s, 1H), 8.00 (d, 1H, J=7.6 Hz), 7.37 (t, 2H, J=7.7 Hz), 7.16 (t, 2H, J=8.4 Hz), 4.78 (s, 2H), 3.50 (br s, 2H), 3.40-3.30 (m, 2H), 3.17-3.15 (m, 2H), 2.96 (br s, 2H), 2.15-1.76 (m, 6H)

Example 91

Synthesis of 4-(2-{[2-(4-chloro-benzyl)-1,3-dioxo-2,3-dihydro-1H-isoindol-5-carbonyl]-amino}-ethyl)-4-morpholinium chloride (Compound 91)

2-(4-chloro-benzyl)-1,3-dioxo-2,3-dihydro-1H-isoindol-5-carboxylic acid (100 mg, 0.316 mmol) and 2-morpholinoethane amine (103 μL, 0.792 mmol) were reacted with each other. Target compound in the amount of 122 mg (83%) was obtained by following the procedure described in Example 1.
¹H NMR (400 MHz, DMSO-d₆) δ 10.45 (br s, 1H), 9.20 (br s, 1H), 8.35 (s, 1H), 8.34 (d, 1H, J=7.7 Hz), 8.02 (d, 1H, J=8.0 Hz), 7.42-7.27 (m, 4H), 4.78 (s, 2H), 4.05-3.91 (m, 2H), 3.81-3.64 (m, 4H), 3.58-3.49 (m, 2H), 3.38-3.27 (m, 2H), 3.20-3.16 (m, 2H).

Example 92

Synthesis of 4-(3-{[2-(4-chloro-benzyl)-1,3-dioxo-2,3-dihydro-1H-isoindol-5-carbonyl]-amino}-propyl)-4-morpholinium chloride (Compound 92)

2-(4-chloro-benzyl)-1,3-dioxo-2,3-dihydro-1H-isoindol-5-carboxylic acid (100 mg, 0.316 mmol) and 3-morpholin-1-yl-propylamine (116 μL, 0.792 mmol) were reacted with each other. Target compound in the amount of 71 mg (47%) was obtained by following the procedure described in Example 1.
¹H NMR (400 MHz, DMSO-d₆) δ 10.61 (br s, 1H), 9.10-9.00 (m, 1H), 8.32 (s, 1H), 8.30 (d, 1H, J=8.9 Hz), 8.00 (d, 1H, J=7.6 Hz), 7.50-7.27 (m, 4H), 4.78 (s, 2H), 4.00-3.89 (m, 2H), 3.75 (t, 2H, J=12.2 Hz), 3.46-3.25 (m, 4H), 3.18-3.09 (m, 2H), 3.09-2.96 (m, 2H), 2.04-1.90 (m, 2H).

Example 93

Synthesis of 1-(2-{[2-(2-methyl-benzyl)-1,3-dioxo-2,3-dihydro-1H-isoindol-5-carbonyl]-amino}-ethyl)-piperidinium chloride (Compound 93)

2-(2-methyl-benzyl)-1,3-dioxo-2,3-dihydro-1H-isoindol-5-carboxylic acid (100 mg, 0.338 mmol) and 2-piperidin-1-yl-ethylamine (97 μL, 0.677 mmol) were reacted with each other. Target compound in the amount of 110 mg (73%) was obtained by following the procedure described in Example 1.
¹H NMR (400 MHz, DMSO-d₆) δ 10.45 (br s, 1H), 9.33 (t, 1H, J=4.9 Hz), 8.37 (br s, 2H), 7.99 (d, 1H, J=8.0 Hz), 7.31-6.99 (m, 4H), 4.75 (s, 2H), 3.79-3.62 (m, 2H), 3.56-3.42 (m, 2H), 3.28-3.14 (m, 2H), 3.00-2.80 (m, 2H), 2.37 (s, 3H), 1.93-1.59 (m, 5H), 1.43-1.28 (m, 1H).

Example 94

Synthesis of 2-methyl-1-(3-{[2-(2-methyl-benzyl)-1,3-dioxo-2,3-dihydro-1H-isoindol-5-carbonyl]-amino}-propyl)-piperidinium chloride (Compound 94)

2-(2-methyl-benzyl)-1,3-dioxo-2,3-dihydro-1H-isoindol-5-carboxylic acid (100 mg, 0.338 mmol) and 3-(2-methylpiperidin-1-yl)propan-1-amine (118 μL, 0.677 mmol) were reacted with each other. Target compound in the amount of 56 mg (40%) was obtained by following the procedure described in Example 1.
¹H NMR (400 MHz, DMSO-d₆) δ 9.89 (br s, 1H), 9.78 (br s, 1H), 9.07 (br s, 1H), 8.42-8.29 (m, 2H), 8.02 (d, 1H, J=7.5 Hz), 7.29-7.02 (m, 4H), 4.78 (s, 2H), 3.68-3.55 (m, 0.3H), 3.49-3.00 (m, 6H), 3.00-2.86 (m, 0.7H), 2.39 (s, 3H), 2.02-1.88 (m, 2H), 1.88-1.39 (m, 6H), 1.28 (d, 2.1H, J=6.2 Hz), 1.23 (d, 0.9H, J=6.5 Hz).

Example 95

Synthesis of 1-(2-{[2-(2-methyl-benzyl)-1,3-dioxo-2,3-dihydro-1H-isoindol-5-carbonyl]-amino}-ethyl)-pyrrolidinium chloride (Compound 95)

2-(2-methyl-benzyl)-1,3-dioxo-2,3-dihydro-1H-isoindol-5-carboxylic acid (100 mg, 0.338 mmol) and 2-pyrrolidin-1-yl-ethylamine (86 μL, 0.677 mmol) were reacted with each other. Target compound in the amount of 57 mg (39%) was obtained by following the procedure described in Example 1.
¹H NMR (400 MHz, DMSO-d₆) δ 10.21 (br s, 1H), 9.19 (t, 1H, J=5.5 Hz), 8.42-8.31 (m, 2H), 8.03 (d, 1H, J=7.7 Hz), 7.22-7.03 (m, 4H), 4.78 (s, 2H), 3.73-3.53 (m, 4H), 3.42-3.25 (m, 2H), 3.11-2.94 (m, 2H), 2.39 (s, 3H), 2.10-1.96 (m, 2H), 1.96-1.78 (m, 2H).

Example 96

Synthesis of 1-(3-{[2-(2-methyl-benzyl)-1,3-dioxo-2,3-dihydro-1H-isoindol-5-carbonyl]-amino}-propyl)-pyrrolidinium chloride (Compound 96)

2-(2-methyl-benzyl)-1,3-dioxo-2,3-dihydro-1H-isoindol-5-carboxylic acid (100 mg, 0.338 mmol) and 3-pyrrolidin-1-yl-propylamine (86 µL, 0.677 mmol) were reacted with each other. Target compound in the amount of 79 mg (53%) was obtained by following the procedure described in Example 1.
$^1$H NMR (400 MHz, DMSO-d$_6$) δ 10.43 (br s, 1H), 9.06 (t, 1H, J=5.3 Hz), 8.39-8.28 (m, 2H), 8.02 (d, 1H, J=7.6 Hz), 7.25-7.04 (m, 4H), 4.78 (s, 2H), 3.60-3.47 (m, 2H), 3.47-3.31 (m, 4H), 3.22-3.10 (m, 2H), 3.04-2.86 (m, 2H), 2.39 (s, 3H), 2.08-1.78 (m, 6H).

Example 97

Synthesis of 4-(2-{[2-(2-methyl-benzyl)-1,3-dioxo-2,3-dihydro-1H-isoindol-5-carbonyl]-amino}-ethyl)-4-morpholinium chloride (Compound 97)

2-(2-methyl-benzyl)-1,3-dioxo-2,3-dihydro-1H-isoindol-5-carboxylic acid (100 mg, 0.338 mmol) and 2-morpholinoethane amine (87 µL, 0.677 mmol) were reacted with each other. Target compound in the amount of 143 mg (95%) was obtained by following the procedure described in Example 1.
$^1$H NMR (400 MHz, DMSO-d$_6$) δ 10.38 (br s, 1H), 9.20 (br s, 1H), 8.42-8.33 (m, 2H), 8.04 (d, 1H, J=7.7 Hz), 7.28-7.05 (m, 4H), 4.78 (s, 2H), 4.10-3.92 (m, 2H), 3.82-3.62 (m, 4H), 3.59-3.45 (m, 2H), 3.40-3.28 (m, 2H), 3.21-3.05 (m, 2H), 2.39 (s, 3H).

Example 98

Synthesis of 4-(3-{[2-(2-methyl-benzyl)-1,3-dioxo-2,3-dihydro-1H-isoindol-5-carbonyl]-amino}-propyl)-4-morpholinium chloride (Compound 98)

2-(2-methyl-benzyl)-1,3-dioxo-2,3-dihydro-1H-isoindol-5-carboxylic acid (100 mg, 0.338 mmol) and 3-morpholin-1-yl-propylamine (96 µL, 0.677 mmol) were reacted with each other. Target compound in the amount of 67 mg (43%) was obtained by following the procedure described in Example 1.
$^1$H NMR (400 MHz, DMSO-d$_6$) δ 10.64 (br s, 1H), 9.07 (br s, 1H), 8.34 (s, 1H), 8.32 (d, 1H, J=10.2 Hz), 8.01 (d, 1H, J=7.6 Hz), 7.28-7.03 (m, 4H), 4.77 (s, 2H), 4.07-3.90 (m, 2H), 3.85-3.70 (m, 2H), 3.51-3.33 (m, 4H), 3.25-3.13 (m, 2H), 3.13-3.00 (m 2H), 2.38 (s, 3H), 2.10-1.93 (m, 2H).

Example 99

Synthesis of 1-(2-{[2-(3-methyl-benzyl)-1,3-dioxo-2,3-dihydro-1H-isoindol-5-carbonyl]-amino}-ethyl)-piperidinium chloride (Compound 99)

2-(3-methyl-benzyl)-1,3-dioxo-2,3-dihydro-1H-isoindol-5-carboxylic acid (100 mg, 0.338 mmol) and 2-piperidin-1-yl-ethylamine (97 µL, 0.677 mmol) were reacted with each other. Target compound in the amount of 98 mg (66%) was obtained by following the procedure described in Example 1.
$^1$H NMR (400 MHz, DMSO-d$_6$) δ 10.33 (br s, 1H), 9.30 (br s, 1H), 8.35 (br s, 2H), 7.98 (d, 1H, J=7.9 Hz), 7.26-6.99 (m, 4H), 4.73 (s, 2H), 3.80-3.63 (m, 2H), 3.56-3.41 (m, 2H), 3.29-3.14 (m, 2H), 2.98-2.80 (m, 2H), 2.24 (s, 3H), 1.87-1.60 (m, 5H), 1.42-1.28 (m, 1H).

Example 100

Synthesis of 2-methyl-1-(3-{[2-(3-methyl-benzyl)-1,3-dioxo-2,3-dihydro-1H-isoindol-5-carbonyl]-amino}-propyl)-piperidinium chloride (Compound 100)

2-(3-methyl-benzyl)-1,3-dioxo-2,3-dihydro-1H-isoindol-5-carboxylic acid (100 mg, 0.338 mmol) and 3-(2-methylpiperidin-1-yl)propan-1-amine (118 µL, 0.677 mmol) were reacted with each other. Target compound in the amount of 122 mg (77%) was obtained by following the procedure described in Example 1.
$^1$H NMR (400 MHz, DMSO-d$_6$) δ 10.29 (br s, 1H), 9.10 (br s, 1H), 8.31 (br s, 2H), 7.98 (d, 1H, J=6.7 Hz), 7.27-6.98 (m, 4H), 4.73 (s, 2H), 3.65-3.50 (m, 0.3H), 3.48-3.27 (m, 2H), 3.27-2.97 (m, 4H), 2.97-2.78 (m, 0.7H), 2.25 (s, 3H), 2.08-1.88 (m, 2H), 1.88-1.54 (m, 5H), 1.54-1.35 (m, 1H), 1.27 (d, 2.1H, 5.0 Hz), 1.21 (d, 0.9H, J=5.5 Hz).

Example 101

Synthesis of 1-(2-{[2-(3-methyl-benzyl)-1,3-dioxo-2,3-dihydro-1H-isoindol-5-carbonyl]-amino}-ethyl)-pyrrolidinium chloride (Compound 101)

2-(3-methyl-benzyl)-1,3-dioxo-2,3-dihydro-1H-isoindol-5-carboxylic acid (100 mg, 0.338 mmol) and 2-pyrrolidin-1-yl-ethylamine (86 µL, 0.677 mmol) were reacted with each other. Target compound in the amount of 91 mg (63%) was obtained by following the procedure described in Example 1.
$^1$H NMR (400 MHz, DMSO-d$_6$) δ 10.05 (br s, 1H), 9.16 (t, 1H, J=5.4 Hz), 8.40-8.27 (m, 2H), 8.01 (d, 1H, J=7.7 Hz), 7.22 (t, 1H, J=7.5 Hz), 7.16-6.99 (m, 3H), 4.74 (s, 2H), 3.73-3.52 (m, 4H), 3.41-3.25 (m, 2H), 3.11-2.94 (m, 2H), 2.26 (s, 3H), 2.21-1.92 (m, 2H), 1.92-1.73 (m, 2H).

Example 102

Synthesis of 1-(3-{[2-(3-methyl-benzyl)-1,3-dioxo-2,3-dihydro-1H-isoindol-5-carbonyl]-amino}-propyl)-pyrrolidinium chloride (Compound 102)

2-(3-methyl-benzyl)-1,3-dioxo-2,3-dihydro-1H-isoindol-5-carboxylic acid (100 mg, 0.338 mmol) and 3-pyrrolidin-1-yl-propylamine (117 µL, 1.077 mmol) were reacted with each other. Target compound in the amount of 96 mg (64%) was obtained by following the procedure described in Example 1.
$^1$H NMR (400 MHz, DMSO-d$_6$) δ 10.28 (br s, 1H), 9.04 (t, 1H, J=5.2 Hz), 8.37-8.21 (m, 2H), 8.00 (d, 1H, J=7.6 Hz), 7.21 (t, 1H, J=7.4 Hz), 7.13-6.97 (m, 3H), 4.75 (s, 2H), 3.60-3.48 (m, 2H), 3.48-3.30 (m, 2H), 3.21-3.09 (m, 2H), 3.02-2.83 (m, 2H), 2.26 (s, 3H), 2.10-1.79 (m, 6H).

Example 103

Synthesis of 4-(2-{[2-(3-methyl-benzyl)-1,3-dioxo-2,3-dihydro-1H-isoindol-5-carbonyl]-amino}-ethyl)-4-morpholinium chloride (Compound 103)

2-(3-methyl-benzyl)-1,3-dioxo-2,3-dihydro-1H-isoindol-5-carboxylic acid (100 mg, 0.338 mmol) and 2-morpholinoethane amine (87 µL, 0.677 mmol) were reacted with each other. Target compound in the amount of 150 mg (99%) was obtained by following the procedure described in Example 1.

$^1$H NMR (400 MHz, DMSO-d$_6$) δ 10.73 (br s, 1H), 9.24 (br s, 1H), 8.41-8.30 (m, 2H), 8.00 (d, 1H, J=7.4 Hz), 7.21 (t, 1H, J=7.5 Hz), 7.12-6.96 (m, 3H), 4.74 (s, 2H), 4.02-3.90 (m, 2H), 3.82-3.65 (m, 4H), 3.60-3.47 (m, 2H), 3.40-3.29 (m, 2H), 3.20-3.02 (m, 2H), 2.26 (s, 3H).

Example 104

Synthesis of 4-(3-{[2-(3-methyl-benzyl)-1,3-dioxo-2,3-dihydro-1H-isoindol-5-carbonyl]-amino}-propyl)-4-morpholinium chloride (Compound 104)

2-(3-methyl-benzyl)-1,3-dioxo-2,3-dihydro-1H-isoindol-5-carboxylic acid (100 mg, 0.338 mmol) and 3-morpholin-1-yl-propylamine (96 μL, 0.677 mmol) were reacted with each other. Target compound in the amount of 112 mg (72%) was obtained by following the procedure described in Example 1.

$^1$H NMR (400 MHz, DMSO-d$_6$) δ 10.49 (br s, 1H), 9.04 (t, 1H, J=5.4 Hz), 8.34-8.21 (m, 2H), 8.00 (d, 1H, J=7.7 Hz), 7.20 (t, 1H, J=7.5 Hz), 7.17-7.00 (m, 3H), 4.70 (s, 2H), 4.04-3.86 (m, 2H), 3.80-3.63 (m, 2H), 3.48-3.25 (m, 4H), 3.20-2.96 (m, 4H), 2.26 (s, 3H), 2.04-1.88 (m, 2H).

Example 105

Synthesis of 1-(2-{[2-(4-methyl-benzyl)-1,3-dioxo-2,3-dihydro-1H-isoindol-5-carbonyl]-amino}-ethyl)-piperidinium chloride (Compound 105)

2-(4-methyl-benzyl)-1,3-dioxo-2,3-dihydro-1H-isoindol-5-carboxylic acid (100 mg, 0.338 mmol) and 2-piperidin-1-yl-ethylamine (97 μL, 0.677 mmol) were reacted with each other. Target compound in the amount of 107 mg (71%) was obtained by following the procedure described in Example 1.

$^1$H NMR (400 MHz, DMSO-d$_6$) δ 10.31 (br s, 1H), 9.30 (t, 1H, J=5.4 Hz), 8.39-8.27 (m, 2H), 7.98 (d, 1H, J=8.2 Hz), 7.19 (d, 2H, J=8.0 Hz), 7.12 (d, 2H, J=7.9 Hz), 4.73 (s, 2H), 3.78-3.62 (m, 2H), 3.54-3.40 (m, 2H), 3.28-3.13 (m, 2H), 2.97-2.78 (m, 2H), 2.24 (s, 3H), 1.89-1.60 (m, 5H), 1.47-1.27 (m, 1H).

Example 106

Synthesis of 1-(3-{[2-(4-methyl-benzyl)-1,3-dioxo-2,3-dihydro-1H-isoindol-5-carbonyl]-amino}-propyl)-piperidinium chloride (Compound 106)

2-(4-methyl-benzyl)-1,3-dioxo-2,3-dihydro-1H-isoindol-5-carboxylic acid (100 mg, 0.339 mmol) and 3-(2-methylpiperidin-1-yl)propan-1-amine (148 μL, 0.847 mmol) were reacted with each other. Target compound in the amount of 103 mg (67%) was obtained by following the procedure described in Example 1.

$^1$H NMR (400 MHz, DMSO-d$_6$) δ 9.81 (br s, 0.3H), 9.72 (br s, 0.7H), 9.05-8.92 (m, 1H), 8.35-8.23 (m, 2H), 7.99 (d, 1H, J=8.2 Hz), 7.19 (d, 2H, 1=8.1 Hz), 7.12 (d, 2H, J=8.0 Hz), 4.73 (s, 2H), 3.65-3.53 (m, 0.3H), 3.43-3.31 (m, 2H), 3.31-2.99 (m, 4H), 2.99-2.85 (m, 0.7H), 2.25 (s, 3H), 2.00-1.87 (m, 2H), 1.87-1.49 (m, 6H), 1.26 (d, 1H, J=6.3 Hz), 1.21 (d, 1H, J=6.8 Hz).

Example 107

Synthesis of 1-(2-{[2-(4-methyl-benzyl)-1,3-dioxo-2,3-dihydro-1H-isoindol-5-carbonyl]-amino}-ethyl)-pyrrolidinium chloride (Compound 107)

2-(4-methyl-benzyl)-1,3-dioxo-2,3-dihydro-1H-isoindol-5-carboxylic acid (100 mg, 0.339 mmol) and 2-pyrrolidin-1-yl-ethylamine (107 μL, 0.847 mmol) were reacted with each other. Target compound in the amount of 84 mg (58%) was obtained by following the procedure described in Example 1.

$^1$H NMR (400 MHz, DMSO-d$_6$) δ 10.48 (br s, 1H), 9.04 (br s, 1H), 8.36-8.23 (m, 2H), 7.99 (d, 1H, J=7.6 Hz), 7.19 (d, 2H, J=8.0 Hz), 7.12 (d, 2H, J=8.0 Hz), 4.73 (s, 2H), 4.04-3.89 (m, 2H), 3.81-3.66 (m, 2H), 3.49-3.29 (m, 4H), 3.20-2.97 (m, 4H), 2.25 (s, 3H), 2.06-1.90 (m, 2H).

Example 108

Synthesis of 1-(3-{[2-(4-methyl-benzyl)-1,3-dioxo-2,3-dihydro-1H isoindol-5-carbonyl]-amino}-propyl)-pyrrolidinium chloride (Compound 108)

2-(4-methyl-benzyl)-1,3-dioxo-2,3-dihydro-1H-isoindol-5-carboxylic acid (100 mg, 0.338 mmol) and 3-pyrrolidin-1-yl-propylamine (86 μL, 0.677 mmol) were reacted with each other. Target compound in the amount of 148 mg (99%) was obtained by following the procedure described in Example 1.

$^1$H NMR (400 MHz, DMSO-d$_6$) δ 10.44 (br s, 1H), 9.04 (t, 1H, J=5.4 Hz), 8.33-8.21 (m, 2H), 7.99 (d, 1H, J=7.6 Hz), 7.19 (d, 2H, J=7.8 Hz), 7.12 (d, 2H, J=7.9 Hz), 4.73 (s, 2H), 3.59-3.42 (m, 2H), 3.42-3.30 (m, 4H), 3.21-3.09 (m, 2H), 3.02-2.88 (m, 2H), 2.25 (s, 3H), 2.02-1.73 (m, 6H).

Example 109

Synthesis of 4-(2-{[2-(4-methyl-benzyl)-1,3-dioxo-2,3-dihydro-1H-isoindol-5-carbonyl]-amino}-ethyl)-4-morpholinium chloride (Compound 109)

2-(4-methyl-benzyl)-1,3-dioxo-2,3-dihydro-1H-isoindol-5-carboxylic acid (100 mg, 0.338 mmol) and 2-morpholinoethane amine (87 μL, 0.677 mmol) were reacted with each other. Target compound in the amount of 86 mg (56%) was obtained by following the procedure described in Example 1.

$^1$H NMR (400 MHz, DMSO-d$_6$) δ 10.54 (br s, 1H), 9.19 (br s, 1H), 8.35 (s, 1H), 8.32 (d, 1H, J=7.8 Hz), 8.01 (d, 1H, J=7.9 Hz), 7.20 (d, 2H, J=8.0 Hz), 7.13 (d, 2H, J=8.0 Hz), 4.74 (s, 2H), 4.04-3.88 (m, 2H), 3.83-3.60 (m, 4H), 3.60-3.44 (m, 2H), 3.40-3.25 (m, 2H), 3.20-3.00 (m, 2H), 2.25 (s, 3H).

Example 110

Synthesis of 4-(3-{[2-(4-methyl-benzyl)-1,3-dioxo-2,3-dihydro-1H-isoindol-5-carbonyl]-amino}-propyl)-4-morpholinium chloride (Compound 110)

2-(4-methyl-benzyl)-1,3-dioxo-2,3-dihydro-1H-isoindol-5-carboxylic acid (100 mg, 0.338 mmol) and 3-morpholin-1-yl-propylamine (96 μL, 0.677 mmol) were reacted with each other. Target compound in the amount of 155 mg (99%) was obtained by following the procedure described in Example 1.

¹H NMR (400 MHz, DMSO-d₆) δ 10.69 (br s, 1H), 9.05 (t, 1H, J=5.1 Hz), 8.31 (s, 1H), 8.30 (d, 1H, J=7.7 Hz), 8.99 (d, 1H, J=7.6 Hz), 7.19 (d, 2H, J=7.9 Hz), 7.12 (d, 2H, J=7.9 Hz), 4.79 (s, 2H), 4.00-3.88 (m, 2H), 3.81-3.68 (m, 2H), 3.45-3.30 (m, 4H), 3.19-2.98 (m, 4H), 2.25 (s, 3H), 2.03-1.88 (m, 2H).

Example 111

Synthesis of 1-(2-{[2-(2-methoxy-benzyl)-1,3-dioxo-2,3-dihydro-1H-isoindol-5-carbonyl]-amino}-ethyl)-piperidinium chloride (Compound 111)

2-(2-methoxy-benzyl)-1,3-dioxo-2,3-dihydro-1H-isoindol-5-carboxylic acid (100 mg, 0.321 mmol) and 2-piperidin-1-yl-ethylamine (92 μL, 0.642 mmol) were reacted with each other. Target compound in the amount of 39 mg (26%) was obtained by following the procedure described in Example 1.

¹H NMR (400 MHz, DMSO-d₆) δ 10.33 (br s, 1H), 9.30 (s, 1H), 8.42-8.31 (m, 2H), 7.99 (d, 1H, J=8.1 Hz), 7.28-7.18 (m, 1H), 7.06-6.92 (m, 2H), 6.87-6.78 (m, 1H), 4.73 (s, 2H), 3.79 (s, 3H), 3.78-3.62 (m, 2H), 3.56-3.41 (m, 2H), 3.28-3.12 (m, 2H), 3.00-2.78 (m, 2H), 1.89-1.58 (m, 4H), 1.43-1.23 (m, 1H).

Example 112

Synthesis of 1-(3-{[2-(2-methoxy-benzyl)-1,3-dioxo-2,3-dihydro-1H-isoindol-5-carbonyl]-amino}-propyl)-2-methyl-piperidinium chloride (Compound 112)

2-(2-methoxy-benzyl)-1,3-dioxo-2,3-dihydro-1H-isoindol-5-carboxylic acid (100 mg, 0.321 mmol) and 3-(2-methylpiperidin-1-yl)propan-1-amine (112 μL, 0.642 mmol) were reacted with each other. Target compound in the amount of 140 mg (90%) was obtained by following the procedure described in Example 1.

¹H NMR (400 MHz, DMSO-d₆) δ 10.02 (br s, 1H), 9.08 (s, 1H), 8.34-8.32 (m, 2H), 8.02 (d, 1H, J=7.9 Hz), 7.29-6.85 (m, 4H), 4.75 (s, 2H), 3.82 (s, 3H), 3.62 (br s, 0.3H), 3.60-3.36 (m, 2.7H), 3.28-2.92 (m, 3.3H), 2.90-2.78 (m, 0.7H), 2.05-1.55 (m, 7H), 1.55-1.35 (m, 1H), 1.29 (d, 2.1H, J=6.2 Hz), 1.23 (d, 0.9H, J=6.7 Hz).

Example 113

Synthesis of 1-(2-{[2-(2-methoxy-benzyl)-1,3-dioxo-2,3-dihydro-1H-isoindol-5-carbonyl]-amino}-ethyl)-pyrrolidinium chloride (Compound 113)

2-(2-methoxy-benzyl)-1,3-dioxo-2,3-dihydro-1H-isoindol-5-carboxylic acid (100 mg, 0.321 mmol) and 2-pyrrolidin-1-yl-ethylamine (81 μL, 0.642 mmol) were reacted with each other. Target compound in the amount of 115 mg (81%) was obtained by following the procedure described in Example 1.

¹H NMR (400 MHz, DMSO-d₆) δ 10.18 (br s, 1H), 9.18 (t, 1H, J=5.3 Hz), 8.39-8.34 (m, 2H), 8.04 (d, 1H, J=7.7 Hz), 7.29-6.84 (m, 4H), 4.76 (s, 2H), 3.82 (s, 3H), 3.67-3.63 (m, 4H), 3.40-3.36 (m, 2H), 3.06 (t, 2H, J=10.3 Hz), 2.03 (br s, 2H), 1.91-1.85 (m, 2H).

Example 114

Synthesis of 1-(3-{[2-(2-methoxy-benzyl)-1,3-dioxo-2,3-dihydro-1H-isoindol-5-carbonyl]-amino}-propyl)-pyrrolidinium chloride (Compound 114)

2-(2-methoxy-benzyl)-1,3-dioxo-2,3-dihydro-1H-isoindol-5-carboxylic acid (100 mg, 0.321 mmol) and 3-pyrrolidin-1-yl-propylamine (81 μL, 0.642 mmol) were reacted with each other. Target compound in the amount of 116 mg (79%) was obtained by following the procedure described in Example 1.

¹H NMR (400 MHz, DMSO-d₆) δ 10.28 (br s, 1H), 9.04 (t, 1H, J=5.6 Hz), 8.35-8.31 (m, 2H), 8.02 (d, 1H, J=7.7 Hz), 7.29-6.84 (m, 4H), 4.76 (s, 2H), 3.82 (s, 3H), 3.53 (br s, 2H), 3.42-3.37 (m, 2H), 3.18 (br s, 2H), 2.98 (br s, 2H), 2.00-1.86 (m, 6H).

Example 115

Synthesis of 4-(2-{[2-(2-methoxy-benzyl)-1,3-dioxo-2,3-dihydro-1H-isoindol-5-carbonyl]-amino}-ethyl)-4-morpholinium chloride (Compound 115)

2-(2-methoxy-benzyl)-1,3-dioxo-2,3-dihydro-1H-isoindol-5-carboxylic acid (100 mg, 0.321 mmol) and 2-morpholinoethane amine (84 μL, 0.642 mmol) were reacted with each other. Target compound in the amount of 133 mg (90%) was obtained by following the procedure described in Example 1.

¹H NMR (400 MHz, DMSO-d₆) δ 10.52 (br s, 1H), 9.22 (br s, 1H), 8.38-8.32 (m, 2H), 8.03 (d, 1H, J=8.3 Hz), 7.29-6.84 (m, 4H), 4.76 (s, 2H), 4.00 (d, 2H, J=11.5 Hz), 3.82 (s, 3H), 3.78-3.70 (m, 4H), 3.55 (d, 4H, J=11.7 Hz), 3.14 (d, 2H, J=8.8 Hz).

Example 116

Synthesis of 4-(3-{[2-(2-methoxy-benzyl)-1,3-dioxo-2,3-dihydro-1H-isoindol-5-carbonyl]-amino}-propyl)-4-morpholinium chloride (Compound 116)

2-(2-methoxy-benzyl)-1,3-dioxo-2,3-dihydro-1H-isoindol-5-carboxylic acid (100 mg, 0.321 mmol) and 3-morpholin-1-yl-propylamine (94 μL, 0.642 mmol) were reacted with each other. Target compound in the amount of 101 mg (66%) was obtained by following the procedure described in Example 1.

¹H NMR (400 MHz, DMSO-d₆) δ 10.62 (br s, 1H), 9.07 (t, 1H, J=5.5 Hz), 8.35-8.31 (m, 2H), 8.02 (d, 1H, J=7.7 Hz), 7.29-6.84 (m, 4H), 4.76 (s, 2H), 3.96 (d, 2H, J=11.0 Hz), 3.82 (s, 3H), 3.80-3.73 (m, 2H), 3.44-3.35 (m, 2H), 3.17-3.02 (m, 4H), 2.02-1.96 (m, 2H).

Example 117

Synthesis of 1-(2-{[2-(3-methoxy-benzyl)-1,3-dioxo-2,3-dihydro-1H-isoindol-5-carbonyl]-amino}-ethyl)-piperidinium chloride (Compound 117)

2-(3-methoxy-benzyl)-1,3-dioxo-2,3-dihydro-1H-isoindol-5-carboxylic acid (100 mg, 0.321 mmol) and 2-piperidin-1-yl-ethylamine (92 μL, 0.642 mmol) were reacted with each other. Target compound in the amount of 134 mg (91%) was obtained by following the procedure described in Example 1.

¹H NMR (400 MHz, DMSO-d₆) δ 10.37 (br s, 1H), 9.33 (t, 1H, J=5.4 Hz), 8.38 (s, 1H), 8.37 (d, 1H, J=5.0 Hz), 8.00 (d, 1H, J=8.1 Hz), 7.23 (t, 1H, J=13.8 Hz), 6.91-6.78 (m, 3H), 4.75 (s, 2H), 3.71 (s, 3H), 3.77-3.64 (m, 2H), 3.58-3.46 (m, 2H), 3.28-3.17 (m, 2H), 2.98-2.81 (m, 2H), 1.88-1.61 (m, 5H), 1.47-1.30 (m, 1H).

Example 118

Synthesis of 1-(3-{[2-(3-methoxy-benzyl)-1,3-dioxo-2,3-dihydro-1H-isoindol-5-carbonyl]-amino}-propyl)-2-methyl-piperidinium chloride (Compound 118)

2-(3-methoxy-benzyl)-1,3-dioxo-2,3-dihydro-1H-isoindol-5-carboxylic acid (100 mg, 0.321 mmol) and 3-(2-methylpiperidin-1-yl)propan-1-amine (112 μL, 0.642 mmol) were reacted with each other. Target compound in the amount of 124 mg (80%) was obtained by following the procedure described in Example 1.

¹H NMR (400 MHz, DMSO-d₆) δ 9.68 (br s, 1H), 9.06 (s, 1H), 8.32 (d, 2H, J=9.9 Hz), 8.02 (d, 1H, J=7.7 Hz), 7.25 (t, 1H, J=7.7 Hz), 6.88-6.83 (m, 3H), 4.77 (s, 2H), 3.73 (s, 3H), 3.58 (br s, 0.3H), 3.50-3.36 (m, 2.7H), 3.30-2.98 (m, 3.3H), 2.96-2.78 (m, 0.7H), 2.05-1.55 (m, 7H), 1.55-1.35 (m, 1H), 1.28 (d, 2.1H, J=6.3 Hz), 1.23 (d, 0.9H, J=6.8 Hz).

Example 119

Synthesis of 1-(2-{[2-(3-methoxy-benzyl)-1,3-dioxo-2,3-dihydro-1H-isoindol-5-carbonyl]-amino}-ethyl)-pyrrolidinium chloride (Compound 119)

2-(3-methoxy-benzyl)-1,3-dioxo-2,3-dihydro-1H-isoindol-5-carboxylic acid (100 mg, 0.321 mmol) and 2-pyrrolidin-1-yl-ethylamine (102 μL, 0.803 mmol) were reacted with each other. Target compound in the amount of 87 mg (61%) was obtained by following the procedure described in Example 1.

¹H NMR (400 MHz, DMSO-d₆) δ 10.32 (br s, 1H), 9.21 (t, 1H, J=5.4 Hz), 8.37 (s, 1H), 8.36 (d, 1H, J=9.0 Hz), 8.02 (d, 1H, J=7.7 Hz), 7.24 (t, 1H, J=7.8 Hz), 6.91-6.77 (m, 3H), 4.76 (s, 2H), 3.72 (s, 3H), 3.70-3.58 (m, 4H), 3.42-3.30 (m, 2H), 3.09-2.96 (m, 2H), 2.08-1.93 (m, 2H), 1.93-1.80 (m, 2H).

Example 120

Synthesis of 1-(3-{[2-(3-methoxy-benzyl)-1,3-dioxo-2,3-dihydro-1H-isoindol-5-carbonyl]-amino}-propyl)-pyrrolidinium chloride (Compound 120)

2-(3-methoxy-benzyl)-1,3-dioxo-2,3-dihydro-1H-isoindol-5-carboxylic acid (100 mg, 0.321 mmol) and 3-pyrrolidin-1-yl-propylamine (81 μL, 0.642 mmol) were reacted with each other. Target compound in the amount of 101 mg (68%) was obtained by following the procedure described in Example 1.

¹H NMR (400 MHz, DMSO-d₆) δ 10.16 (br s, 1H), 9.03 (t, 1H, J=5.5 Hz), 8.34-8.30 (m, 2H), 8.01 (d, 1H, J=7.7 Hz), 7.30-7.22 (m, 1H), 6.88-6.83 (m, 3H), 4.77 (s, 2H), 3.73 (s, 3H), 3.52 (br s, 2H), 3.41-3.36 (m, 2H), 3.17 (br s, 2H), 2.97 (br s, 2H), 2.00-1.85 (m, 6H).

Example 121

Synthesis of 4-(2-{[2-(3-methoxy-benzyl)-1,3-dioxo-2,3-dihydro-1H-isoindol-5-carbonyl]-amino}-ethyl)-4-morpholinium chloride (Compound 121)

2-(3-methoxy-benzyl)-1,3-dioxo-2,3-dihydro-1H-isoindol-5-carboxylic acid (100 mg, 0.321 mmol) and 2-morpholinoethane amine (105 μL, 0.803 mmol) were reacted with each other. Target compound in the amount of 63 mg (43%) was obtained by following the procedure described in Example 1.

¹H NMR (400 MHz, DMSO-d₆) δ 10.57 (br s, 1H), 9.21 (br s, 1H), 8.37 (s, 1H), 8.32 (d, 1H, J=10.4 Hz), 8.01 (d, 1H, J=7.6 Hz), 7.23 (t, 1H, J=7.8 Hz), 6.90-6.72 (m, 3H), 4.75 (s, 2H), 4.05-3.92 (m, 2H), 3.83-3.64 (m, 4H), 3.71 (s, 3H), 3.58-3.46 (m, 2H), 3.40-3.37 (m, 2H), 3.17-3.03 (m, 2H).

Example 122

Synthesis of 4-(3-{[2-(3-methoxy-benzyl)-1,3-dioxo-2,3-dihydro-1H-isoindol-5-carbonyl]-amino}-propyl)-4-morpholinium chloride (Compound 122)

2-(3-methoxy-benzyl)-1,3-dioxo-2,3-dihydro-1H-isoindol-5-carboxylic acid (100 mg, 0.321 mmol) and 3-morpholin-1-yl-propylamine (117 μL, 0.803 mmol) were reacted with each other. Target compound in the amount of 150 mg (98%) was obtained by following the procedure described in Example 1.

¹H NMR (400 MHz, DMSO-d₆) δ 10.44 (br s, 1H), 9.05 (t, 1H, J=5.5 Hz), 8.33 (s, 1H), 8.31 (d, 1H, J=6.6 Hz), 8.01 (d, 1H, J=7.8 Hz), 7.24 (t, 1H, J=7.8 Hz), 6.91-6.80 (m, 3H), 4.76 (s, 2H), 4.02-3.92 (m, 2H), 3.80-3.68 (m, 2H), 3.72 (s, 3H), 3.48-3.38 (m, 4H), 3.21-3.11 (m, 2H), 3.11-2.99 (m, 2H), 2.02-1.92 (m, 2H).

Example 123

Synthesis of 1-(2-{[2-(4-methoxy-benzyl)-1,3-dioxo-2,3-dihydro-1H isoindol-5-carbonyl]-amino}-ethyl)-piperidinium chloride (Compound 123)

2-(4-methoxy-benzyl)-1,3-dioxo-2,3-dihydro-1H-isoindol-5-carboxylic acid (100 mg, 0.321 mmol) and 2-piperidin-1-yl-ethylamine (55 μL, 0.385 mmol) were reacted with each other. Target compound in the amount of 35 mg (23%) was obtained by following the procedure described in Example 1.

¹H NMR (400 MHz, CDCl₃) δ 11.68 (br s, 1H), 9.48 (br s, 1H), 8.54 (br s, 2H), 7.39 (d, 2H, J=7.8), 6.85 (d, 2H, J=7.8), 4.79 (s, 2H), 3.98 (br s, 2H), 3.78 (s, 3H), 3.69 (br s, 2H), 2.77 (br s, 2H), 2.36 (br s, 2H), 2.14-1.76 (m, 6H).

Example 124

Synthesis of 1-(3-{[2-(4-methoxy-benzyl)-1,3-dioxo-2,3-dihydro-1H-isoindol-5-carbonyl]-amino}-propyl)-2-methyl-piperidinium chloride (Compound 124)

2-(4-methoxy-benzyl)-1,3-dioxo-2,3-dihydro-1H-isoindol-5-carboxylic acid (100 mg, 0.321 mmol) and 3-(2-methylpiperidin-1-yl)propan-1-amine (140 μL, 0.803 mmol) were reacted with each other. Target compound in the amount of 52 mg (34%) was obtained by following the procedure described in Example 1.

¹H NMR (400 MHz, DMSO-d₆) δ 9.70 (br s, 0.3H), 9.62 (br s, 0.7H), 9.08-8.94 (m, 1H), 8.31 (s, 1H), 8.30 (d, 1H, J=12.6 Hz), 8.00 (d, 1H, J=7.6 Hz), 7.26 (d, 2H, J=8.5 Hz), 6.88 (d, 1H, J=8.4 Hz), 4.72 (s, 2H), 3.71 (s, 3H), 3.63-3.52 (m, 0.3H), 3.44-3.29 (m, 2H), 3.29-2.98 (m, 4H), 2.98-2.81 (m, 0.7H), 2.04-1.47 (m, 9H), 1.26 (d, 2.1H, J=6.3 Hz), 1.22 (d, 0.9H, J=6.8 Hz).

Example 125

Synthesis of 1-(2-{[2-(4-methoxy-benzyl)-1,3-dioxo-2,3-dihydro-1H-isoindol-5-carbonyl]-amino}-ethyl)-pyrrolidinium chloride (Compound 125)

2-(4-methoxy-benzyl)-1,3-dioxo-2,3-dihydro-1H-isoindol-5-carboxylic acid (100 mg, 0.321 mmol) and 2-pyrrolidin-1-yl-ethylamine (102 µL, 0.803 mmol) were reacted with each other. Target compound in the amount of 77 mg (54%) was obtained by following the procedure described in Example 1.
¹H NMR (400 MHz, DMSO-d₆) δ 10.05 (br s, 1H), 9.62 (br s, 0.7H), 9.16 (t, 1H, J=5.4 Hz), 8.35 (s, 1H), 8.34 (d, 1H, J=9.0 Hz), 8.01 (d, 1H, J=7.7 Hz), 7.7.26 (d, 2H, J=8.5 Hz), 6.89 (d, 1H, J=8.6 Hz), 4.72 (s, 2H), 3.71 (s, 3H), 3.69-3.57 (m, 4H), 3.40-3.27 (m, 2H), 3.12-2.97 (m, 2H), 2.21-1.95 (m, 2H), 1.95-1.80 (m, 2H).

Example 126

Synthesis of 1-(3-{[2-(4-methoxy-benzyl)-1,3-dioxo-2,3-dihydro-1H-isoindol-5-carbonyl]-amino}-propyl)-pyrrolidinium chloride (Compound 126)

2-(4-methoxy-benzyl)-1,3-dioxo-2,3-dihydro-1H-isoindol-5-carboxylic acid (100 mg, 0.321 mmol) and 3-pyrrolidin-1-yl-propylamine (102 µL, 0.803 mmol) were reacted with each other. Target compound in the amount of 67 mg (46%) was obtained by following the procedure described in Example 1.
¹H NMR (400 MHz, DMSO-d₆) δ 9.93 (br s, 1H), 8.93 (t, 1H, J=5.4 Hz), 8.22 (s, 1H), 8.21 (d, 1H, J=7.7 Hz), 7.90 (d, 1H, J=8.0 Hz), 7.16 (d, 2H, J=8.6 Hz), 6.79 (d, 1H, J=8.6 Hz), 4.62 (s, 2H), 3.36 (s, 3H), 3.50-3.30 (m, 4H), 3.12-3.02 (m, 2H), 2.92-2.80 (m, 2H), 1.96-1.70 (m, 6H).

Example 127

Synthesis of 4-(2-{[2-(4-methoxy-benzyl)-1,3-dioxo-2,3-dihydro-1H-isoindol-5-carbonyl]-amino}-ethyl)-4-morpholinium chloride (Compound 127)

2-(4-methoxy-benzyl)-1,3-dioxo-2,3-dihydro-1H-isoindol-5-carboxylic acid (100 mg, 0.321 mmol) and 2-morpholinoethane amine (105 µL, 0.803 mmol) were reacted with each other. Target compound in the amount of 102 mg (69%) was obtained by following the procedure described in Example 1.
¹H NMR (400 MHz, DMSO-d₆) δ 10.61 (br s, 1H), 9.23 (br s, 1H), 8.36 (s, 1H), 8.33 (d, 1H, J=6.2 Hz), 8.01 (d, 1H, J=8.3 Hz), 7.26 (d, 2H, J=8.6 Hz), 6.89 (d, 1H, J=8.6 Hz), 4.72 (s, 2H), 4.04-3.93 (m, 2H), 3.85-3.68 (m, 4H), 3.72 (s, 3H), 3.59-3.49 (m, 2H), 3.42-3.27 (m, 2H), 3.20-3.06 (m, 2H).

Example 128

Synthesis of 4-(3-{[2-(4-methoxy-benzyl)-1,3-dioxo-2,3-dihydro-1H-isoindol-5-carbonyl]-amino}-propyl)-4-morpholinium chloride (Compound 128)

2-(4-methoxy-benzyl)-1,3-dioxo-2,3-dihydro-1H-isoindol-5-carboxylic acid (100 mg, 0.321 mmol) and 3-morpholin-1-yl-propylamine (117 µL, 0.803 mmol) were reacted with each other. Target compound in the amount of 132 mg (86%) was obtained by following the procedure described in Example 1.
¹H NMR (400 MHz, DMSO-d₆) δ 10.41 (br s, 1H), 9.04 (br s, 1H), 8.31 (s, 1H), 8.29 (d, 1H, J=9.0 Hz), 7.98 (d, 1H, J=7.8 Hz), 7.24 (d, 2H, J=8.6 Hz), 6.67 (d, 1H, J=8.6 Hz), 4.70 (s, 2H), 4.00-3.88 (m, 2H), 3.77-3.68 (m, 2H), 3.70 (s, 3H), 3.46-3.26 (m, 4H), 3.18-3.08 (m, 2H), 3.08-2.96 (m, 2H), 2.01-1.90 (m, 2H).

Example 129

Synthesis of 1-(2-{[2-(4-cyano-benzyl)-1,3-dioxo-2,3-dihydro-1H-isoindol-5-carbonyl]-amino}-ethyl)-piperidinium chloride (Compound 129)

2-(4-cyano-benzyl)-1,3-dioxo-2,3-dihydro-1H-isoindol-5-carboxylic acid (100 mg, 0.348 mmol) and 2-piperidin-1-yl-ethylamine (99 µL, 0.698 mmol) were reacted with each other. Target compound in the amount of 114 mg (72%) was obtained by following the procedure described in Example 1.
¹H NMR (400 MHz, DMSO-d₆) δ 10.29 (br s, 1H), 9.38-9.23 (m, 1H), 8.41-8.29 (m, 2H), 8.00 (d, 1H, J=8.2 Hz), 7.79 (d, 2H, J=8.2 Hz), 7.52 (d, 2H, J=8.2 Hz), 4.87 (s, 2H), 3.80-3.62 (m, 2H), 3.56-3.42 (m, 2H), 3.28-3.13 (m, 2H), 2.97-2.80 (m, 2H), 2.48 (s, 3H), 1.82-1.54 (m, 5H), 1.43-1.23 (m, 1H).

Example 130

Synthesis of 1-(3-{[2-(4-cyano-benzyl)-1,3-dioxo-2,3-dihydro-1H-isoindol-5-carbonyl]-amino}-propyl)-2-methyl-piperidinium chloride (Compound 130)

2-(4-cyano-benzyl)-1,3-dioxo-2,3-dihydro-1H-isoindol-5-carboxylic acid (114 mg, 0.371 mmol) and 3-(2-methylpiperidin-1-yl)propan-1-amine (129 µL, 0.741 mmol) were reacted with each other. Target compound in the amount of 163 mg (94%) was obtained by following the procedure described in Example 1.
¹H NMR (400 MHz, DMSO-d₆) δ 9.98 (br s, 0.3H), 9.90 (br s, 0.7H), 9.07 (t, 1H, J=5.1 Hz), 8.40-8.25 (m, 2H), 8.01 (d, 1H, J=8.2 Hz), 7.80 (d, 2H, J=8.4 Hz), 7.52 (d, 2H, J=8.3 Hz), 4.88 (s, 2H), 3.63-3.52 (m, 0.3H), 3.44-2.97 (m, 6H), 2.97-2.84 (m, 0.7H), 2.02-1.88 (m, 2H), 1.88-1.53 (m, 5H), 1.53-1.48 (m, 1H), 1.27 (d, 2.1H, J=6.3 Hz), 2.21 (d, 0.9H, J=6.8 Hz).

Example 131

Synthesis of 1-(2-{[2-(4-cyano-benzyl)-1,3-dioxo-2,3-dihydro-1H-isoindol-5-carbonyl]-amino}-ethyl)-pyrrolidinium chloride (Compound 131)

2-(4-cyano-benzyl)-1,3-dioxo-2,3-dihydro-1H-isoindol-5-carboxylic acid (100 mg, 0.327 mmol) and 2-pyrrolidin-1-yl-ethylamine (83 µL, 0.653 mmol) were reacted with each other. Target compound in the amount of 122 mg (85%) was obtained by following the procedure described in Example 1.

$^1$H NMR (400 MHz, DMSO-d$_6$) δ 10.14 (br s, 1H), 9.17 (t, 1H, J=7.3 Hz), 8.41-8.27 (m, 2H), 8.02 (d, 1H, J=7.7 Hz), 7.80 (d, 2H, J=8.3 Hz), 7.53 (d, 2H, J=8.3 Hz), 4.88 (s, 2H), 3.71-3.52 (m, 4H), 3.40-3.28 (m, 2H), 3.11-2.94 (m, 2H), 2.09-1.92 (m, 2H), 1.92-1.78 (m, 2H).

Example 132

Synthesis of 1-(3-{[2-(4-cyano-benzyl)-1,3-dioxo-2, 3-dihydro-1H-isoindol-5-carbonyl]-amino}-propyl)-pyrrolidinium chloride (Compound 132)

2-(4-cyano-benzyl)-1,3-dioxo-2,3-dihydro-1H-isoindol-5-carboxylic acid (100 mg, 0.327 mmol) and 3-pyrrolidin-1-yl-propylamine (83 μL, 0.653 mmol) were reacted with each other. Target compound in the amount of 70 mg (47%) was obtained by following the procedure described in Example 1.

$^1$H NMR (400 MHz, DMSO-d$_6$) δ 10.09 (br s, 1H), 9.02 (t, 1H, J=5.7), 8.38-8.22 (m, 2H), 8.01 (d, 1H, J=7.7 Hz), 7.80 (d, 2H, J=6.7 Hz), 7.52 (d, 2H, J=8.4 Hz), 4.88 (s, 2H), 3.59-3.47 (m, 2H), 3.42-3.32 (m, 2H), 3.21-3.09 (m, 2H), 3.04-2.90 (m, 2H), 2.06-1.79 (m, 6H).

Example 133

Synthesis of 4-(2-{[2-(4-cyano-benzyl)-1,3-dioxo-2, 3-dihydro-1H-isoindol-5-carbonyl]-amino}-ethyl)-4-morpholinium chloride (Compound 133)

2-(4-cyano-benzyl)-1,3-dioxo-2,3-dihydro-1H-isoindol-5-carboxylic acid (100 mg, 0.327 mmol) and 2-morpholinoethane amine (85 μL, 0.653 mmol) were reacted with each other. Target compound in the amount of 136 mg (91%) was obtained by following the procedure described in Example 1.

$^1$H NMR (400 MHz, DMSO-d$_6$) δ 10.48 (br s, 1H), 9.20 (br s, 1H), 8.36 (s, 1H), 8.35 (d, 1H, J=7.6 Hz), 8.02 (d, 1H, 8.4 Hz), 7.80 (d, 2H, J=8.4 Hz), 7.53 (d, 2H, J=8.4 Hz), 4.88 (s, 2H), 4.04-3.91 (m, 2H), 3.82-3.64 (m, 4H), 3.60-3.49 (m, 2H), 3.37-3.25 (m, 2H), 3.20-3.06 (m, 2H).

Example 134

Synthesis of 4-(3-{[2-(4-cyano-benzyl)-1,3-dioxo-2, 3-dihydro-1H-isoindol-5-carbonyl]-amino}-propyl)-4-morpholinium chloride (Compound 134)

2-(4-cyano-benzyl)-1,3-dioxo-2,3-dihydro-1H-isoindol-5-carboxylic acid (107 mg, 0.349 mmol) and 3-morpholin-1-yl-propylamine (102 μL, 0.698 mmol) were reacted with each other. Target compound in the amount of 155 mg (94%) was obtained by following the procedure described in Example 1.

$^1$H NMR (400 MHz, DMSO-d$_6$) δ 10.23 (br s, 1H), 9.08 (br s, 1H), 8.37-8.22 (m, 2H), 8.01 (d, 1H, J=7.6 Hz), 7.80 (d, 2H, J=8.2 Hz), 7.52 (d, 2H, J=8.2 Hz), 4.88 (s, 2H), 4.02-3.87 (m, 2H), 3.78-3.59 (m, 2H), 3.49-3.31 (m, 4H), 3.21-2.97 (m, 4H), 2.03-1.87 (m, 2H).

Meanwhile, novel compounds of Formula (1) herein may be formulated in various forms as described below, which in no way limits the scope of the claimed invention.

Formulation Example 1

Tablets (Direct Pressurization)

5.0 mg of active ingredient was sieved and admixed with 14.1 mg of lactose, 0.8 mg of crospovidone USNF and 0.1 mg of magnesium stearate, followed by mixing and pressurizing, thereby providing tablets.

Formulation Example 2

Tablets (Wet Granulation)

5.0 mg of active ingredient was sieved and admixed with 16.0 mg of lactose and 4.0 mg of starch. An appropriate amount of aqueous solution of polysorbate 80 (0.3 mg) was added for granulation. The granules were dried, sieved and admixed with 2.7 mg of colloidal silicon dioxide and 2.0 mg of magnesium stearate. The granules were pressurized to provide tablets.

Formulation Example 3

Powders and Capsules 5.0 mg of active ingredient was sieved and admixed with 14.8 mg of lactose, 10.0 mg of poly(vinyl pyrrolidone) and 0.2 mg of magnesium stearate. The mixture was filled in No. 5 gelatine capsules by using a proper device.

Formulation Example 4

Injections

Injections were prepared by incorporating 100 mg of active ingredient, 180 mg of mannitol and 26 mg of Na$_2$HPO$_4$.12H$_2$O in 2974 mg of distilled water.

Meanwhile, the antagonistic activity of the novel compound of Formula (1) herein against T-type calcium channel was tested as described below. The synthesized compounds were tested for the activity against T-type calcium channel with FDSS6000. Compounds with good activity were selected and IC$_{50}$ values were exactly obtained by using electrophysiological whole cell patch clamp method.

Experimental Example 1

Screening of Activity Against T-Type Calcium Channel with FDSS6000

HEK293 cells which stably express both α$_{1G}$ and Kir2.1 subunits were grown in Dulbecco's modified Eagle's medium supplemented with 10% (v/v) fetal bovine serum, penicillin (100 U/mL), streptomycin (100 μg/mL), geneticin (500 μg/mL), and +puromycin (I μg/mL) at 37° C. in a humid atmosphere of 5% CO$_2$ and 95% air. Cells were seeded into 96-well black wall clear bottom plates at a density of 4×10$^4$ cells/well and were used the next day for high-throughput screening (HTS) FDSS6000 assay. For FDSS6000 assay, cells were incubated for 60 min at room temperature with 5 μM fluo3/AM and 0.001% Pluronic F-127 in a HEPES-buffered solution composed of (in mM): 115 NaCl, 5.4 KCl, 0.8 MgCl$_2$, 1.8 CaCl$_2$, 20 HEPES, 13.8 glucose (pH 7.4). During the fluorescence-based FDSS6000 assay, cells in HEPES-buffered solution containing 10 mM CaCl$_2$ were pretreated with a certain concentration of test compounds and then treated with high concentration of KCl (70 mL). $\alpha_{1G}$ T-type $Ca^{2+}$ channels were activated by using high concentration of KCl (70 mM) and the increase in $[Ca^{2+}]_i$ by KCl-induced depolarization was detected. During the whole procedure, cells were washed using the BIO-TEK 96-well washer. All data were collected and analyzed using FDSS6000 and related software (Hamamatsu, Japan).

The $IC_{50}$ results of examining the inhibitory effects of the compounds herein selected with FDSS6000 on the calcium influx through the T-type calcium channel are provided in TABLEs 1 and 2.

TABLE 1

Inhibitory effect (%) of T-type calcium channel (100 μM)

| Compound no. | Inhibition (%) | Compound no. | Inhibition (%) |
|---|---|---|---|
| 1 | 28.1 | 2 | 33.8 |
| 3 | 20.3 | 4 | 38.7 |
| 5 | 22.7 | 6 | 22.3 |
| 7 | 40.6 | 8 | 36.8 |
| 9 | 39.7 | 10 | 32.5 |
| 11 | 22.7 | 12 | 21.1 |
| 13 | 43.0 | 14 | 44.2 |
| 15 | 25.8 | 16 | 30.0 |
| 17 | 29.2 | 18 | 22.7 |
| 19 | 45.7 | 20 | 44.7 |
| 21 | 19.4 | 22 | 19.3 |
| 23 | 14.5 | 24 | 21.4 |
| 25 | 38.2 | 26 | 52.7 |
| 27 | 44.5 | 28 | 45.6 |
| 29 | 53.8 | 30 | 33.6 |
| 32 | 22.3 | 33 | 64.5 |
| 39 | 39.4 | 46 | 31.4 |
| 48 | 31.4 | 49 | 72.4 |
| 50 | 69.6 | 51 | 48.4 |
| 52 | 45.8 | 53 | 42.5 |
| 54 | 38.5 | 55 | 79.9 |
| 56 | 78.8 | 57 | 65.5 |
| 58 | 70.6 | 59 | 30.2 |
| 60 | 60.8 | 61 | 85.5 |
| 62 | 83.5 | 63 | 73.4 |
| 64 | 65.9 | 65 | 59.8 |
| 66 | 59.8 | 68 | 78.2 |
| 69 | 84.7 | 70 | 67.5 |
| 72 | 46.4 | 73 | 64.8 |
| 93 | 90.4 | 94 | 84.8 |
| 97 | 69.8 | 98 | 55.2 |
| 99 | 89.7 | 111 | 69.5 |
| 112 | 75.1 | 113 | 55.1 |
| 114 | 53.0 | 115 | 51.1 |
| 116 | 48.8 | 117 | 69.8 |
| 118 | 71.1 | 119 | 56.3 |
| 120 | 63.7 | 121 | 57.6 |
| 122 | 56.6 | 123 | 64.3 |
| 124 | 77.7 | 125 | 65.2 |
| 126 | 73.8 | 127 | 51.7 |
| 128 | 52.9 | Mibefradil (10 μM) | 75.1 |

TABLE 2

Inhibitory effect (%) of T-type calcium channel (10 μM)

| Compound no. | Inhibition (%) | Compound no. | Inhibition (%) |
|---|---|---|---|
| 31 | NA[a] | 34 | 10.0 |
| 35 | 4.7 | 36 | 5.3 |
| 37 | 1.3 | 38 | 4.2 |
| 40 | 11.7 | 41 | 2.0 |
| 42 | NA[a] | 43 | NA[a] |
| 44 | NA[a] | 45 | NA[a] |
| 47 | NA[a] | 67 | 2.2 |
| 74 | 5.6 | 75 | 33.6 |
| 76 | 50.9 | 77 | 21.5 |
| 78 | 25.4 | 79 | 15.6 |
| 80 | 23.5 | 81 | 42.9 |
| 82 | 46.2 | 83 | 28.9 |
| 84 | 30.4 | 85 | 25.3 |
| 86 | 27.8 | 87 | 47.2 |
| 88 | 46.6 | 89 | 29.8 |
| 90 | 35.0 | 91 | 26.1 |
| 92 | 29.9 | 95 | 15.7 |
| 96 | 15.5 | 100 | 48.4 |
| 101 | 27.2 | 102 | 24.8 |
| 103 | 21.1 | 104 | 15.5 |
| 105 | 30.9 | 106 | 40.1 |
| 107 | 20.7 | 108 | 15.6 |
| 109 | 12.2 | 110 | 9.1 |
| 129 | NA[a] | 130 | 9.1 |
| 131 | 0.6 | 132 | NA[a] |
| 133 | NA[a] | 134 | NA[a] |
|  |  | Mibefradil | 75.1 |

[a]NA: Not Active

Experimental Example 2

Measuring T-Type Calcium Channel Activity in HEK293 Cell by Using Electrophysiological Whole Cell Patch Clamp Method For the recordings of $\alpha_{1G}$ T-type $Ca^{2+}$ currents, the standard whole-cell patch-clamp method was utilized as previously described. Briefly, borosilicate glass electrodes with a resistance of 3~4 MΩ were pulled and filled with the internal solution contained (in mM): 130 KCl, 11 EGTA, 5 Mg-ATP, and 10 HEPES (pH 7.4). The external solution contained (in mM): 140 NaCl, 2 $CaCl_2$, 10 HEPES, and 10 glucose (pH 7.4). $\alpha_{1G}$ T-type $Ca^{2+}$ currents were evoked every 15 s by a 50 ms depolarizing voltage step from −1.00 mV to −30 mV. The molar concentrations of test compounds required to produce 50% inhibition of peak currents ($IC_{50}$) were determined from fitting raw data into dose-response curves. The current recordings were obtained using an EPC-9 amplifier and Pulse/Pulsefit software program (HEKA, Germany).

The $IC_{50}$ results of examining the inhibitory effects of the compounds herein selected by electrophysiological methods on the calcium influx through the T-type calcium channel are provided in TABLE 3.

TABLE 3

Activity ($IC_{50}$) against T-type calcium channel

| Compound no. | $IC_{50}$ (μM) |
|---|---|
| 61 | 8.52 ± 0.75 |
| 69 | 2.03 ± 0.12 |
| 76 | 1.52 ± 0.19 |
| 82 | 1.81 ± 0.46 |
| 87 | 0.96 ± 0.07 |
| 88 | 0.93 ± 0.06 |
| 93 | 8.28 ± 2.95 |
| 94 | 2.07 ± 0.45 |
| 99 | 1.93 ± 0.23 |
| 100 | 1.84 ± 0.21 |
| Mibefradil | 0.84 |

As set forth above, 1,3-dioxoisoindole derivatives of Formula (1) herein or pharmaceutically acceptable salts thereof were ascertained to have superior antagonistic activ-

What is claimed is:

1. A 1,3-dioxoisoindole compound of Formula (1) or its pharmaceutically acceptable salts:

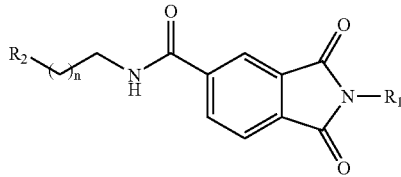

wherein $R_1$ is a phenyl or a benzyl group, optionally substituted with a moiety selected from the group consisting of a halogen atom, a $C_1$-$C_6$ alkoxy, a $C_1$-$C_6$ alkyl, and a cyano group; $R_2$ is a heterocyclic group selected from the group consisting of piperidinyl, pyrrolidinyl, morpholinyl, and piperazinyl group, the heterocyclic groups optionally substituted with a $C_1$-$C_6$ alkyl group; and n is 1 or 2.

2. The 1,3-dioxoisoindole compound of claim 1, wherein the $R_1$ is selected from the group consisting of phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 4-cyanophenyl, benzyl, 2-fluorobenzyl, 3-fluorobenzyl, 4-fluorobenzyl, 2-chlorobenzyl, 3-chlorobenzyl, 4-chlorobenzyl, 2-methylbenzyl, 3-methylbenzyl, 4-methylbenzyl, 2-methoxybenzyl, 3-methoxybenzyl, 4-methoxybenzyl, and 4-cyanobenzyl; $R_2$ is selected from the group consisting of 1-piperadinyl, 2-methylpiperidin-1-yl, 2-ethylpiperidin-1-yl, 1-pyrrolidinyl, 1-morpholinyl, and 4-methylpiperazin-1-yl groups; and n is 1 or 2.

3. The 1,3-dioxoisoindole compound of claim 1, which is selected from the group consisting of 1-{2-[(1,3-dioxo-2-phenyl-2,3-dihydro-1H-isoindol-5-carbonyl)-amino]-ethyl}-piperidinium chloride;
1-{3-[(1,3-dioxo-2-phenyl-2,3-dihydro-1H-isoindol-5-carbonyl)-amino]-propyl}-2-methyl-piperidinium chloride;
1-{2-[(1,3-dioxo-2-phenyl-2,3-dihydro-1H-isoindol-5-carbonyl)-amino]-ethyl}-pyrrolidinium chloride;
1-{3-[(1,3-dioxo-2-phenyl-2,3-dihydro-1H-isoindol-5-carbonyl)-amino]propyl}-pyrrolidinium chloride;
4-{2-[(1,3-dioxo-2-phenyl-2,3-dihydro-1H-isoindol-5-carbonyl)-amino]-ethyl}-4-morpholinium chloride;
4-{3-[(1,3-dioxo-2-phenyl-2,3-dihydro-1H-isoindol-5-carbonyl)-amino]-propyl}-4-morpholinium chloride;
1-(2-{[2-(2-fluoro-phenyl)-1,3-dioxo-2,3-dihydro-1H-isoindol-5-carbonyl]-amino}-ethyl)-piperidinium chloride;
1-(3-{[2-(2-fluoro-phenyl)-1,3-dioxo-2,3-dihydro-1H-isoindol-5-carbonyl]-amino}-propyl)-2-methyl-piperidinium chloride;
1-(2-{[2-(2-fluoro-phenyl)-1,3-dioxo-2,3-dihydro-1H-isoindol-5-carbonyl]-amino}-ethyl)-pyrrolidinium chloride;
1-(3-{[2-(2-fluoro-phenyl)-1,3-dioxo-2,3-dihydro-1H-isoindol-5-carbonyl]-amino}-propyl)-pyrrolidinium chloride;
4-(2-{[2-(2-fluoro-phenyl)-1,3-dioxo-2,3-dihydro-1H-isoindol-5-carbonyl]-amino}-ethyl)-4-morpholinium chloride;
4-(3-{[2-(2-fluoro-phenyl)-1,3-dioxo-2,3-dihydro-1H-isoindol-5-carbonyl]-amino}-propyl)-4-morpholinium chloride;
1-(2-{[2-(3-fluoro-phenyl)-1,3-dioxo-2,3-dihydro-1H-isoindol-5-carbonyl]-amino}-ethyl)-piperidinium chloride;
1-(3-{[2-(3-fluoro-phenyl)-1,3-dioxo-2,3-dihydro-1H-isoindol-5-carbonyl]-amino}-propyl)-2-methyl-piperidinium chloride;
1-(2-{[2-(3-fluoro-phenyl)-1,3-dioxo-2,3-dihydro-1H-isoindol-5-carbonyl]-amino}-ethyl)-pyrrolidinium chloride;
1-(3-{[2-(3-fluoro-phenyl)-1,3-dioxo-2,3-dihydro-1H-isoindol-5-carbonyl]-amino}-propyl)-pyrrolidinium chloride;
4-(2-{[2-(3-fluoro-phenyl)-1,3-dioxo-2,3-dihydro-1H-isoindol-5-carbonyl]-amino}-ethyl)-4-morpholinium chloride;
4-(3-{[2-(3-fluoro-phenyl)-1,3-dioxo-2,3-dihydro-1H-isoindol-5-carbonyl]-amino}-propyl)-4-morpholinium chloride;
1-(2-{[2-(4-fluoro-phenyl)-1,3-dioxo-2,3-dihydro-1H-isoindol-5-carbonyl]-amino}-ethyl)-piperidinium chloride;
1-(3-{[2-(4-fluoro-phenyl)-1,3-dioxo-2,3-dihydro-1H-isoindol-5-carbonyl]-amino}-propyl)-2-methyl-piperidinium chloride;
1-(2-{[2-(4-fluoro-phenyl)-1,3-dioxo-2,3-dihydro-1H-isoindol-5-carbonyl]-amino}-ethyl)-pyrrolidinium chloride;
1-(3-{[2-(4-fluoro-phenyl)-1,3-dioxo-2,3-dihydro-1H-isoindol-5-carbonyl]-amino}-propyl)-pyrrolidinium chloride;
4-(2-{[2-(4-fluoro-phenyl)-1,3-dioxo-2,3-dihydro-1H-isoindol-5-carbonyl]-amino}-ethyl)-4-morpholinium chloride;
4-(3-{[2-(4-fluoro-phenyl)-1,3-dioxo-2,3-dihydro-1H-isoindol-5-carbonyl]-amino}-propyl)-4-morpholinium chloride;
1-(2-{[2-(2-chloro-phenyl)-1,3-dioxo-2,3-dihydro-1H-isoindol-5-carbonyl]-amino}-ethyl)-piperidinium chloride;
1-(2-{[2-(3-chloro-phenyl)-1,3-dioxo-2,3-dihydro-1H-isoindol-5-carbonyl]-amino}-ethyl)-piperidinium chloride;
1-(2-{[2-(4-chloro-phenyl)-1,3-dioxo-2,3-dihydro-1H-isoindol-5-carbonyl]-amino}-ethyl)-piperidinium chloride;
1-{2-[(1,3-dioxo-2-o-tolyl-2,3-dihydro-1H-isoindol-5-carbonyl)-amino]-ethyl}-piperidinium chloride;
1-{3-[(1,3-dioxo-2-o-tolyl-2,3-dihydro-1H-isoindol-5-carbonyl)-amino]-propyl}-2-methyl-piperidinium chloride;
1-{2-[(1,3-dioxo-2-o-tolyl-2,3-dihydro-1H-isoindol-5-carbonyl)-amino]-ethyl}-pyrrolidinium chloride;
1-{3-[(1,3-dioxo-2-o-tolyl-2,3-dihydro-1H-isoindol-5-carbonyl)-amino]-propyl}-pyrrolidinium chloride;
4-{2-[(1,3-dioxo-2-o-tolyl-2,3-dihydro-1H-isoindol-5-carbonyl)-amino]-ethyl}-4-morpholinium chloride;
1-{2-[(1,3-dioxo-2-m-tolyl-2,3-dihydro-1H-isoindol-5-carbonyl)-amino]-ethyl}-piperidinium chloride;
1-{3-[(1,3-dioxo-2-m-tolyl-2,3-dihydro-1H-isoindol-5-carbonyl)-amino]-propyl}-2-methyl-piperidinium chloride;
1-{2-[(1,3-dioxo-2-m-tolyl-2,3-dihydro-1H-isoindol-5-carbonyl)-amino]-ethyl}-pyrrolidinium chloride;
1-{3-[(1,3-dioxo-2-m-tolyl-2,3-dihydro-1H-isoindol-5-carbonyl)-amino]-propyl}-pyrrolidinium chloride;
4-{2-[(1,3-dioxo-2-m-tolyl-2,3-dihydro-1H-isoindol-5-carbonyl)-amino]-ethyl}-4-morpholinium chloride;
4-{3-[(1,3-dioxo-2-m-tolyl-2,3-dihydro-1H-isoindol-5-carbonyl)-amino]-propyl}-4-morpholinium chloride;
1-{2-[(1,3-dioxo-2-p-tolyl-2,3-dihydro-1H-isoindol-5-carbonyl)-amino]-ethyl}-piperidinium chloride;
1-{3-[(1,3-dioxo-2-p-tolyl-2,3-dihydro-1H-isoindol-5-carbonyl)-amino]-propyl}-2-methyl-piperidinium chloride;

1-{2-[(1,3-dioxo-2-p-tolyl-2,3-dihydro-1H-isoindol-5-carbonyl)-amino]-ethyl}-pyrrolidinium chloride;

1-(3-{[2-(2-methoxy-phenyl)-1,3-dioxo-2,3-dihydro-1H-isoindol-5-carbonyl]-amino}-propyl)-2-methyl-piperidinium chloride;

1-(2-{[2-(2-methoxy-phenyl)-1,3-dioxo-2,3-dihydro-1H-isoindol-5-carbonyl]-amino}-ethyl)-pyrrolidinium chloride;

1-(3-{[2-(2-methoxy-phenyl)-1,3-dioxo-2,3-dihydro-1H-isoindol-5-carbonyl]-amino}-propyl)-pyrrolidinium chloride;

4-(3-{[2-(2-methoxy-phenyl)-1,3-dioxo-2,3-dihydro-1H-isoindol-5-carbonyl]-amino}-propyl)-4-morpholinium chloride;

1-(2-{[2-(3-methoxy-phenyl)-1,3-dioxo-2,3-dihydro-1H-isoindol-5-carbonyl]-amino}-ethyl)-piperidinium chloride;

1-(2-{[2-(4-methoxy-phenyl)-1,3-dioxo-2,3-dihydro-1H-isoindol-5-carbonyl]-amino}-ethyl)-piperidinium chloride;

1-{2-[(2-benzyl-1,3-dioxo-2,3-dihydro-1H-isoindol-5-carbonyl)-amino]-ethyl}-piperidinium chloride;

1-{3-[(2-benzyl-1,3-dioxo-2,3-dihydro-1H-isoindol-5-carbonyl)-amino]-propyl}-2-methyl-piperidinium chloride;

1-{2-[(2-benzyl-1,3-dioxo-2,3-dihydro-1H-isoindol-5-carbonyl)-amino]-ethyl}-pyrrolidinium chloride;

1-{3-[(2-benzyl-1,3-dioxo-2,3-dihydro-1H-isoindol-5-carbonyl)-amino]-propyl}-pyrrolidinium chloride;

4-{2-[(2-benzyl-1,3-dioxo-2,3-dihydro-1H-isoindol-5-carbonyl)-amino]-ethyl}-4-morpholinium chloride;

4-{3-[(2-benzyl-1,3-dioxo-2,3-dihydro-1H-isoindol-5-carbonyl)-amino]-propyl}-4-morpholinium chloride;

1-(2-{[2-(2-fluoro-benzyl)-1,3-dioxo-2,3-dihydro-1H-isoindol-5-carbonyl]-amino}-ethyl)-piperidinium chloride;

1-(3-{[2-(2-fluoro-benzyl)-1,3-dioxo-2,3-dihydro-1H-isoindol-5-carbonyl]-amino}-propyl)-2-methyl-piperidinium chloride;

1-(2-{[2-(2-fluoro-benzyl)-1,3-dioxo-2,3-dihydro-1H-isoindol-5-carbonyl]-amino}-ethyl)-pyrrolidinium chloride;

1-(3-{[2-(2-fluoro-benzyl)-1,3-dioxo-2,3-dihydro-1H-isoindol-5-carbonyl]-amino}-propyl)-pyrrolidinium chloride;

4-(2-{[2-(2-fluoro-benzyl)-1,3-dioxo-2,3-dihydro-1H-isoindol-5-carbonyl]-amino}-ethyl)-4-morpholinium chloride;

4-(3-{[2-(2-fluoro-benzyl)-1,3-dioxo-2,3-dihydro-1H-isoindol-5-carbonyl]-amino}-propyl)-4-morpholinium chloride;

1-(2-{[2-(3-fluoro-benzyl)-1,3-dioxo-2,3-dihydro-1H-isoindol-5-carbonyl]-amino}-ethyl)-piperidinium chloride;

1-(3-{[2-(3-fluoro-benzyl)-1,3-dioxo-2,3-dihydro-1H-isoindol-5-carbonyl]-amino}-propyl)-2-methyl-piperidinium chloride;

1-(2-{[2-(3-fluoro-benzyl)-1,3-dioxo-2,3-dihydro-1H-isoindol-5-carbonyl]-amino}-ethyl)-pyrrolidinium chloride;

1-(3-{[2-(3-fluoro-benzyl)-1,3-dioxo-2,3-dihydro-1H-isoindol-5-carbonyl]-amino}-propyl)-pyrrolidinium chloride;

4-(2-{[2-(3-fluoro-benzyl)-1,3-dioxo-2,3-dihydro-1H-isoindol-5-carbonyl]-amino}-ethyl)-4-morpholinium chloride;

4-(3-{[2-(3-fluoro-benzyl)-1,3-dioxo-2,3-dihydro-1H-isoindol-5-carbonyl]-amino}-propyl)-4-morpholinium chloride;

1-(3-{[2-(3-fluoro-benzyl)-1,3-dioxo-2,3-dihydro-1H-isoindol-5-carbonyl]-amino}-propyl)-4-methyl-1-piperazinium chloride;

1-(2-{[2-(4-fluoro-benzyl)-1,3-dioxo-2,3-dihydro-1H-isoindol-5-carbonyl]-amino}-ethyl)-piperidinium chloride;

1-(3-{[2-(4-fluoro-benzyl)-1,3-dioxo-2,3-dihydro-1H-isoindol-5-carbonyl]-amino}-propyl)-2-methyl-piperidinium chloride;

1-(2-{[2-(4-fluoro-benzyl)-1,3-dioxo-2,3-dihydro-1H-isoindol-5-carbonyl]-amino}-ethyl)-pyrrolidinium chloride;

1-(3-{[2-(4-fluoro-benzyl)-1,3-dioxo-2,3-dihydro-1H-isoindol-5-carbonyl]-amino}-propyl)-pyrrolidinium chloride;

4-(2-{[2-(4-fluoro-benzyl)-1,3-dioxo-2,3-dihydro-1H-isoindol-5-carbonyl]-amino}-ethyl)-4-morpholinium chloride;

4-(3-{[2-(4-fluoro-benzyl)-1,3-dioxo-2,3-dihydro-1H-isoindol-5-carbonyl]-amino}-propyl)-4-morpholinium chloride;

1-(3-{[2-(4-fluoro-benzyl)-1,3-dioxo-2,3-dihydro-1H-isoindol-5-carbonyl]-amino}-propyl)-4-methyl-1-piperazinium chloride;

1-(2-{[2-(2-chloro-benzyl)-1,3-dioxo-2,3-dihydro-1H-isoindol-5-carbonyl]-amino}-ethyl)-piperidinium chloride;

1-(3-{[2-(2-chloro-benzyl)-1,3-dioxo-2,3-dihydro-1H-isoindol-5-carbonyl]-amino}-propyl)-2-methyl-piperidinium chloride;

1-(2-{[2-(2-chloro-benzyl)-1,3-dioxo-2,3-dihydro-1H-isoindol-5-carbonyl]-amino}-ethyl)-pyrrolidinium chloride;

1-(3-{[2-(2-chloro-benzyl)-1,3-dioxo-2,3-dihydro-1H-isoindol-5-carbonyl]-amino}-propyl)-pyrrolidinium chloride;

4-(2-{[2-(2-chloro-benzyl)-1,3-dioxo-2,3-dihydro-1H-isoindol-5-carbonyl]-amino}-ethyl)-4-morpholinium chloride;

4-(3-{[2-(2-chloro-benzyl)-1,3-dioxo-2,3-dihydro-1H-isoindol-5-carbonyl]-amino}-propyl)-4-morpholinium chloride;

1-(2-{[2-(3-chloro-benzyl)-1,3-dioxo-2,3-dihydro-1H-isoindol-5-carbonyl]-amino}-ethyl)-piperidinium chloride;

1-(3-{[2-(3-chloro-benzyl)-1,3-dioxo-2,3-dihydro-1H-isoindol-5-carbonyl]-amino}-propyl)-2-methyl-piperidinium chloride;

1-(2-{[2-(3-chloro-benzyl)-1,3-dioxo-2,3-dihydro-1H-isoindol-5-carbonyl]-amino}-ethyl)-pyrrolidinium chloride;

1-(3-{[2-(3-chloro-benzyl)-1,3-dioxo-2,3-dihydro-1H-isoindol-5-carbonyl]-amino}-propyl)-pyrrolidinium chloride;

4-(2-{[2-(3-chloro-benzyl)-1,3-dioxo-2,3-dihydro-1H-isoindol-5-carbonyl]-amino}-ethyl)-4-morpholinium chloride;

4-(3-{[2-(3-chloro-benzyl)-1,3-dioxo-2,3-dihydro-1H-isoindol-5-carbonyl]-amino}-propyl)-4-morpholinium chloride;

1-(2-{[2-(4-chloro-benzyl)-1,3-dioxo-2,3-dihydro-1H-isoindol-5-carbonyl]-amino}-ethyl)-piperidinium chloride;

1-(3-{[2-(4-chloro-benzyl)-1,3-dioxo-2,3-dihydro-1H-isoindol-5-carbonyl]-amino}-propyl)-2-methyl-piperidinium chloride;

1-(2-{[2-(4-chloro-benzyl)-1,3-dioxo-2,3-dihydro-1H-isoindol-5-carbonyl]-amino}-ethyl)-pyrrolidinium chloride;

1-(3-{[2-(4-fluoro-benzyl)-1,3-dioxo-2,3-dihydro-1H-isoindol-5-carbonyl]-amino}-propyl)-pyrrolidinium chloride;

4-(2-{[2-(4-chloro-benzyl)-1,3-dioxo-2,3-dihydro-1H-isoindol-5-carbonyl]-amino}-ethyl)-4-morpholinium chloride;

4-(3-{[2-(4-chloro-benzyl)-1,3-dioxo-2,3-dihydro-1H-isoindol-5-carbonyl]-amino}-propyl)-4-morpholinium chloride;

1-(2-{[2-(2-methyl-benzyl)-1,3-dioxo-2,3-dihydro-1H-isoindol-5-carbonyl]-amino}-ethyl)-piperidinium chloride;

2-methyl-1-(3-{[2-(3-methyl-benzyl)-1,3-dioxo-2,3-dihydro-1H-isoindol-5-carbonyl]-amino}-propyl)-piperidinium chloride;

1-(2-{[2-(3-methyl-benzyl)-1,3-dioxo-2,3-dihydro-1H-isoindol-5-carbonyl]-amino}-ethyl)-pyrrolidinium chloride;

1-(3-{[2-(2-methyl-benzyl)-1,3-dioxo-2,3-dihydro-1H-isoindol-5-carbonyl]-amino}-propyl)-pyrrolidinium chloride;

4-(2-{[2-(2-methyl-benzyl)-1,3-dioxo-2,3-dihydro-1H-isoindol-5-carbonyl]-amino}-ethyl)-4-morpholinium chloride;

4-(3-{[2-(2-methyl-benzyl)-1,3-dioxo-2,3-dihydro-1H-isoindol-5-carbonyl]-amino}-propyl)-4-morpholinium chloride;

1-(2-{[2-(3-methyl-benzyl)-1,3-dioxo-2,3-dihydro-1H-isoindol-5-carbonyl]-amino}-ethyl)-piperidinium chloride;

2-methyl-1-(3-{[2-(3-methyl-benzyl)-1,3-dioxo-2,3-dihydro-1H-isoindol-5-carbonyl]-amino}-propyl)-piperidinium chloride;

1-(2-{[2-(3-methyl-benzyl)-1,3-dioxo-2,3-dihydro-1H-isoindol-5-carbonyl]-amino}-ethyl)-pyrrolidinium chloride;

1-(3-{[2-(3-methyl-benzyl)-1,3-dioxo-2,3-dihydro-1H-isoindol-5-carbonyl]-amino}-propyl)-pyrrolidinium chloride;

4-(2-{[2-(3-methyl-benzyl)-1,3-dioxo-2,3-dihydro-1H-isoindol-5-carbonyl]-amino}-ethyl)-4-morpholinium chloride;

4-(3-{[2-(3-methyl-benzyl)-1,3-dioxo-2,3-dihydro-1H-isoindol-5-carbonyl]-amino}-propyl)-4-morpholinium chloride;

1-(2-{[2-(4-methyl-benzyl)-1,3-dioxo-2,3-dihydro-1H-isoindol-5-carbonyl]-amino}-ethyl)-piperidinium chloride;

1-(3-{[2-(4-methyl-benzyl)-1,3-dioxo-2,3-dihydro-1H-isoindol-5-carbonyl]-amino}-propyl)-piperidinium chloride;

1-(2-{[2-(4-methyl-benzyl)-1,3-dioxo-2,3-dihydro-1H-isoindol-5-carbonyl]-amino}-ethyl)-pyrrolidinium chloride;

1-(3-{[2-(4-methyl-benzyl)-1,3-dioxo-2,3-dihydro-1H-isoindol-5-carbonyl]-amino}-propyl)-pyrrolidinium chloride;

4-(2-{[2-(4-methyl-benzyl)-1,3-dioxo-2,3-dihydro-1H-isoindol-5-carbonyl]-amino}-ethyl)-4-morpholinium chloride;

4-(3-{[2-(4-methyl-benzyl)-1,3-dioxo-2,3-dihydro-1H-isoindol-5-carbonyl]-amino}-propyl)-4-morpholinium chloride;

1-(2-{[2-(2-methoxy-benzyl)-1,3-dioxo-2,3-dihydro-1H-isoindol-5-carbonyl]-amino}-ethyl)-piperidinium chloride;

1-(3-{[2-(2-methoxy-benzyl)-1,3-dioxo-2,3-dihydro-1H-isoindol-5-carbonyl]-amino}-propyl)-2-methyl-piperidinium chloride;

1-(2-{[2-(2-methoxy-benzyl)-1,3-dioxo-2,3-dihydro-1H-isoindol-5-carbonyl]-amino}-ethyl)-pyrrolidinium chloride;

1-(3-{[2-(2-methoxy-benzyl)-1,3-dioxo-2,3-dihydro-1H-isoindol-5-carbonyl]-amino}-propyl)-pyrrolidinium chloride;

4-(2-{[2-(2-methoxy-benzyl)-1,3-dioxo-2,3-dihydro-1H-isoindol-5-carbonyl]-amino}-ethyl)-4-morpholinium chloride;

4-(3-{[2-(2-methoxy-benzyl)-1,3-dioxo-2,3-dihydro-1H-isoindol-5-carbonyl]-amino}-propyl)-4-morpholinium chloride;

1-(2-{[2-(3-methoxy-benzyl)-1,3-dioxo-2,3-dihydro-1H-isoindol-5-carbonyl]-amino}-ethyl)-piperidinium chloride;

1-(3-{[2-(3-methoxy-benzyl)-1,3-dioxo-2,3-dihydro-1H-isoindol-5-carbonyl]-amino}-propyl)-2-methyl-piperidinium chloride;

1-(2-{[2-(3-methoxy-benzyl)-1,3-dioxo-2,3-dihydro-1H-isoindol-5-carbonyl]-amino}-ethyl)-pyrrolidinium chloride;

1-(3-{[2-(3-methoxy-benzyl)-1,3-dioxo-2,3-dihydro-1H-isoindol-5-carbonyl]-amino}-propyl)-pyrrolidinium chloride;

4-(2-{[2-(3-methoxy-benzyl)-1,3-dioxo-2,3-dihydro-1H-isoindol-5-carbonyl]-amino}-ethyl)-4-morpholinium chloride;

4-(3-{[2-(3-methoxy-benzyl)-1,3-dioxo-2,3-dihydro-1H-isoindol-5-carbonyl]-amino}-propyl)-4-morpholinium chloride;

1-(2-{[2-(4-methoxy-benzyl)-1,3-dioxo-2,3-dihydro-1H-isoindol-5-carbonyl]-amino}-ethyl)-piperidinium chloride;

1-(3-{[2-(4-methoxy-benzyl)-1,3-dioxo-2,3-dihydro-1H-isoindol-5-carbonyl]-amino}-propyl)-2-methyl-piperidinium chloride;

1-(2-{[2-(4-methoxy-benzyl)-1,3-dioxo-2,3-dihydro-1H-isoindol-5-carbonyl]-amino}-ethyl)-pyrrolidinium chloride;

1-(3-{[2-(4-methoxy-benzyl)-1,3-dioxo-2,3-dihydro-1H-isoindol-5-carbonyl]-amino}-propyl)-pyrrolidinium chloride;

4-(2-{[2-(4-methoxy-benzyl)-1,3-dioxo-2,3-dihydro-1H-isoindol-5-carbonyl]-amino}-ethyl)-4-morpholinium chloride;

4-(3-{[2-(4-methoxy-benzyl)-1,3-dioxo-2,3-dihydro-1H-isoindol-5-carbonyl]-amino}-propyl)-4-morpholinium chloride;

1-(2-{[2-(4-cyano-benzyl)-1,3-dioxo-2,3-dihydro-1H-isoindol-5-carbonyl]-amino}-ethyl)-piperidinium chloride;

1-(3-{[2-(4-cyano-benzyl)-1,3-dioxo-2,3-dihydro-1H-isoindol-5-carbonyl]-amino}-propyl)-2-methyl-piperidinium chloride;

1-(2-{[2-(4-cyano-benzyl)-1,3-dioxo-2,3-dihydro-1H-isoindol-5-carbonyl]-amino}-ethyl)-pyrrolidinium chloride;

1-(3-{[2-(4-cyano-benzyl)-1,3-dioxo-2,3-dihydro-1H-isoindol-5-carbonyl]-amino}-propyl)-pyrrolidinium chloride;

4-(2-{[2-(4-cyano-benzyl)-1,3-dioxo-2,3-dihydro-1H-isoindol-5-carbonyl]-amino}-ethyl)-4-morpholinium chloride; and 4-(3-{[2-(4-cyano-benzyl)-1,3-dioxo-2,3-dihydro-1H-isoindol-5-carbonyl]-amino}-propyl)-4-morpholinium chloride.

4. A process for preparing a 1,3-dioxoisoindole compound of Formula (1), the process comprising performing amide condensation reaction between 1,3-dioxoisoindole 5-carboxylic acid compounds of Formula (2) and azacyclic N-alkyl amine compound of Formula (3):

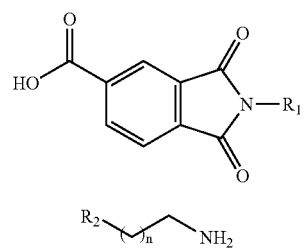

-continued

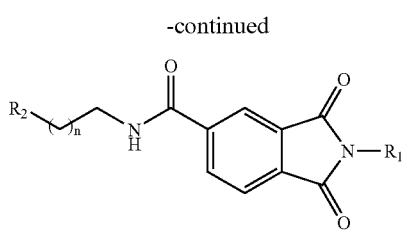
(1)

wherein R₁, R₂, and n are same as defined in claim 1.

5. The process of claim 4, wherein the amide condensation reaction comprises:
(a) preparing an acyl chloride compound as an intermediate compound by reacting 1,3-dioxoisoindole 5-carboxylic acid compounds of Formula (2) with an acylating reagent, and
(b) preparing 1,3-dioxoisoindole compounds of Formula (1) by reacting the acyl chloride compound with azacyclic N-alkyl amine compound of Formula (3).

6. The process of claim 5, wherein the acylating reagent is oxalyl chloride or thionyl chloride.

7. A composition for treating diseases selected from a group consisting of epilepsy, hypertension, stenocardia and neurogenic pains caused by antagonism of T-type calcium channel, the composition comprising 1,3-dioxoisoindole compounds of Formula (1) or pharmaceutically acceptable salts thereof:

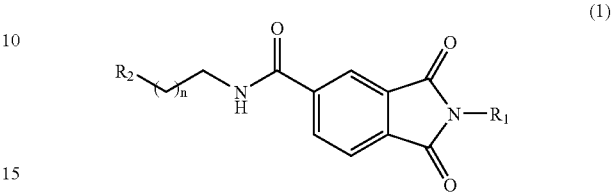
(1)

wherein R₁, R₂, and n are same as defined in claim 1.

8. The composition according to claim 7, wherein the disease is epilepsy.

9. The composition according to claim 7, wherein the disease is hypertension or stenocardia.

* * * * *